(12) United States Patent
Beard et al.

(10) Patent No.: US 8,492,556 B2
(45) Date of Patent: Jul. 23, 2013

(54) 2,5-DIOXOIMIDAZOLIDIN-1-YL-3-PHENYLUREA DERIVATIVES AS FORMYL PEPTIDE RECEPTOR LIKE-1 (FPRL-1) RECEPTOR MODULATORS

(71) Applicant: Allergan, Inc., Irvine, CA (US)

(72) Inventors: Richard L. Beard, Newport Beach, CA (US); Vidyasagar Vuligonda, Irvine, CA (US); Thong Vu, Garden Grove, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/673,800

(22) Filed: Nov. 9, 2012

(65) Prior Publication Data

US 2013/0123215 A1 May 16, 2013

Related U.S. Application Data

(60) Provisional application No. 61/558,080, filed on Nov. 10, 2011.

(51) Int. Cl.
| | | |
|---|---|---|
| C07D 217/24 | (2006.01) | |
| C07D 233/02 | (2006.01) | |
| C07D 235/02 | (2006.01) | |
| C07D 213/16 | (2006.01) | |

(52) U.S. Cl.
USPC .... 548/316.7; 546/81; 546/274.4; 548/301.4; 548/311.1; 548/312.1

(58) Field of Classification Search
USPC .................................................. 514/94, 390
See application file for complete search history.

(56) References Cited

PUBLICATIONS

Schlogl, K. et al. "α-Amino-N-carboxylic acid dihydrazides and their derivatives." Monatshefte fur Chemie 1954, 85, 607-626.*
Cilibrizzi, Agostino et al, 6-Methyl-2,2-Disubstituted Pyridazin-3(2H)-ones: a Novel Class of Small-Molecule Agonists for Formyl Peptide Receptors, Journal of Medicinal Chemistry, Aug. 27, 2009, 5044-5057, 52 (16).
Cross, L.C. et al, Rules for the Nomenclature of Organic Chemistry, Section E: Stereochemistry, Pure & Appl. Chem., 1976, 11-30, 45.
Database Registry Chemical Abstracts Service, STN Database accession No. 879346-46-0, Apr. 5, 2006, 1 Page, Columbus, Ohio.
Database Registry Chemical Abstracts Service, STN Database accession No. 1052620-77-5, Sep. 25, 2008, 1 Page, Columbus, Ohio.
Database Registry Chemical Abstracts Service, STN Database accession No. 1189940-16-6, Oct. 25, 2009, 1 Page, Columbus, Ohio.
Database Registry Chemical Abstracts Service, STN Database accession No. 923193-08-2, Feb. 26, 2007, 1 Page, Columbus, Ohio.
Kirpotina, Liliya, Identification of Novel Small-Molecule Agonists for Human Formyl Peptide Receptors and Pharmacophore Models of Their Recognition, Molecular Pharmacology, Feb. 2010, 159-170, 77 (2).
Migeotte, Isabelle et al., Formyl peptide receptors: a promiscuous subfamily of G protein-coupled receptors controlling immune responses, Cytokine & Growth Factor Reviews, 2006, 501-519, 17, US.
Perretti, Mauro et al, Therapeutic Anti-Inflammatory Potential of Formyl-Peptide Receptor Agonists, Pharmacology & Research, 2010, 175-188, 127.
Roland Burli, Potent hFPRL1 (ALXR) Agonists as Potential Anti-Inflammatory Agents, Bioorganic & Medicinal Chemistry Letters, 2006, 3713-3718, 16.
Stahl, Heinrich et al, Handbook of Pharmaceutical Salts, Verlag Helvetica Chimica Acta—Zurich, 2002, 329-345.
Patent Cooperation Treaty, Notification of Transmittal of the International Search Report and the Written Opinion of the International Searching Authority, or the Declaration, Form PCT/ISA/220, Int. App. No. PCT/US2012/064571, Dec. 21, 2012.

\* cited by examiner

*Primary Examiner* — Joseph K McKane
*Assistant Examiner* — Amananda L Aguirre
(74) *Attorney, Agent, or Firm* — Doina G. Ene

(57) ABSTRACT

The present invention relates to novel 2,5-dioxoimidazolidin-1-yl-3-phenylurea derivatives, processes for preparing them, pharmaceutical compositions containing them and their use as pharmaceuticals as modulators of the N-formyl peptide receptor like-1 (FPRL-1) receptor.

15 Claims, No Drawings

2,5-DIOXOIMIDAZOLIDIN-1-YL-3-PHENYLUREA DERIVATIVES AS FORMYL PEPTIDE RECEPTOR LIKE-1 (FPRL-1) RECEPTOR MODULATORS

RELATED APPLICATION

This application claims the benefit of U.S. Provisional Application Ser. No. 61/558,080, filed Nov. 10, 2011, the disclosure of which is hereby incorporated in its entirety herein by reference

FIELD OF THE INVENTION

The present invention relates to novel 2,5-dioxoimidazolidin-1-yl-3-phenylurea derivatives, processes for preparing them, pharmaceutical compositions containing them and their use as pharmaceuticals as modulators of the N-formyl peptide receptor like-1 (FPRL-1) receptor. The invention relates specifically to the use of these compounds and their pharmaceutical compositions to treat disorders associated with the N-formyl peptide receptor like-1 (FPRL-1) receptor modulation.

BACKGROUND OF THE INVENTION

The N-formyl peptide receptor like-1 (FPRL-1) receptor, also known as the N-formyl peptide receptor 2 (FPR2), is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide human, anti-inflammatory eicosanoid lipoxin A4 (LXA4) and glucocorticoid-modulated protein annexin A1. FPRL-1 transduces anti-inflammatory effects of LXA4 in many systems, but it also can mediate the proinflammatory signaling cascade of peptides such as SAA. The ability of the receptor to mediate two opposite effects is proposed to be a result of different receptor domains used by different agonists (Parmentier, Marc et al. Cytokine & Growth Factor Reviews 17 (2006) 501-519).

Activation of FPRL-1 by LXA4 or its analogs and by Annexin I protein has been shown to result in anti-inflammatory activity by promoting active resolution of inflammation which involves inhibition of polymorphonuclear neutrophil (PMN) and eosinophil migration and also stimulate monocyte migration enabling clearance of apoptotic cells from the site of inflammation in a nonphlogistic manner. In addition, FPRL-1 has been shown to inhibit natural killer (NK) cell cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

We have now discovered a group of novel compounds which are potent and selective FPRL-1 modulators. As such, the compounds described herein are useful in treating a wide variety of disorders associated with modulation of FPRL-1 receptor. The term "modulator" as used herein, includes but is not limited to: receptor agonist, antagonist, inverse agonist, inverse antagonist, partial agonist, partial antagonist.

This invention describes compounds of Formula I, which have FPRL-1 receptor biological activity. The compounds in accordance with the present invention are thus of use in medicine, for example in the treatment of humans with diseases and conditions that are alleviated by FPRL-1 modulation.

In one aspect, the invention provides a compound having Formula I or the geometrical isomers, enantiomers, diastereoisomers, zwitterions, hydrates, solvates or a pharmaceutically acceptable salt thereof:

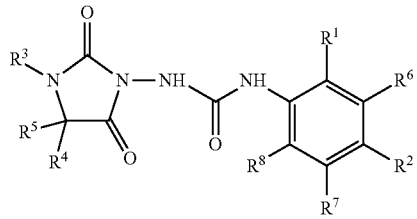

Formula I $R^1$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;

$R^2$ is halogen, optionally substituted $C_{1-8}$ alkyl, $CF_3$, $OR^9$, $C(O)R^{10}$, $NO_2$, $NR^{13}R^{14}$, CN, $SR^{15}$ or $SO_2R^{16}$;

$R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a 5 or 6 member ring which is optionally substituted;

$R^4$ is hydrogen, optionally substituted $C_{1-8}$ alkyl,

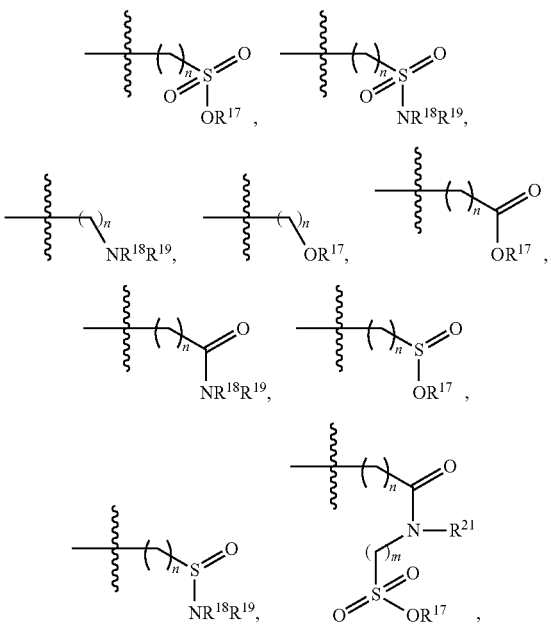

-continued

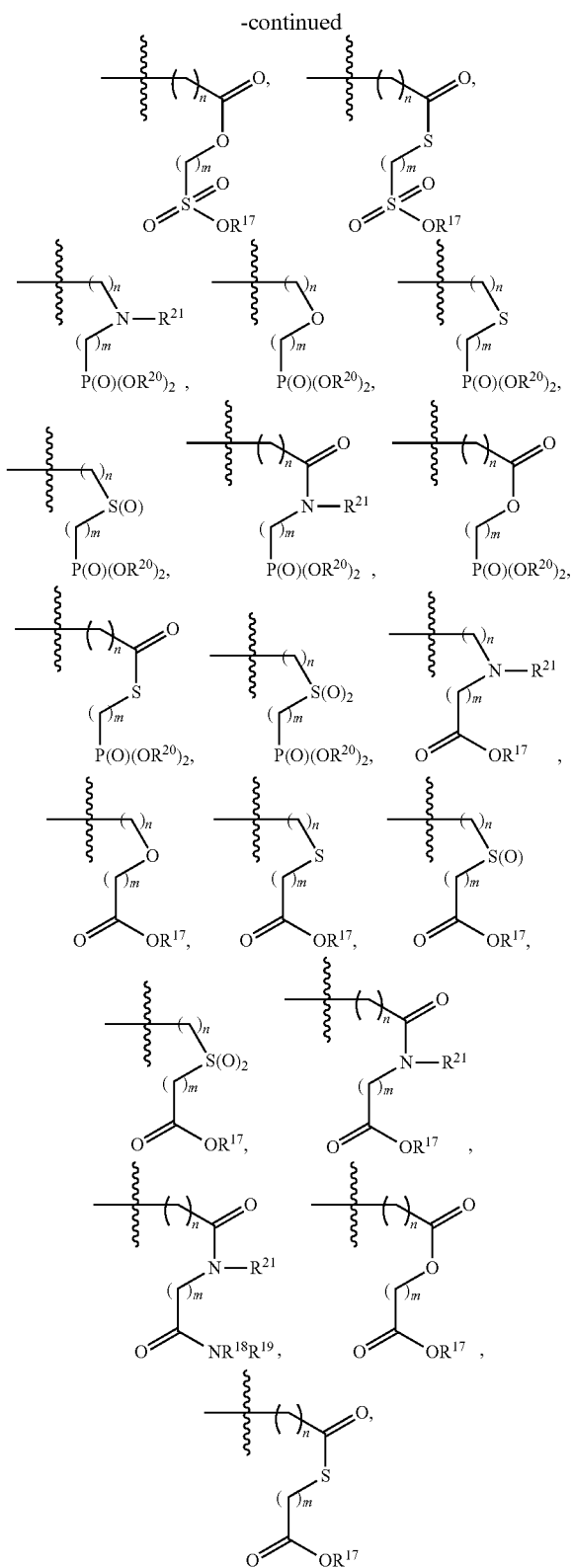

optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a spiro monocyclic or polycyclic, carbocyclic or heterocyclic, saturated or unsaturated 5 to 10 member ring which is optionally substituted;

$R^5$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^4$ forms a spiro monocyclic or polycyclic carbocyclic or heterocyclic, saturated or unsaturated 5 to 10 member ring which is optionally substituted or together with $R^3$ forms a 5 or 6 member ring which is optionally substituted;

$R^6$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;

$R^7$ is halogen, hydrogen, optionally substituted $C_{1-8}$ alkyl, $OR^9$, $C(O)R^{16}$, $NO_2$, $NR^{13}R^{14}$, CN, $SR^{15}$ or $SO_2R^{16}$;

$R^8$ is halogen, hydrogen, optionally substituted $C_{1-8}$ alkyl, $OR^9$, $C(O)R^{16}$, $NO_2$, $NR^{13}R^{14}$, CN, $SR^{15}$ or $SO_2R^{16}$;

$R^9$ is hydrogen, $C(O)(C_{1-8}$ alkyl) or optionally substituted $C_{1-8}$ alkyl;

$R^{10}$ is hydrogen, optionally substituted $C_{1-8}$ alkyl, $O(C_{1-8}$ alkyl), $NR^{11}R^{12}$ or OH;

$R^{11}$ is hydrogen, optionally substituted $C_{6-10}$ aryl or optionally substituted $C_{1-8}$ alkyl;

$R^{12}$ is hydrogen, optionally substituted $C_{6-10}$ aryl or optionally substituted $C_{1-8}$ alkyl;

$R^{13}$ is hydrogen, optionally substituted $C_{6-10}$ aryl or optionally substituted $C_{1-8}$ alkyl;

$R^{14}$ is hydrogen, optionally substituted $C_{6-10}$ aryl, optionally substituted $C_{1-8}$ alkyl, $C(O)(C_{1-8}$ alkyl) or $SO_2(C_{1-8}$ alkyl);

$R^{15}$ is hydrogen, optionally substituted $C_{1-8}$ alkyl or $O(C_{1-8}$ alkyl);

$R^{16}$ is OH, $O(C_{1-8}$ alkyl), $(C_{1-8}$ alkyl) or $NR^{11}R^{12}$;

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl, or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5;

m is 1, 2, 3, 4, or 5; and with the proviso that the compound of Formula I is not of structures:

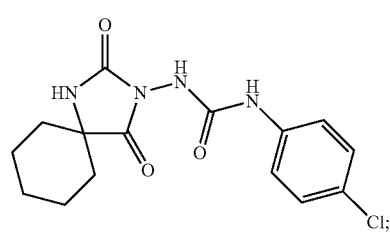

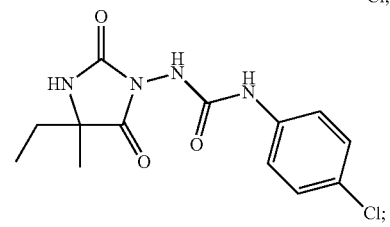

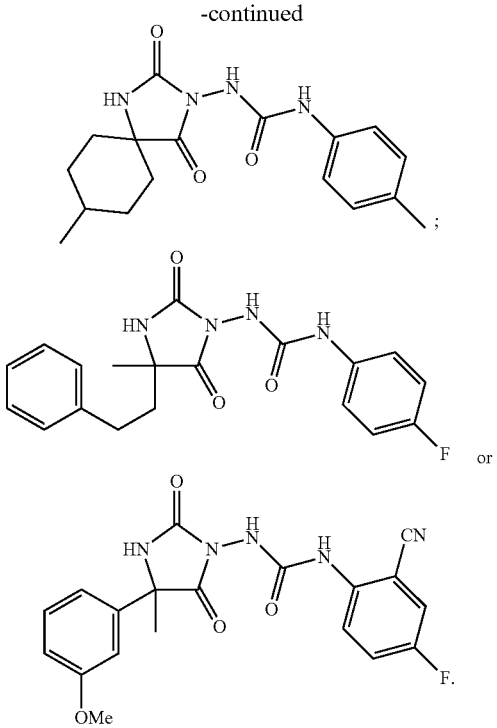

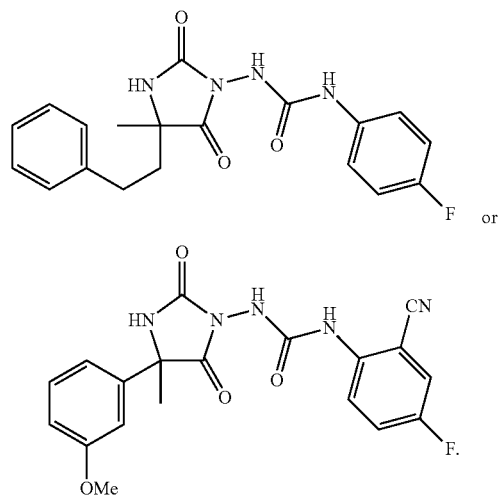

In another aspect, the invention provides a compound having Formula I wherein:

$R^1$ is halogen, hydrogen or optionally substituted $C_{1-8}$ alkyl;
$R^2$ is halogen, optionally substituted $C_{1-8}$ alkyl, $CF_3$, $SR^{15}$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^5$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl); and
with the proviso that the compound of Formula I is not of structures:

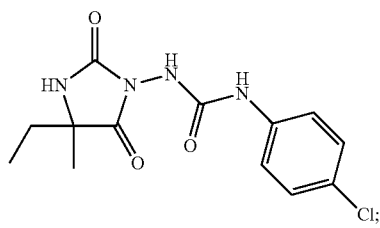

In another aspect, the invention provides a compound having Formula I wherein:

$R^1$ is halogen, hydrogen or optionally substituted $C_{1-8}$ alkyl;
$R^2$ is halogen, optionally substituted $C_{1-8}$ alkyl, $CF_3$, $SR^{15}$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is optionally substituted $C_{1-8}$ alkyl, optionally substituted $C_{6-10}$ aryl

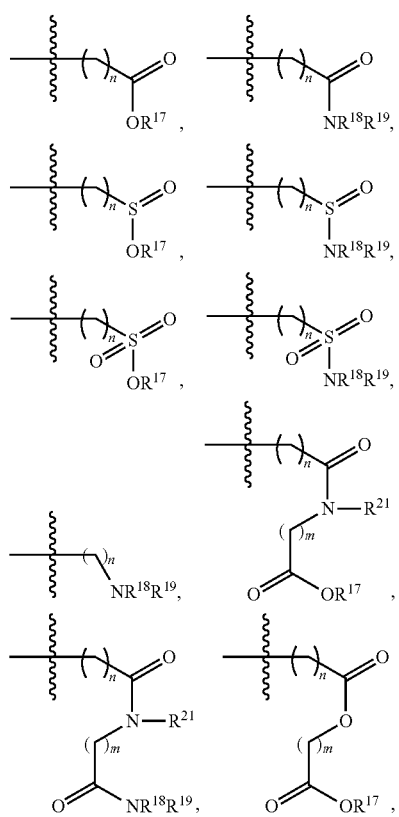

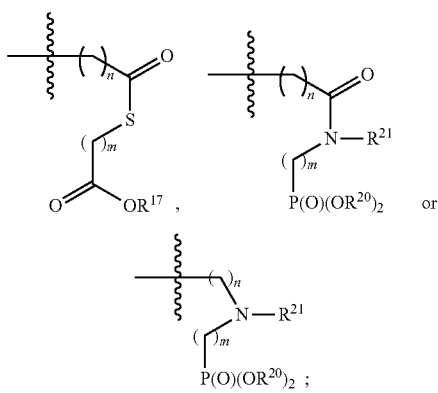

$R^5$ is optionally substituted $C_{1-8}$ alkyl or optionally substituted $C_{3-8}$ cycloalkyl;

$R^6$ is halogen, hydrogen or optionally substituted $C_{1-8}$ alkyl;

$R^7$ is halogen, hydrogen or optionally substituted $C_{1-8}$ alkyl;

$R^8$ is halogen, hydrogen or optionally substituted $C_{1-8}$ alkyl;

$R^9$ is hydrogen, $C(O)(C_{1-8}$ alkyl) or optionally substituted $C_{1-8}$ alkyl;

$R^{15}$ is hydrogen, optionally substituted $C_{1-8}$ alkyl or $O(C_{1-8}$ alkyl);

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5;

m is 1, 2, 3, 4, or 5; and with the proviso that the compound of Formula I is not of structures:

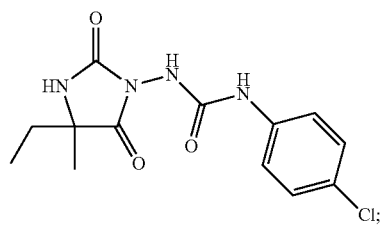

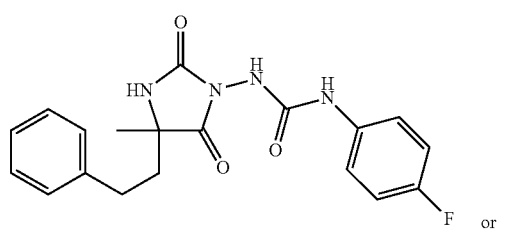

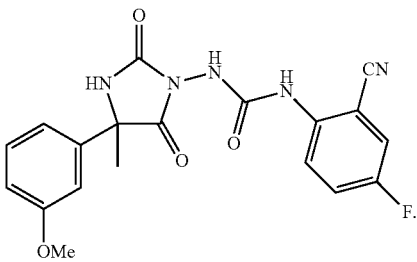

In another aspect, the invention provides a compound having Formula I wherein:

$R^1$ is halogen, hydrogen or optionally substituted $C_{1-8}$ alkyl;

$R^2$ is halogen, optionally substituted $C_{1-8}$ alkyl, $SR^{15}$, $CF_3$, $OR^9$ or CN;

$R^3$ is hydrogen;

$R^4$ is optionally substituted $C_{1-8}$ alkyl, optionally substituted $C_{6-10}$ aryl

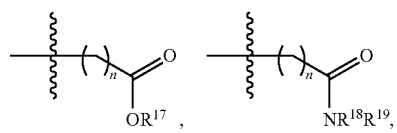

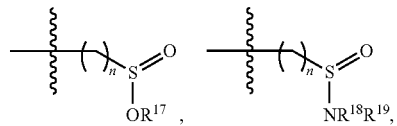

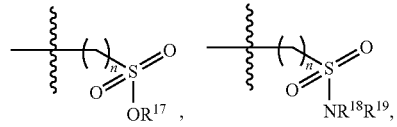

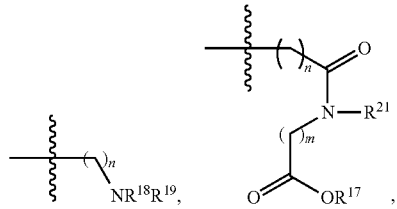

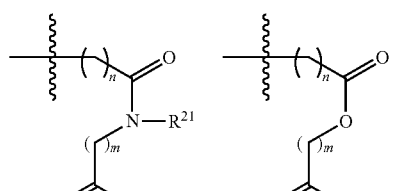

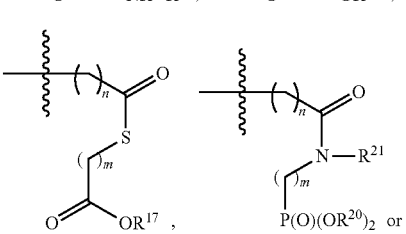

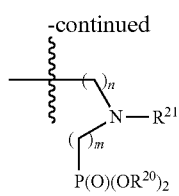

$R^5$ is optionally substituted $C_{1-8}$ alkyl or optionally substituted $C_{3-8}$ cycloalkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, C(O)($C_{1-8}$ alkyl) or optionally substituted $C_{1-8}$ alkyl;
$R^{15}$ is hydrogen, optionally substituted $C_{1-8}$ alkyl or O($C_{1-8}$ alkyl);
$R^{17}$ is hydrogen, optionally substituted $C_{6-10}$ aryl or optionally substituted $C_{1-8}$ alkyl;
$R^{18}$ is hydrogen, C(O)($C_{1-8}$ alkyl), optionally substituted $C_{6-10}$ aryl or optionally substituted $C_{1-8}$ alkyl;
$R^{19}$ is hydrogen, C(O)($C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5;
m is 1, 2, 3, 4, or 5; and
with the proviso that the compound of Formula I is not of structures:

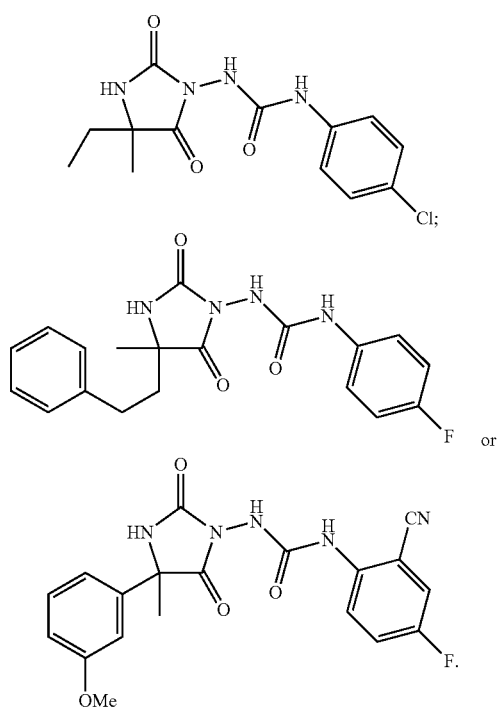

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $CF_3$, $SR^{15}$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;

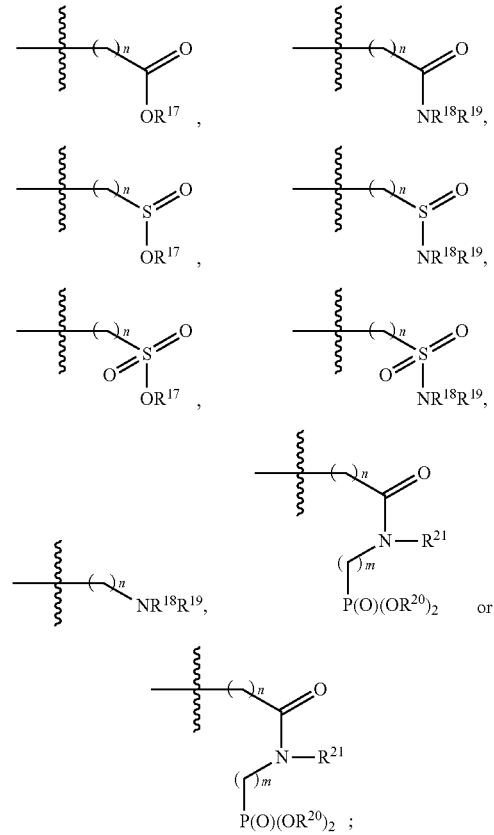

$R^4$ is optionally substituted $C_{1-8}$ alkyl,
$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, C(O)($C_{1-8}$ alkyl) or optionally substituted $C_{1-8}$ alkyl;
$R^{15}$ is hydrogen, optionally substituted $C_{1-8}$ alkyl or O($C_{1-8}$ alkyl);
$R^{17}$ is hydrogen, optionally substituted $C_{6-10}$ aryl or optionally substituted $C_{1-8}$ alkyl;
$R^{18}$ is hydrogen, C(O)($C_{1-8}$ alkyl), optionally substituted $C_{6-10}$ aryl or optionally substituted $C_{1-8}$ alkyl;
$R^{19}$ is hydrogen, C(O)($C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5;
m is 1, 2, 3, 4, or 5; and
with the proviso that the compound of Formula I is not of structures:

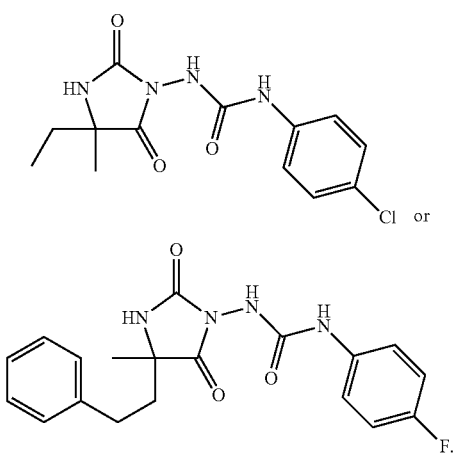

In another aspect, the invention provides a compound having Formula I wherein:

$R^1$ is halogen, hydrogen or optionally substituted $C_{1-8}$ alkyl;

$R^2$ is halogen, optionally substituted $C_{1-8}$ alkyl, $CF_3$, $SR^{15}$, $OR^9$ or CN;

$R^3$ is hydrogen, optionally substituted $C_{1-8}$ alkyl, optionally substituted $C_{3-8}$ cycloalkyl or optionally substituted $C_{3-8}$ cycloalkenyl;

$R^4$ is

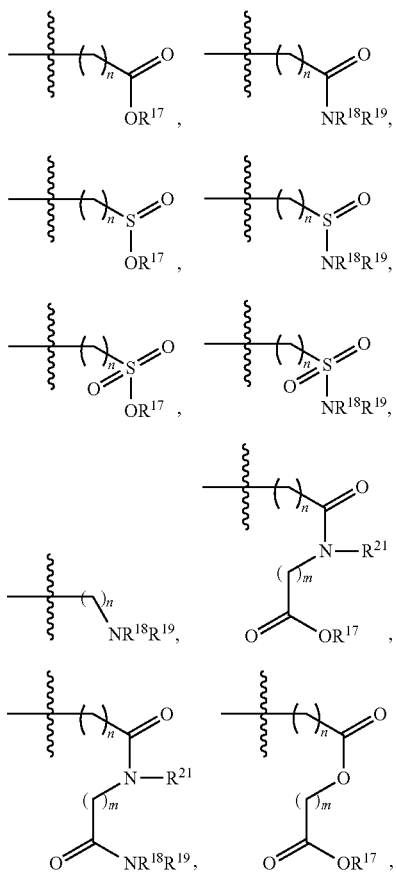

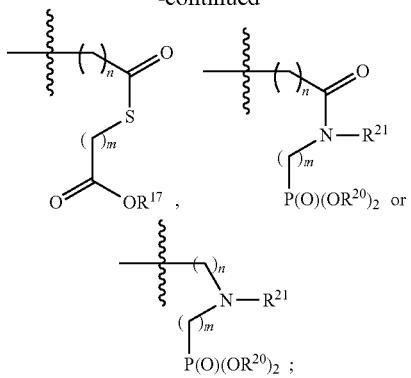

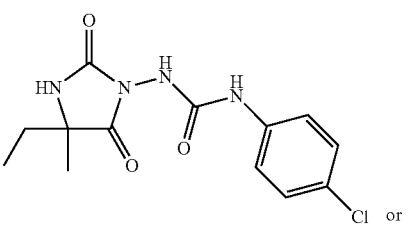

$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl);
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl), optionally substituted $C_{6-10}$ aryl or optionally substituted $C_{1-8}$ alkyl;
$R^{19}$ is hydrogen, $C(O)(C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5;
m is 1, 2, 3, 4, or 5; and
with the proviso that the compound of Formula I is not of structures:

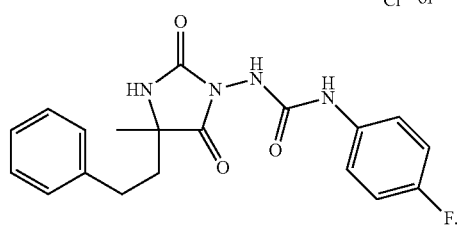

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $CF_3$, $SR^{15}$, $OR^9$ or CN;
$R^3$ is hydrogen;

$R^4$ is

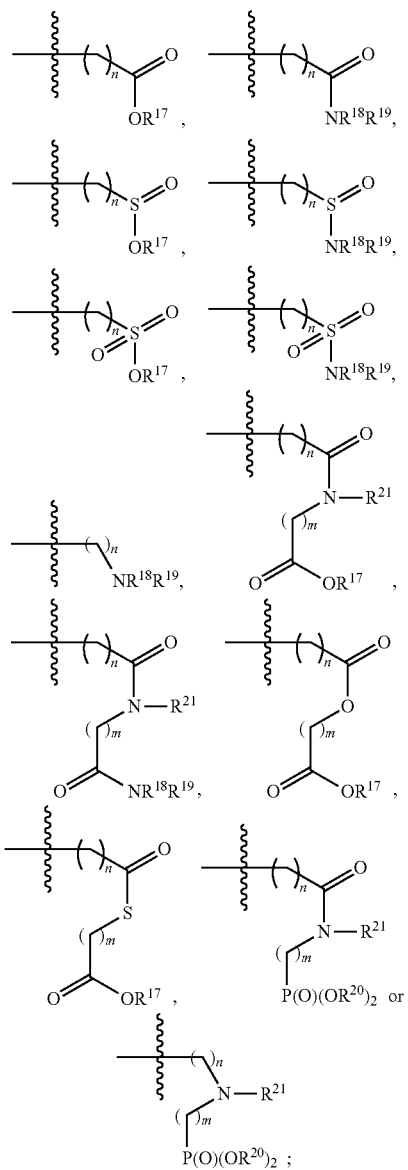

$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl);
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl), optionally substituted $C_{6-10}$ aryl or optionally substituted $C_{1-8}$ alkyl;
$R^{19}$ is hydrogen, $C(O)(C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;

n is 1, 2, 3, 4, or 5
m is 1, 2, 3, 4, or 5; and
with the proviso that the compound of Formula I is not of structures:

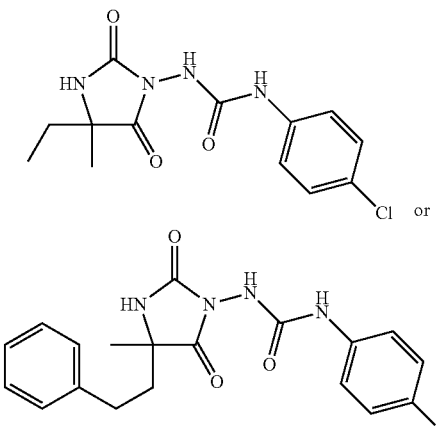

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is optionally substituted $C_{1-8}$ alkyl;
$R^5$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl); and
with the proviso that the compound of Formula I is not of structures:

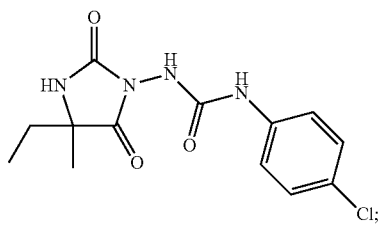

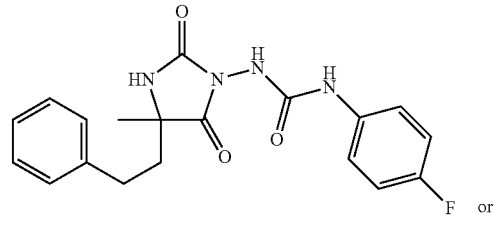

-continued

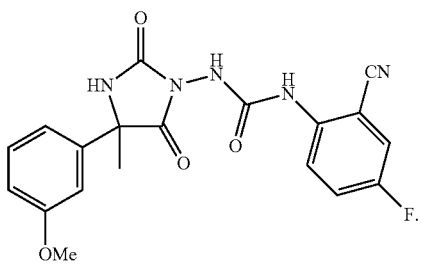

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is optionally substituted $C_{1-8}$ alkyl,

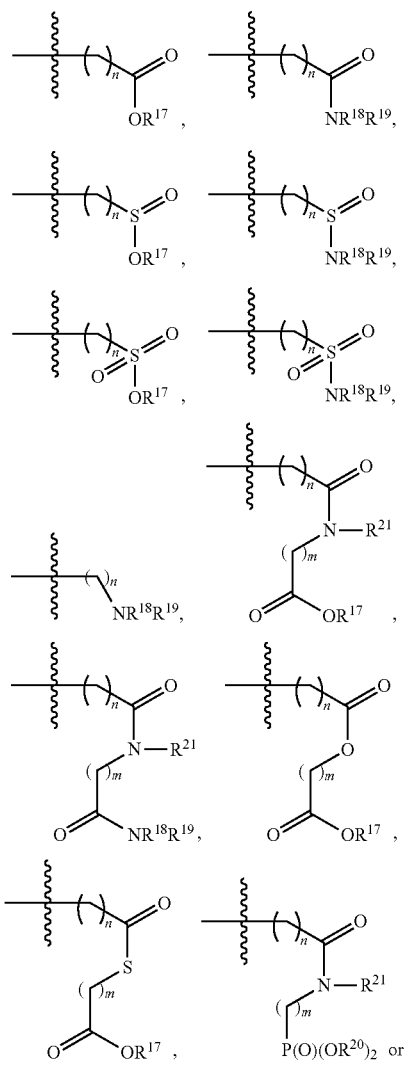

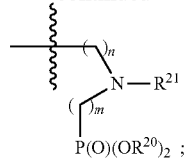

$R^5$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl$)$ or optionally substituted $C_{1-8}$ alkyl;
$R^{15}$ is hydrogen, optionally substituted $C_{1-8}$ alkyl or $O(C_{1-8}$ alkyl$)$;
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl$)$, optionally substituted $C_{6-10}$ aryl or optionally substituted $C_{1-8}$ alkyl;
$R^{19}$ is hydrogen, $C(O)(C_{1-8}$ alkyl$)$, optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5
m is 1, 2, 3, 4, or 5; and
with the proviso that the compound of Formula I is not of structures:

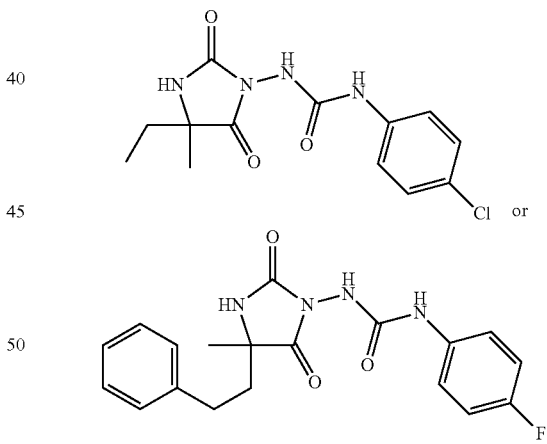

In another aspect, the invention provides a compound having Formula I wherein:
$R^1$ is halogen or hydrogen;
$R^2$ is halogen, optionally substituted $C_{1-8}$ alkyl, $SR^{15}$, $CF_3$, $OR^9$ or CN;
$R^3$ is hydrogen;
$R^4$ is optionally substituted $C_{1-8}$ alkyl;
$R^5$ is optionally substituted $C_{1-8}$ alkyl;
$R^6$ is halogen or hydrogen;
$R^7$ is hydrogen;
$R^8$ is hydrogen;
$R^9$ is optionally substituted $C_{1-8}$ alkyl;

$R^{15}$ is hydrogen, optionally substituted $C_{1-8}$ alkyl or $O(C_{1-8}$ alkyl); and with the proviso that the compound of Formula I is not of structures:

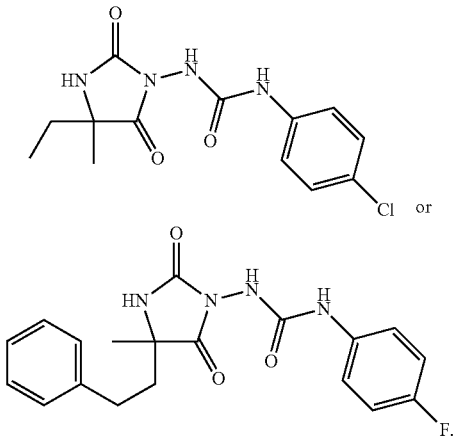

or

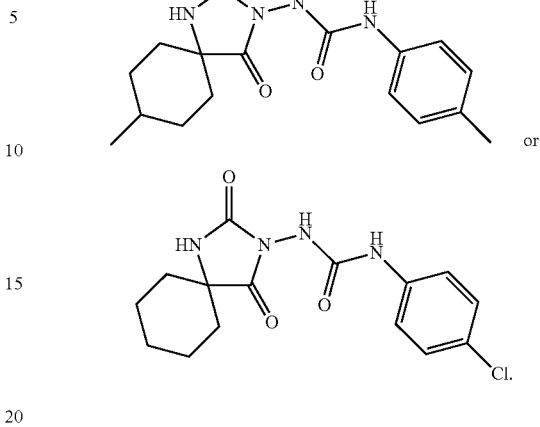

In another aspect, the invention provides a compound having Formula I wherein:
$R^1$ is halogen, hydrogen, optionally substituted $C_{1-8}$ alkyl;
$R^2$ is halogen, optionally substituted $C_{1-8}$ alkyl, $SR^{15}$, $CF_3$, $OR^9$ or CN;
$R^3$ together with $R^5$ forms a 5 or 6 member ring which is optionally substituted;
$R^4$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle,
$R^5$ together with $R^3$ forms a 5 or 6 member ring which is optionally substituted;
$R^6$ is halogen, hydrogen, optionally substituted $C_{1-8}$ alkyl;
$R^7$ is halogen, hydrogen, optionally substituted $C_{1-8}$ alkyl;
$R^8$ is halogen, hydrogen, optionally substituted $C_{1-8}$ alkyl;
$R^9$ is hydrogen or optionally substituted $C_{1-8}$ alkyl; and
$R^{15}$ is hydrogen, optionally substituted $C_{1-8}$ alkyl or $O(C_{1-8}$ alkyl).

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^4$ together with $R^5$ forms a spiro monocyclic or polycyclic, carbocyclic or heterocyclic, saturated or unsaturated 5 to 10 member ring which is optionally substituted;
$R^5$ together with $R^4$ forms a spiro monocyclic or polycyclic carbocyclic or heterocyclic, saturated or unsaturated 5 to 10 member ring which is optionally substituted;
$R^6$ is halogen, hydrogen, optionally substituted $C_{1-8}$ alkyl;
$R^7$ is halogen, hydrogen, optionally substituted $C_{1-8}$ alkyl;
$R^8$ is halogen, hydrogen, optionally substituted $C_{1-8}$ alkyl;
$R^9$ is hydrogen or optionally substituted $C_{1-8}$ alkyl;
$R^{15}$ is hydrogen, optionally substituted $C_{1-8}$ alkyl or $O(C_{1-8}$ alkyl); and
with the proviso that the compound of Formula I is not of structures:

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is hydrogen, optionally substituted $C_{1-8}$ alkyl,

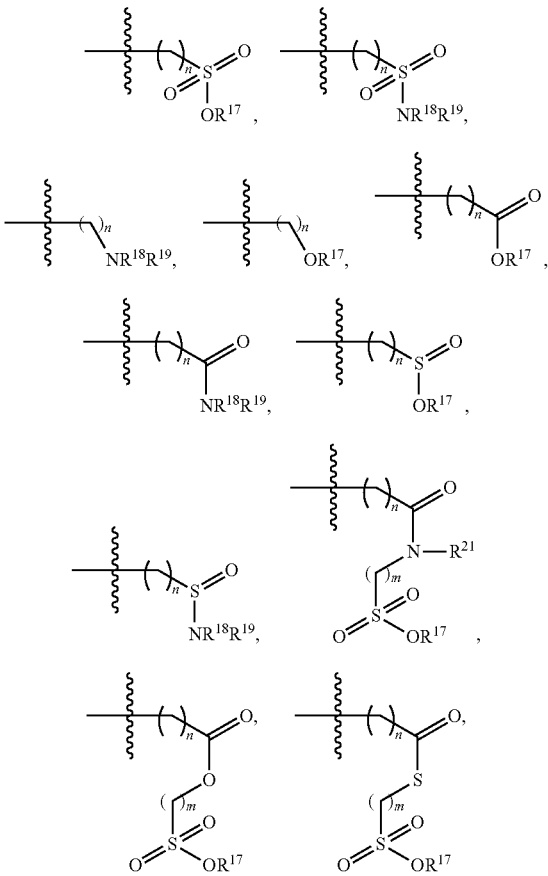

-continued

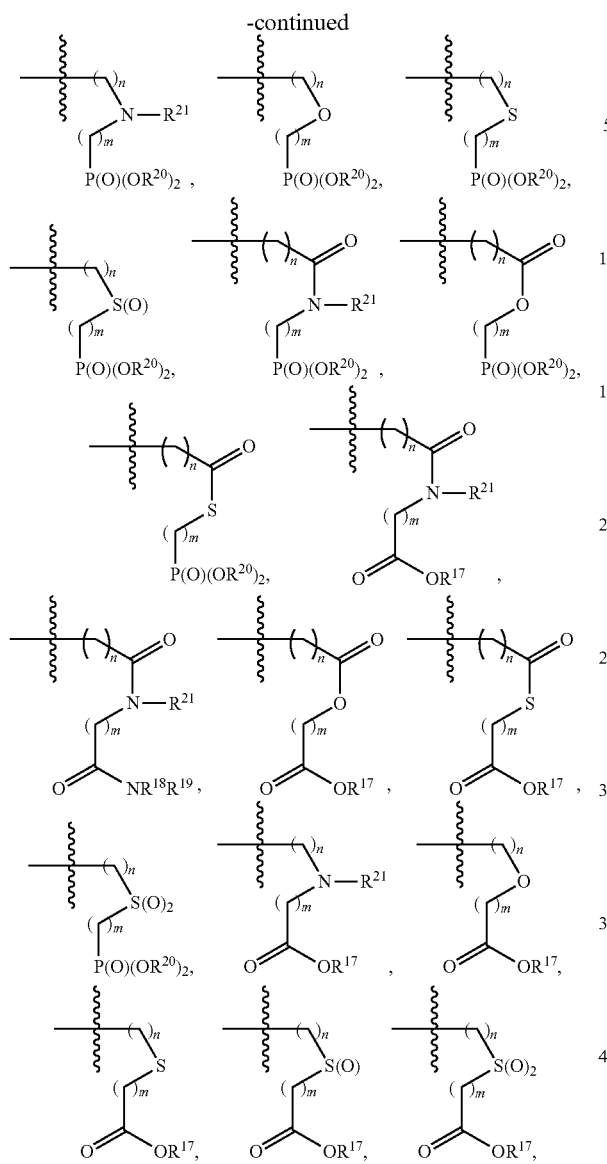

$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, C(O)($C_{1-8}$ alkyl) or optionally substituted $C_{1-8}$ alkyl;
$R^{15}$ is hydrogen, optionally substituted $C_{1-8}$ alkyl or O($C_{1-8}$ alkyl);
$R^{17}$ is hydrogen, optionally substituted $C_{6-10}$ aryl or optionally substituted $C_{1-8}$ alkyl;
$R^{18}$ is hydrogen, C(O)($C_{1-8}$ alkyl), optionally substituted $C_{6-10}$ aryl or optionally substituted $C_{1-8}$ alkyl;
$R^{19}$ is hydrogen, C(O)($C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5;
m is 1, 2, 3, 4, or 5; and with the proviso that the compound of Formula I is not of structures:

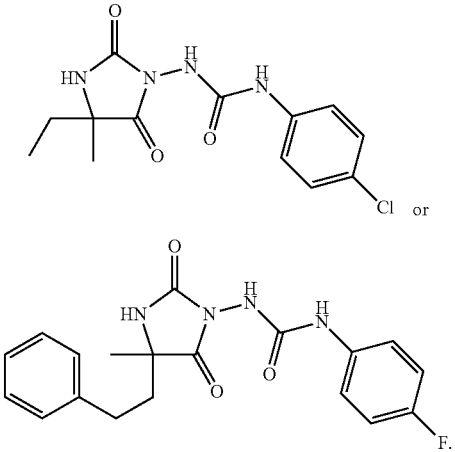 [SMILES: CCC1(C)NC(=O)N(NC(=O)Nc2ccc(Cl)cc2)C1=O ; CC1(CCc2ccccc2)NC(=O)N(NC(=O)Nc2ccc(F)cc2)C1=O]

In another aspect, the invention provides a compound having Formula I wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is hydrogen, optionally substituted $C_{1-8}$ alkyl,

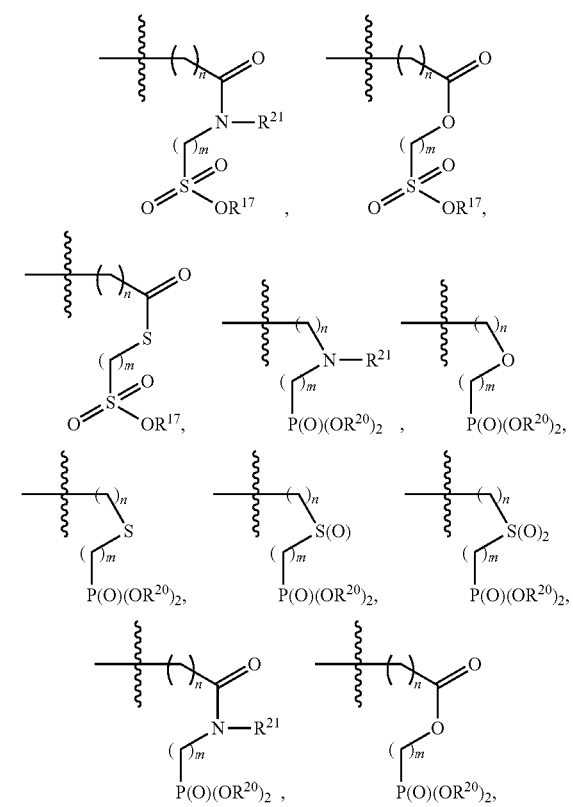

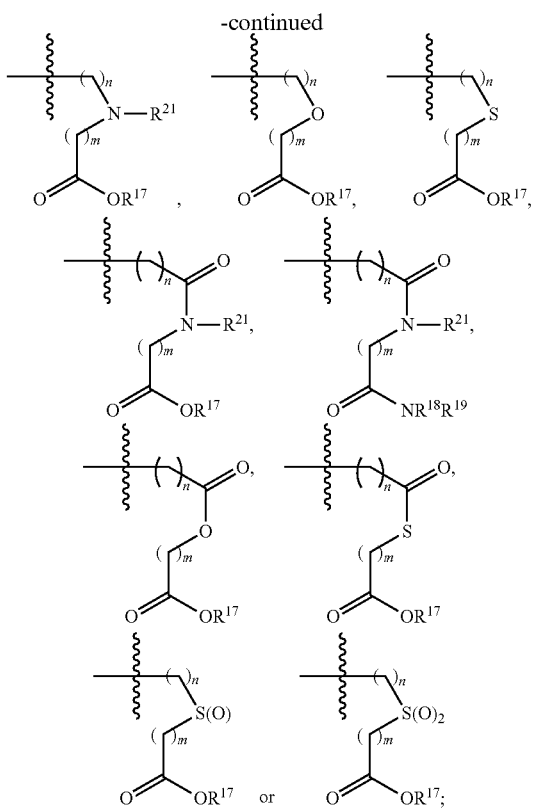

$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl);
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl), optionally substituted $C_{6-10}$ aryl or optionally substituted $C_{1-8}$ alkyl;
$R^{19}$ is hydrogen, $C(O)(C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5;
m is 1, 2, 3, 4, or 5; and
with the proviso that the compound of Formula I is not of structures:

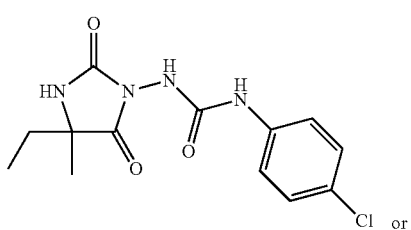

or

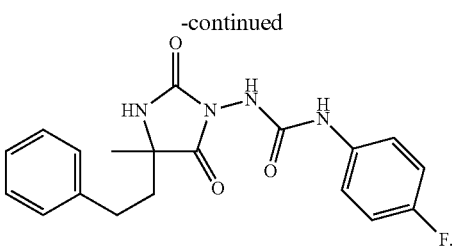

The term "alkyl", as used herein, refers to saturated, monovalent or divalent hydrocarbon moieties having linear or branched moieties or combinations thereof and containing 1 to 8 carbon atoms, unless otherwise specified. One methylene (—$CH_2$—) group, of the alkyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can be independently substituted by halogen atoms, hydroxyl groups, $C_{3-8}$ cycloalkyl groups, amino groups, heterocyclic groups, optionally substituted aryl groups, carboxylic acid groups, phosphonic acid groups, phosphonate groups, sulphonic acid groups, phosphoric acid groups, nitro groups, amide groups, ester groups, ether groups, ketone groups, sulfonamide groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. One methylene (—$CH_2$—) group, of the cycloalkyl can be replaced by oxygen, sulfur, sulfoxide, nitrogen, carbonyl, carboxyl, sulfonyl, sulfate, sulfonate, amide, sulfonamide, a divalent $C_{3-8}$ cycloalkyl, by a divalent heterocycle, or by a divalent aryl group. Cycloalkyl can be independently substituted by halogen atoms, sulfonyl($C_{1-8}$ alky) groups, sulfoxide($C_{1-8}$ alky) groups, sulfonamide groups, nitro groups, cyano groups, —$OC_{1-6}$ alkyl groups, —SH, —$SC_{1-6}$ alkyl groups, —$C_{1-6}$ alkyl groups, —$C_{2-6}$ alkenyl groups, —$C_{2-6}$ alkynyl groups, amide groups, ester groups, ether groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. One methylene (—$CH_2$—) group, of the cycloalkenyl can be replaced, by a divalent $C_{3-8}$ cycloalkyl, by a divalent heterocycle, or by a divalent aryl group. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amide groups, ester groups, ether groups, amino groups, aryl groups, sulfonamide groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected from oxygen, nitrogen, sulfur or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, sulfonamide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, amide groups, ester groups, ether groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms by removal of one hydrogen. Aryls can be monocyclic or polycyclic. One or more hydrogen atoms can be independently substituted by halogen atoms, sulfonyl($C_{1-6}$ alkyl) groups, sulfoxide($C_{1-6}$ alkyl) groups, sulfonamide groups, carboxylic acid groups, $C_{1-6}$ alkyl carboxylates (ester) groups, amide groups, nitro groups, cyano groups, —$OC_{1-6}$ alkyl groups, —SH, —$SC_{1-6}$ alkyl groups, —$C_{1-6}$ alkyl groups, —$C_{2-6}$ alkenyl groups, —$C_{2-6}$ alkynyl groups, ether groups, ketone groups, aldehydes groups, sulfonamide groups, alkylamino groups, ester groups, amino groups, aryl groups, $C_{3-8}$ cycloalkyl groups or hydroxyl groups.

The term "hydroxyl" as used herein, represents a group of formula "—OH".

The term "carbonyl" as used herein, represents a group of formula "—C(O)—".

The term "aldehyde" as used herein, represents a group of formula "—C(O)H".

The term "ketone" as used herein, represents a group of formula —C(O)$R^x$ wherein $R^x$ is alkyl, aryl, cycloalkyl, cycloalkenyl, heterocycle as defined above.

The term "ether" as used herein, represents a group of formula —(O)$R^x$ wherein $R^x$ is alkyl, aryl, cycloalkyl, cycloalkenyl, heterocycle as defined above.

The term "amine" as used herein, represents a group of formula "—$NR^xR^y$" wherein $R^x$ is alkyl, aryl, cycloalkyl, cycloalkenyl, heterocycle as defined above and $R^y$ is alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$-".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "ester" as used herein, represents a group of formula "—C(O)$OR^x$", wherein $R^x$ is alkyl, aryl, cycloalkyl, cycloalkenyl, heterocycle as defined above.

The term "nitro" as used herein, represents a group of formula "—$NO_2$".

The term "cyano" as used herein, represents a group of formula "—CN".

The term "amide" as used herein, represents a group of formula "—C(O)$NR^xR^y$," wherein $R^x$ and $R^y$ can be independently hydrogen, alkyl, aryl, cycloalkyl, cycloalkenyl, heterocycle as defined above.

The term "sulfonamide" as used herein, represents a group of formula "—S(O)$_2NR^xR^y$" wherein $R^x$ and $R^y$ can independently be hydrogen, alkyl, aryl, cycloalkyl, cycloalkenyl, heterocycle as defined above.

The term "sulfoxide" as used herein, represents a group of formula "—S(O)-".

The term "phosphonic acid" as used herein, represents a group of formula "—P(O)(OH)$_2$".

The term "phosphonate" as used herein, represents a group of formulae "—P(O)(OH)(O$C_{1-8}$ alkyl)" or "—P(O)(O$C_{1-8}$ alkyl)(O$C_{1-8}$ alkyl)".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Usually $R^1$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$. Preferred $R^1$ is halogen or hydrogen. More preferred $R^1$ is hydrogen or fluorine.

Usually $R^2$ is halogen, optionally substituted $C_{1-8}$ alkyl, $OR^9$, $C(O)R^{19}$, $CF_3$, $NO_2$, $NR^{13}R^{14}$, CN, $SR^{15}$ or $SO_2R^{16}$. Preferred $R^2$ is halogen, optionally substituted $C_{1-8}$ alkyl, $OR^9$, CN or $SR^{15}$. More preferred $R^2$ is chlorine, bromine, methoxy, $CF_3$, methyl, ethyl, cyano, thiomethyl.

Usually $R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a 5 or 6 member ring which is optionally substituted. Preferred $R^3$ is hydrogen or together with $R^5$ forms a 5 or 6 member ring which is optionally substituted. More preferred $R^3$ is hydrogen or together with $R^5$ forms a 6 member ring which is optionally substituted.

Usually $R^4$ is hydrogen, optionally substituted $C_{1-8}$ alkyl,

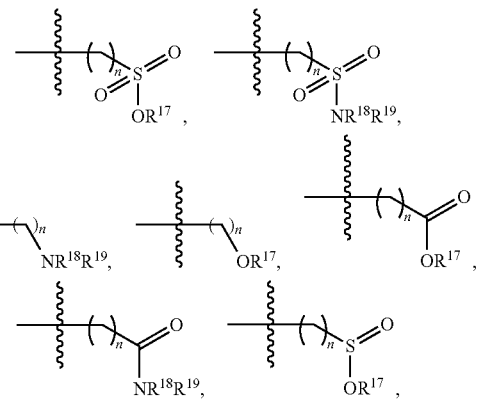

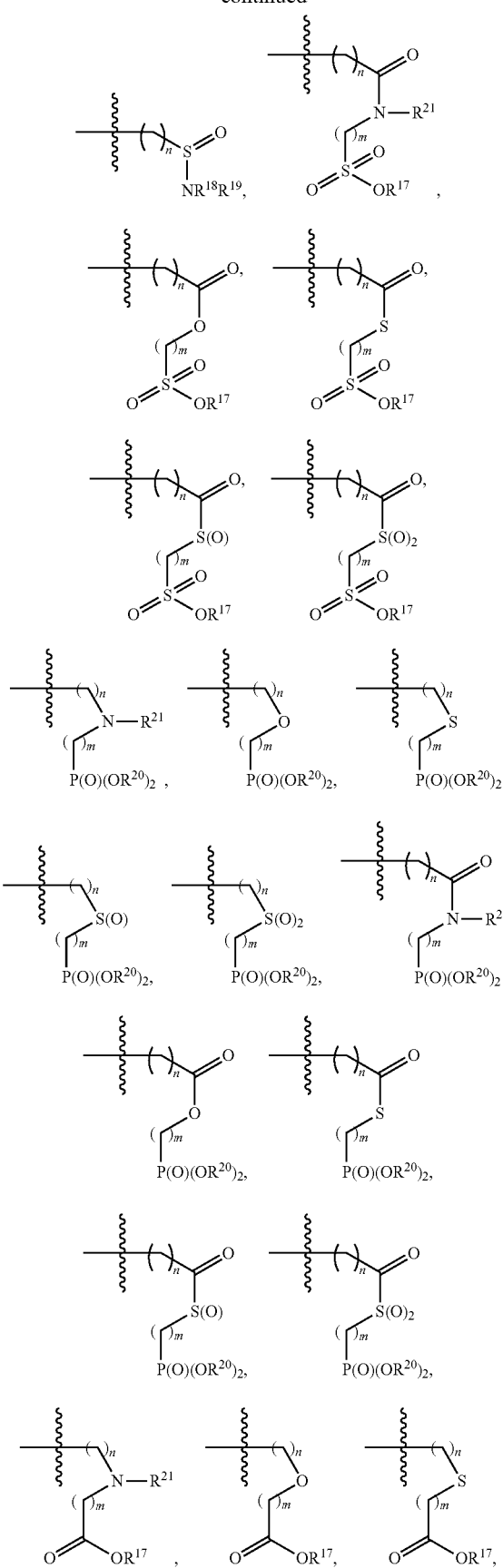

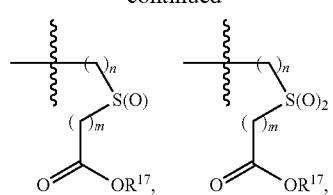

optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a spiro monocyclic or polycyclic, carbocyclic or heterocyclic, saturated or unsaturated 5 to 10 member ring which is optionally substituted. Preferred $R^4$ is optionally substituted $C_{1-8}$ alkyl, optionally substituted $C_{3-8}$ cycloalkyl or together with $R^5$ forms a spiro monocyclic or polycyclic, carbocyclic or heterocyclic, saturated or unsaturated 5 to 10 member ring which is optionally substituted.

More preferred $R^4$ is methyl, isopropyl, ethyl, cyclopropyl, isobutyl,

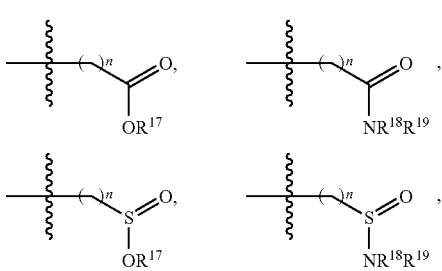

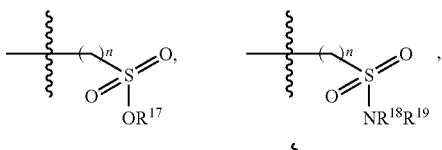

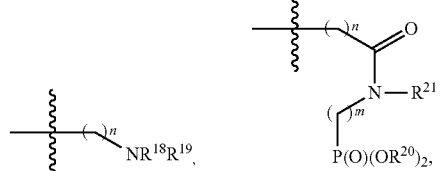

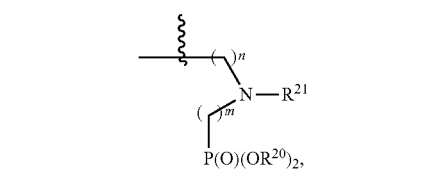

or together with $R^5$ forms a spiro monocyclic or polycyclic, carbocyclic, saturated or unsaturated 5 to 10 member ring. Most preferred $R^4$ is methyl, isopropyl, ethyl, cyclopropyl, isobutyl,

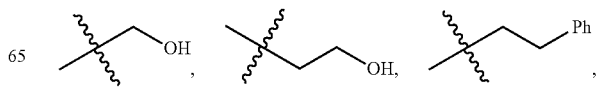

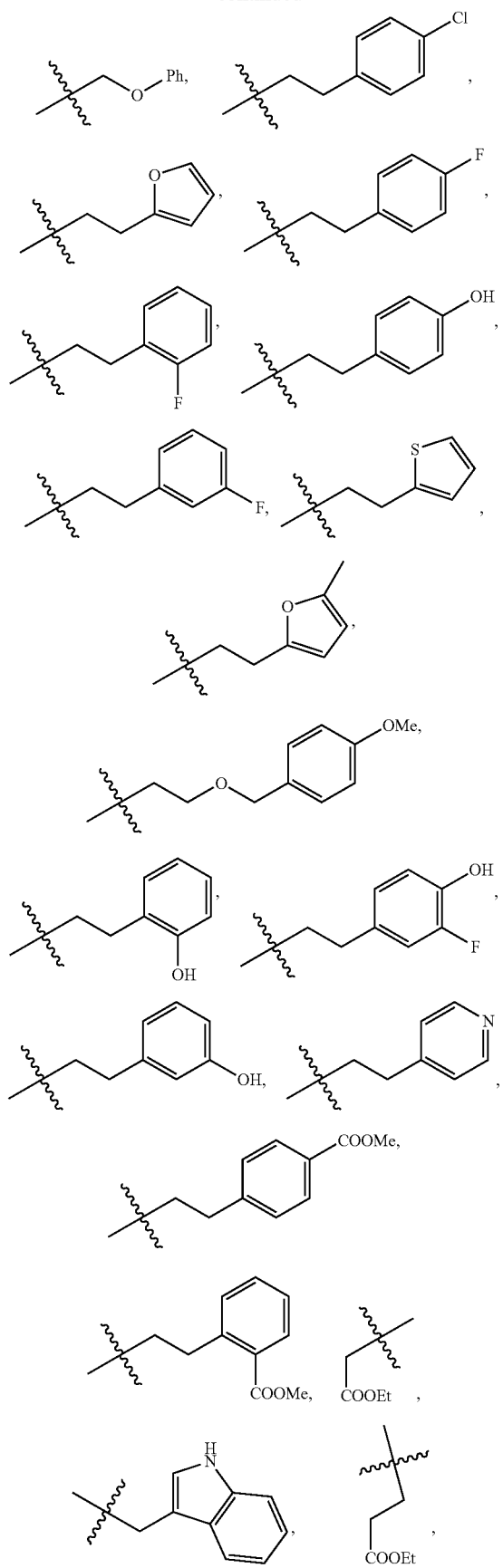
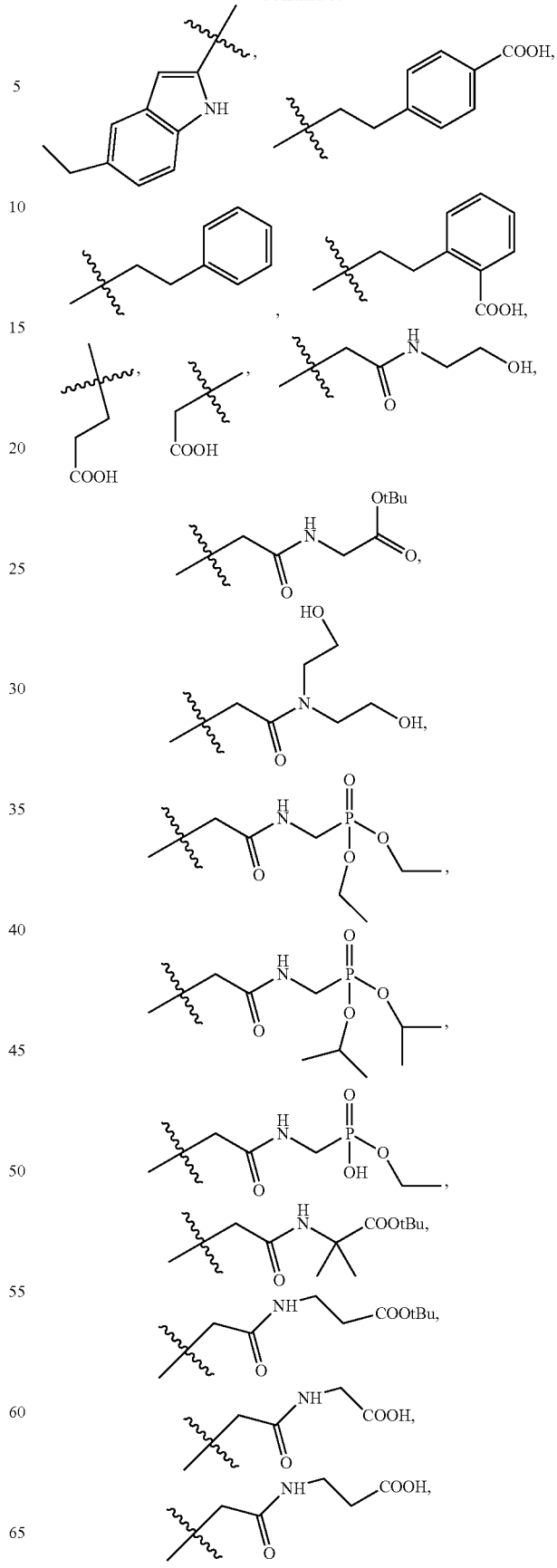

-continued or together with R[5] forms a spiro cyclopentyl or cyclohexyl monocyclic saturated carbocycle or a spiro polycyclic partially unsaturated 8 or 10 member ring such as 2,3-dihydro-1H-indene or 1,2,3,4-tetrahydronaphtalene.

Usually $R^5$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^4$ forms a spiro monocyclic or polycyclic carbocyclic or heterocyclic, saturated or unsaturated 5 to 10 member ring which is optionally substituted or together with $R^3$ forms a 5 or 6 member ring which is optionally substituted. Preferred $R^5$ is optionally substituted $C_{1-8}$ alkyl, optionally substituted $C_{3-8}$ cycloalkyl, optionally substituted heterocycle, or together with $R^4$ forms a spiro monocyclic or polycyclic carbocyclic or heterocyclic, saturated or unsaturated 5 to 10 member ring which is optionally substituted or together with $R^3$ forms a 5 or 6 member ring which is optionally substituted.

More preferred $R^5$ is methyl, ethyl, iso-propyl, iso-butyl, ethyl substituted with optionally substituted phenyl, ethyl substituted with optionally substituted furan, ethyl substituted with optionally substituted thiophene, optionally substituted indole, cyclopropyl, or together with $R^4$ forms a spiro cyclopenyl or cyclohexyl monocyclic saturated carbocycle or a spiro polycyclic partially unsaturated 8 or 10 member ring such as 2,3-dihydro-1H-indene or 1,2,3,4-tetrahydronaphtalene or forms a 6 member ring which is optionally substituted.

Usually $R^6$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$. Preferred $R^6$ is halogen or hydrogen. More preferred $R^6$ is fluorine or hydrogen.

Usually $R^7$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$. Preferred $R^7$ is hydrogen.

Usually $R^8$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$. Preferred $R^8$ is hydrogen.

Usually $R^9$ is hydrogen, $C(O)(C_{1-8}$ alkyl), or optionally substituted $C_{1-8}$ alkyl. Preferred $R^9$ is optionally substituted $C_{1-8}$ alkyl. More preferred $R^9$ is methyl.

Usually $R^{10}$ is hydrogen, optionally substituted $C_{1-8}$ alkyl, $O(C_{1-8}$ alkyl), $NR^{11}R^{12}$ or OH.

Usually $R^{11}$ is hydrogen, optionally substituted $C_{6-10}$ aryl or optionally substituted $C_{1-8}$ alkyl.

Usually $R^{12}$ is hydrogen, optionally substituted $C_{6-10}$ aryl or optionally substituted $C_{1-8}$ alkyl.

Usually $R^{13}$ is hydrogen, optionally substituted $C_{6-10}$ aryl or optionally substituted $C_{1-8}$ alkyl.

Usually $R^{14}$ is hydrogen, optionally substituted $C_{6-10}$ aryl, optionally substituted $C_{1-8}$ alkyl, $C(O)(C_{1-8}$ alkyl) or $SO_2(C_{1-8}$ alkyl).

Usually $R^{15}$ is hydrogen, optionally substituted $C_{1-8}$ alkyl or $O(C_{1-8}$ alkyl).

Usually $R^{16}$ is hydroxyl, $O(C_{1-8}$ alkyl), $(C_{1-8}$ alkyl) or $NR^{11}R^{12}$.

Usually $R^{17}$ is hydrogen, optionally substituted $C_{6-10}$ aryl or optionally substituted $C_{1-8}$ alkyl.

Preferred $R^{17}$ is hydrogen, methyl, ethyl, tert-butyl.

Usually $R^{18}$ is hydrogen, $C(O)(C_{1-8}$ alkyl), optionally substituted $C_{6-10}$ aryl or optionally substituted $C_{1-8}$ alkyl.

Preferred $R^{18}$ is hydrogen, methyl, ethyl, tert-butyl —$(CH_2)_n$—$(COOC_{1-8}$ alkyl), —$(CH_2)_n$—OH, —$(CH_2)_n$—P(O)(OC$_{1-8}$ alkyl)$_2$, —$(CH_2)_n$—P(O)(OH)(OC$_{1-8}$ alkyl), —$(CH_2)_n$—(COON), —$(CH_2)_n$—(CONH(C$_{1-8}$ alkyl)), —$(CH_2)_n$—(CONH$_2$), —$(CH_2)_n$—(CON(C$_{1-8}$ alkyl)(C$_{1-8}$ alkyl)), —$(CH_2)_n$—(SO$_3$H), —$(C(C_{1-8}$ alkyl)(C$_{1-8}$ alkyl))$_n$(COOC$_{1-8}$ alkyl), —$(C(C_{1-8}$ alkyl)(C$_{1-8}$ alkyl))$_n$(OH), —$(C(C_{1-8}$ alkyl)(C$_{1-8}$ alkyl))$_n$P(O)(OC$_{1-8}$ alkyl)$_2$, —$(C(C_{1-8}$ alkyl)(C$_{1-8}$ alkyl))$_n$P(O)(OH)(OC$_{1-8}$ alkyl), —$(O(C_{1-8}$ alkyl)(C$_{1-8}$ alkyl))$_n$(COOH), —$(O(C_{1-8}$ alkyl)(C$_{1-8}$ alkyl))$_n$(CONH(C$_{1-8}$ alkyl)), —$(C(C_{1-8}$ alkyl)(C$_{1-8}$ alkyl))$_n$(CONH$_2$), —$(C(C_{1-8}$ alkyl)(C$_{1-8}$ alkyl))$_n$(CON(C$_{1-8}$ alkyl)(C$_{1-8}$ alkyl)), —$(C(C_{1-8}$ alkyl)(C$_{1-8}$ alkyl))$_n$—(SO$_3$H), —$(CH(C_{1-8}$ alkyl))$_n$(COOC$_{1-8}$ alkyl), —$(CH(C_{1-8}$ alkyl))$_n$(OH), —$(CH(C_{1-8}$ alkyl))$_n$P(O)(OC$_{1-8}$ alkyl)$_2$, —$(CH(C_{1-8}$ alkyl))$_n$P(O)(OH)(OC$_{1-8}$ alkyl), —$(CH(C_{1-8}$ alkyl))$_n$(COOH), —$(CH(C_{1-8}$ alkyl))$_n$(CONH(C$_{1-8}$ alkyl)), —$(CH(C_{1-8}$ alkyl))$_n$(CONH$_2$), —$(CH(C_{1-8}$ alkyl))$_n$(CON(C$_{1-8}$ alkyl)(C$_{1-8}$ alkyl)), —$(CH(C_{1-8}$ alkyl))$_n$—(SO$_3$H).

More preferred $R^{18}$ is hydrogen, —$(CH_2)_2(OH)$, —$(CH_2)(COOtBu)$, —$(CH_2)(CONH_2)$, —$(C(CH_3)_2)(COOH)$, —$(C(CH_3)_2)(COOtBu)$, —$(CH_2)P(O)(OiPr)_2$, —$(CH_2)P(O)(OEt)_2$, —$(CH_2)P(O)(OH)(OEt)$, —$(CH_2)_2(COOtBu)$, —$(CH_2)_2(CONH_2)$, —$(C(CH_3)_2)(CH_2)(COOH)$, —$(C(CH_3)_2)(CH_2)(COOtBu)$, —$(CH_2)_2P(O)(OiPr)_2$, —$(CH_2)_2P(O)(OEt)_2$, or —$(CH_2)_2P(O)(OH)(OEt)$.

Usually $R^{19}$ is hydrogen, $C(O)(C_{1-8}$ alkyl), optionally substituted $C_{6-10}$ aryl or optionally substituted $C_{1-8}$ alkyl.

Preferred $R^{19}$ is hydrogen, methyl, ethyl, tert-butyl, —$(CH_2)_n$—$(COOC_{1-8}$ alkyl), —$(CH_2)_n$—OH, —$(CH_2)_n$—P(O)(OC$_{1-8}$ alkyl)$_2$, —$(CH_2)_n$—P(O)(OH)(OC$_{1-8}$ alkyl), —$(CH_2)_n$—(COON), —$(CH_2)_n$—(CONH(C$_{1-8}$ alkyl)), —$(CH_2)_n$—(CONH$_2$), —$(CH_2)_n$—(CON(C$_{1-8}$ alkyl)(C$_{1-8}$ alkyl)), —$(CH_2)_n$—(SO$_3$H), —$(C(C_{1-8}$ alkyl)(C$_{1-8}$ alkyl))$_n$(COOC$_{1-8}$ alkyl), —$(C(C_{1-8}$ alkyl)(C$_{1-8}$ alkyl))$_n$(OH), —$(C(C_{1-8}$ alkyl)(C$_{1-8}$ alkyl)), P(O)(OC$_{1-8}$ alkyl)$_2$, —$(O(C_{1-8}$ alkyl)(C$_{1-8}$ alkyl))$, P(O)(OH)(OC$_{1-8}$ alkyl), —$(C(C_{1-8}$ alkyl)(C$_{1-8}$ alkyl))$_n$(COOH), —$(C(C_{1-8}$ alkyl)(C$_{1-8}$ alkyl))$_n$(CONH(C$_{1-8}$ alkyl)), —$(C(C_{1-8}$ alkyl)(C$_{1-8}$ alkyl))$_n$(CONH$_2$), —$(C(C_{1-8}$ alkyl)(C$_{1-8}$ alkyl))$_n$(CON(C$_{1-8}$ alkyl)(C$_{1-8}$ alkyl)), —$(C(C_{1-8}$ alkyl)(C$_{1-8}$ alkyl))$, —(SO$_3$H), —$(CH(C_{1-8}$ alkyl))$_n$(COOC$_{1-8}$ alkyl), —$(CH(C_{1-8}$ alkyl))$_n$(OH), —$(CH(C_{1-8}$ alkyl)), P(O)(OC$_{1-8}$ alkyl)$_2$, —$(CH(C_{1-8}$ alkyl)), P(O)(OH)(OC$_{1-8}$ alkyl), —$(CH(C_{1-8}$ alkyl))$_n$(COOH), —$(CH(C_{1-8}$ alkyl))$_n$(CONH(C$_{1-8}$ alkyl)), —$(CH(C_{1-8}$ alkyl))$_n$(CONH$_2$), —$(CH(C_{1-8}$ alkyl))$_n$(CON(C$_{1-8}$ alkyl)(C$_{1-8}$ alkyl)), —$(CH(C_{1-8}$ alkyl))$_n$—(SO$_3$H).

Preferred $R^{19}$ is hydrogen, methyl, ethyl, tert-butyl.

Usually $R^{20}$ is hydrogen, optionally substituted $C_{6-10}$ aryl or optionally substituted $C_{1-8}$ alkyl. Preferred $R^{20}$ is hydrogen, methyl, ethyl, tert-butyl.

Usually $R^{21}$ is hydrogen, optionally substituted $C_{6-10}$ aryl or optionally substituted $C_{1-8}$ alkyl. Preferred $R^{21}$ is hydrogen, methyl, ethyl, tert-butyl.

Usually n is 1, 2, 3, 4, or 5. Preferred n is 1, 2 or 3. Most preferred n is 1 or 2.

Usually m is 1, 2, 3, 4, or 5. Preferred m is 1, 2 or 3. Most preferred m is 1 or 2.

Compounds of the invention are:

1-(4-Bromophenyl)-3-(4,4-diethyl-2,5-dioxoimidazolidin-1-yl)urea;
1-(4-Chlorophenyl)-3-(4,4-diethyl-2,5-dioxoimidazolidin-1-yl)urea;
1-(4-Methoxyphenyl)-3-(4,4-diethyl-2,5-dioxoimidazolidin-1-yl)urea;
1-(4-Ethylphenyl)-3-(4,4-diethyl-2,5-dioxoimidazolidin-1-yl)urea;
1-(4-Cyanophenyl)-3-(4,4-diethyl-2,5-dioxoimidazolidin-1-yl)urea;
1-(4-Bromo-2-fluorophenyl)-3-(4,4-diethyl-2,5-dioxoimidazolidin-1-yl)urea;
1-(4-Methylphenyl)-3-(4,4-diethyl-2,5-dioxoimidazolidin-1-yl)urea;
1-(4-Methylthiophenyl)-3-(4,4-diethyl-2,5-dioxoimidazolidin-1-yl)urea;
1-(4-Bromophenyl)-3-(4-methyl-2,5-dioxo-4-phenethylimidazolidin-1-yl)urea;
1-(4-Bromophenyl)-3-(2,4-dioxo-1,3-diazaspiro[4.4]nonan-3-yl)urea;
1-(4-Bromo-2-fluorophenyl)-3-(2,4-dioxo-1,3-diazaspiro[4.4]nonan-3-yl)urea;
1-(4-Bromophenyl)-3-(4,4-dimethyl-2,5-dioxoimidazolidin-1-yl)urea;
1-(4-Bromophenyl)-3-(2,5-dioxo-1',3'-dihydrospiro[imidazolidine-4,2'-inden]-1-yl)urea;
1-(4-Bromophenyl)-3-(2,4-dioxo-1,3-diazaspiro[4.5]decan-3-yl)urea;
1-(4-Bromo-2-fluorophenyl)-3-(2,4-dioxo-1,3-diazaspiro[4.5]decan-3-yl)urea;
1-(4-Chloro-2-fluorophenyl)-3-(4,4-diethyl-2,5-dioxoimidazolidin-1-yl)urea;
1-(4-Bromo-2-fluorophenyl)-3-(4-methyl-2,5-dioxo-4-phenethylimidazolidin-1-yl)urea;
1-(4-Bromophenyl)-3-(4-ethyl-4-isopropyl-2,5-dioxoimidazolidin-1-yl)urea;
1-(4-Chloro-3-fluorophenyl)-3-(4,4-diethyl-2,5-dioxoimidazolidin-1-yl)urea;
1-(4-Bromo-2-fluorophenyl)-3-(4-ethyl-4-isopropyl-2,5-dioxoimidazolidin-1-yl)urea;
1-(2,4-Dioxo-1,3-diazaspiro[4,5]decan-3-yl)-3-(4-methoxypheynyl)urea;
(S)-1-(4-Bromophenyl)-3-(1,3-dioxo-10,10a-dihydroimidazo[1,5-b]isoquinolin-2(1H,3H,5H)-yl)urea;
(S)-1-(4-Bromo-2-fluorophenyl)-3-(1,3-dioxo-10,10a-dihydroimidazo[1,5-b]isoquinolin-2(1H,3H,5H)-yl)urea;
1-(4-Bromo-2-fluorophenyl)-3-(2,5-dioxo-1',3'-dihydrospiro[imidazolidine-4,2'-inden]-1-yl)urea;
1-(4-Bromophenyl)-3-(4-methyl-2,5-dioxo-4-(phenoxymethyl)imidazolidin-1-yl)urea;
1-(4-Bromo-2-fluorophenyl)-3-(2,5-dioxo-3',4'-dihydro-1'H-spiro[imidazolidine-4.2°naphthalen-1-yl)urea;
1-(4-Bromo-2-fluorophenyl)-3-(2,5-dioxo-3',4'-dihydro-1'H-spiro[imidazolidine-4.2°naphthalen-1-yl)urea;
1-(4-Bromo-2-fluorophenyl)-3-(4-methyl-2,5-dioxo-4-(phenoxymethyl)imidazolidin-1-yl)urea;
1-(4-Bromo-2-fluorophenyl)-3-(4-ethyl-2,5-dioxo-4-(phenethyl)imidazolidin-1-yl)urea;
1-(4-Bromophenyl)-3-(4-ethyl-2,5-dioxo-4-(phenethyl)imidazolidin-1-yl)urea;
1-(4-Bromophenyl)-3-(4-isobutyl-2,5-dioxo-4-phenethyl)imidazolidin-1-yl)urea;
1-(4-Bromo-2-fluorophenyl)-3-(4-isobutyl-2,5-dioxo-4-phenethyl)imidazolidin-1-yl)urea;
1-(4-Bromophenyl)-3-(4-(4-chlorophenethyl)-4-methyl-2,5-dioxoimidazolidin-1-yl)urea;
1-(4-Bromo-2-fluorophenyl)-3-(4-chlorophenethyl)-4-methyl-2,5-dioxo-imidazolidin-1-yl)urea;
1-(4-Bromophenyl)-3-(4-(2-furan-2-yl)ethyl)-4-methyl-2,5-dioxoimidazolidin-1-yl)urea;
1-(4-Bromo-2-fluorophenyl)-3-(4-(2-furan-2-yl)ethyl)-4-methyl-2,5-dioxoimidazolidin-1-yl)urea;
1-(4-Bromophenyl)-3-(4-(2-fluorophenethyl)-4-methyl-2,5-dioxoimidazolidin-1-yl)urea;
1-(4-Bromo-2-fluorophenyl)-3-(4-(2-fluorophenethyl)-4-methyl-2,5-dioxoimidazolidin-1-yl)urea;
1-(4-Bromophenyl)-3-(4-(4-fluorophenethyl)-4-methyl-2,5-dioxoimidazolidin-1-yl)urea;
1-(4-Bromo-2-fluorophenyl)-3-(4-(4-fluorophenethyl)-4-methyl-2,5-dioxoimidazolidin-1-yl)urea;
1-(4-Bromophenyl)-3-(4-(3-fluorophenethyl)-4-methyl-2,5-dioxoimidazolidin-1-yl)urea;
1-(4-Bromophenyl)-3-(4-(4-hydroxyphenethyl)-4-methyl-2,5-dioxoimidazolidin-1-yl)urea;
1-(4-Bromophenyl)-3-(4-methyl-2,5-dioxo-4-(2-thiophen-2-yl)ethyl)imidazolidin-1-yl)urea;
1-(4-Bromo-2-fluorophenyl)-3-(4-methyl-2,5-dioxo-4-(2-thiophen-2-yl)ethyl)imidazolidin-1-yl)urea;
1-(4-Bromo-2-fluorophenyl)-3-(4-(4-hydroxyphenethyl)-4-methyl-2,5-dioxoimidazolidin-1-yl)urea;
1-(4-Bromophenyl)-3-(4-methyl-4-(2-(5-methylfuran-2-yl)ethyl)2,5-dioxoimidazolidin-1-yl)urea;
1-(4-Bromophenyl)-3-(4-(3-fluoro-4-hydroxyphenethyl)-4-methyl-2,5-dioxoimidazolidin-1-yl)urea;
1-(4-Bromophenyl)-3-(4-(3-fluoro-4-hydroxyphenethyl)-4-methyl-2,5-dioxoimidazolidin-1-yl)urea;
1-(4-Bromophenyl)-3-(4-isopropyl-4-(2-((4-methoxybenzyl)oxy)ethyl)-2,5-dioxoimidazolidin-1-yl)urea;
1-(4-Bromophenyl)-3-(4-(2-hydroxyphenethyl)-4-methyl-2,5-dioxoimidazolidin-1-yl)urea;
1-(4-Bromo-2-fluorophenyl)-3-(4-(2-hydroxyphenethyl)-4-methyl-2,5-dioxoimidazolidin-1-yl)urea;
1-(4-Bromophenyl)-3-(4-(3-hydroxyphenethyl)-4-methyl-2,5-dioxoimidazolidin-1-yl)urea;
1-(4-Bromo-2-fluorophenyl)-3-(4-(3-hydroxyphenethyl)-4-methyl-2,5-dioxoimidazolidin-1-yl)urea;
1-(4-Bromophenyl)-3-(4-methyl-2,5-dioxo-4-(2-(pyridin-4-yl)ethyl)imidazolidin-1-yl)urea;
1-(4-Bromo-2-fluorophenyl)-3-(4-methyl-2,5-dioxo-4-(pyridin-4-yl)ethyl)imidazolidin-1-yl)urea;
1-(4-Bromophenyl)-3-(4-isopropyl-4-(((4-methoxybenzyl)oxy)methyl)-2,5-dioxoimidazolidin-1-yl)urea;
1-(4-Bromo-2-fluorophenyl)-3-(4-isopropyl-4-(((4-methoxybenzyl)oxy)methyl)-2,5-dioxoimidazolidin-1-yl)urea;
Methyl 4-(2-(1-(3-(4-Bromophenyl)ureido)-4-methyl-2,5-dioxoimidazolidin-4-yl)ethyl)benzoate;
Methyl 2-(2-(1-(3-(4-bromophenyl)ureido)-4-methyl-2,5-dioxoimidazolidin-4-yl)ethyl)benzoate;
Methyl 2-(2-(1-(3-(4-bromophenyl)ureido)-4-ethyl-2,5-dioxoimidazolidin-4-yl)ethyl)benzoate;

Methyl 2-(2-(1-(3-(4-bromo-2-fluorophenyl)ureido)-4-ethyl-2,5-dioxoimidazolidin-4-yl)ethyl)benzoate;
Ethyl 2-(1-(3-(4-bromo-2-fluorophenyl)ureido)-4-isopropyl-2,5-dioxoimidazolidin-4-yl)acetate;
Ethyl 2-(1-(3-(4-bromophenyl)ureido)-4-isopropyl-2,5-dioxoimidazolidin-4-yl)acetate;
1-(4-Bromophenyl)-3-[4-(1H-indol-3-ylmethyl)-4-methyl-2,5-dioxoimidazolidin-1-yl]urea;
1-(4-Bromo-2-fluorophenyl)-3-[4-(5-ethyl-1H-indol-2-yl)-4-methyl-2,5-dioxoimidazolidin-1-yl]urea;
1-(4-Bromophenyl)-3-(4,4-dicyclopropyl-2,5-dioxoimidazolidin-1-yl)urea;
1-(4-Bromophenyl)-3-[2,5-dioxo-4,4-di(propan-2-yl)imidazolidin-1-yl]urea;
Ethyl-3-[1-{[(4-bromophenyl)carbamoyl]amino}-2,5-dioxo-4-(propan-2-yl)imidazolidin-4-yl]propanoate;
1-(4-Bromophenyl)-3-(4,4-dimethyl-2,5-dioxo-3-phenylimidazolidin-1-yl)urea;
(−)-1-(4-Bromophenyl)-3-(4-methyl-2,5-dioxo-4-phenethylimidazolidin-1-yl)urea;
(+)-1-(4-Bromophenyl)-3-(4-methyl-2,5-dioxo-4-phenethylimidazolidin-1-yl)urea;
(+)-1-(4-Bromophenyl)-3-(4-ethyl-4-isopropyl-2,5-dioxoimidazolidin-1-yl)urea;
(−)-1-(4-Bromophenyl)-3-(4-ethyl-4-isopropyl-2,5-dioxoimidazolidin-1-yl)urea;
1-(4-Bromophenyl)-3-(4-(hydroxymethyl)-4-isopropyl-2,5-dioxoimidazolidin-1-yl)urea;
1-(4-Bromophenyl)-3-(4-(2-hydroxyethyl)-4-isopropyl-2,5-dioxoimidazolidin-1-yl)urea;
1-(4-Bromo-2-fluorophenyl)-3-(4-(2-hydroxymethyl)-4-isopropyl-2,5-dioxoimidazolidin-1-yl)urea;
4-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-ethyl-2,5-dioxoimidazolidin-4-yl)ethyl)benzoic acid;
Methyl 2-(2-(1-(3-(4-bromo-2-fluorophenyl)ureido)-4-ethyl-2,5-dioxoimidazolidin-4-yl)ethyl)benzoate;
2-(1-(3-(4-Bromophenyl)ureido)-4-isopropyl-2,5-dioxoimidazolidin-4-yl)acetic acid;
2-(1-(3-(4-Bromo-2-fluorophenyl)ureido)-4-isopropyl-2,5-dioxoimidazolidin-4-yl)acetic acid;
3-[1-{[(4-bromophenyl)carbamoyl]amino}-2,5-dioxo-4-(propan-2-yl)imidazolidin-4-yl]propanoic acid;
3-(2-(1-(3-(4-Bromophenyl)ureido)-4-isopropyl-2,5-dioxoimidazolidin-4-yl)acetamido)propanoic acid;
2-(1-(3-(4-Bromophenyl)ureido)-4-isopropyl-2,5-dioxoimidazolidin-4-yl)-N-(2-hydroxyethyl)acetamide;
tert-Butyl 2-(2-(1-(3-(4-bromophenyl)ureido)-4-isopropyl-2,5-dioxoimidazolidin-4-yl)acetamido)acetate;
Diethyl((2-(1-(3-(4-bromophenyl)ureido)-4-isopropyl-2,5-dioxoimidazolidin-4-yl)acetamido)methyl)phosphonate;
2-(1-(3-(4-Bromophenyl)ureido)-4-isopropyl-2,5-dioxoimidazolidin-4-yl)-N,N-bis(2-hydroxyethyl)acetamide;
Diisopropyl((2-(1-(3-(4-bromophenyl)ureido)-4-isopropyl-2,5-dioxoimidazolidin-4-yl)acetamido)methyl)phosphonate;
Ethyl hydrogen((2-(1-(3-(4-bromophenyl)ureido)-4-isopropyl-2,5-dioxoimidazolidin-4-yl)acetamido)methyl)phosphonate;
tert-Butyl 2-(2-(1-(3-(4-bromophenyl)ureido)-4-isopropyl-2,5-dioxoimidazolidin-4-yl)acetamido)-2-methylpropanoate;
tert-Butyl 3-(2-(1-(3-(4-bromophenyl)ureido)-4-isopropyl-2,5-dioxoimidazolidin-4-yl)acetamido)propanoate;
2-(2-(1-(3-(4-Bromophenyl)ureido)-4-isopropyl-2,5-dioxoimidazolidin-4-yl)acetamido)acetic acid;
3-(2-(1-(3-(4-Bromophenyl)ureido)-4-isopropyl-2,5-dioxoimidazolidin-4-yl)acetamido)propanoic acid;
2-(1-(3-(4-Bromo-2-fluorophenyl)ureido)-4-isopropyl-2,5-dioxoimidazolidin-4-yl)-N-(2-hydroxyethyl)acetamide;
2-(2-(1-(3-(4-Bromophenyl)ureido)-4-isopropyl-2,5-dioxoimidazolidin-4-yl)acetamido)-2-methylpropanoic acid;
N-(2-Amino-2-oxoethyl)-2-(1-(3-(4-bromophenyl)ureido)-4-isopropyl-2,5-dioxoimidazolidin-4-yl)acetamide.

Some compounds of Formula I and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal & Camille G. Wermuth (Eds), Verlag Helvetica Chemica Acta—Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta—Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor.

Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor like-1 receptor modulation: including, but not limited to the treatment of ocular inflammatory diseases: wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made.

Scheme 1

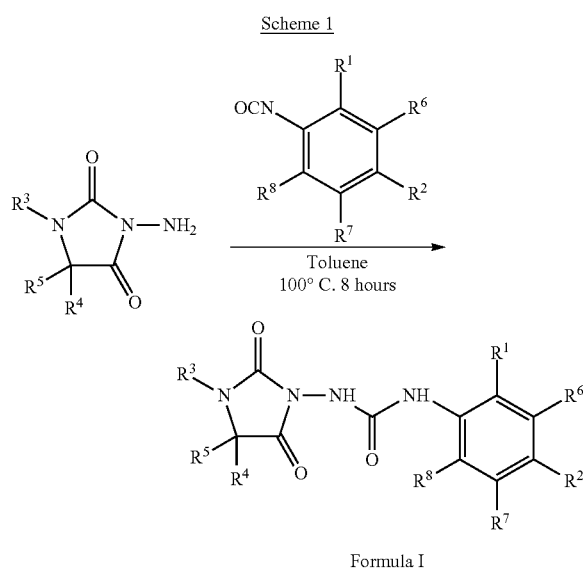

Formula I

Compounds within the scope of the invention may be prepared as depicted in Scheme 1. In general, a 3-amino-2,4-Imidazolidinedione, can be reacted with a phenylisocyanate in toluene at 100° C. to provide compounds of Formula I. At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 12.5; some intermediates' and reagents' names used in the examples were generated with softwares such as Chem Bio Draw Ultra version 12.0, ACD version 12.5 or Auto Nom 2000 from MDL ISIS Draw 2.5 SP1.

In general, characterization of the compounds was performed using NMR spectra, which were recorded on 300 or 600 MHz Varian and acquired at room temperature. Chemical shifts are given in ppm referenced either to internal TMS or to the solvent signal. The optical rotation was recorded on Perkin Elmer Polarimeter 341, 589 nm at 20° C., Na/Hal lamp.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on Teledyne-ISCO CombiFlash with a silica column, unless noted otherwise.

Enantiomers of racemic compounds were separated by chiral stationary phase high pressure liquid chromatography.

The following abbreviations are used in the examples:

| | |
|---|---|
| $Et_3N$ | triethylamine |
| THF | tertrahydrofuran |
| h | hours |
| DEA | diethanolamine |
| $CF_3CO_2H$ | trifluoroacetic acid |
| $MgSO_4$ | magnesium sulfate |
| $CH_2Cl_2$ | dichloromethane |
| EtOAc | ethyl acetate |
| $NaHCO_3$ | sodium bicarbonate |
| $CDCl_3$ | deuterated chloroform |
| MeOH | methanol |
| $CD_3OD$ | deuterated methanol |
| HCl | hydrochloric acid |
| $(NH_4)_2CO_3$ | ammonium carbonate |
| KCN | potassium cyanide |
| $K_2CO_3$ | potassium carbonate |
| DMSO | dimethylsulfonamide |
| $Pd(OAc)_2$ | palladium acetate |
| DDQ | 2,3-dichloro-5,6-dicyanobenzoqu none |
| RT | room temperature |
| i-PrMgCl-THF | Isopropylmagnesium chloride in tetrahydrofuran |
| EtOH | ethanol |
| DMF | dimethylformamide |
| $NH_3$ | ammonium |
| KOH | potassium hydroxide |
| DMAP | 4-Dimethylaminopyridine |
| LiOH | lithium hydroxide |
| $ClCO_2Et$ | ethylchloroformate |

The following synthetic procedures illustrate how compounds according to the invention can be made. Those skilled in the art will be routinely able to modify and/or adapt the following schemes to synthesize any compound of the invention covered by Formula I.

Example 1

Intermediate 1 tert-Butyl (2,5-Dioxo-1',3'-dihydrospiro[imidazolidine-4,2'-inden]-1-yl)carbamate

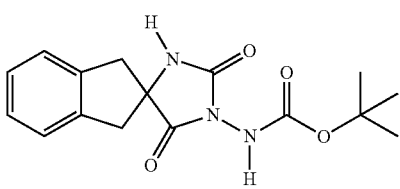 [SMILES: CC(C)(C)OC(=O)NN1C(=O)NC2(Cc3ccccc3C2)C1=O]

To a solution of, di-1H-imidazol-1-yl-methanone CAS 530-62-1 (486 mg, 3 mmol) in dioxane (10 mL) was added a solution of 1,1-dimethylethyl ester hydrazinecarboxylic acid, CAS 870-46-2 (330 mg, 2.5 mmol) in dioxane (10 mL) and stirred for 90 min at ambient temperature. Then, 2-amino-2,3-dihydro-1H-indene-2-carboxylic acid methyl ester, CAS 199330-64-8 (570 mg, 2.5 mmol) was added as solid to the reaction, immediately followed by $Et_3N$ (505 mg, 5 mmol). The reaction was then heated to 65° C. for 4 h. The reaction mixture was concentrated to ~15 mL, and allowed to settle at ambient temperature. Intermediate 1 separated as a white solid and was collected by filtration.

$^1$HNMR (CDCl$_3$): δ1.50 (s, 9H), 3.16 (br d, J=15 Hz, 2H), 3.69 (d, J=15 Hz, 2H), 7.23 (br s, 4H).

Example 2

Intermediate 2

1-Amino-1',3'-dihydrospiro[imidazolidine-4,2'-inden]-1-yl)-2,5-dione

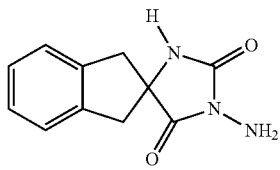 [SMILES: NN1C(=O)NC2(Cc3ccccc3C2)C1=O]

To a cold (−78° C.) Intermediate 1 (300 mg, 0.94 mmol) was added $CF_3CO_2H$ (3 mL). Then the cooling bath was removed and the stirred reaction mixture was allowed to warm at ambient temperature. After 30 min. all the $CF_3CO_2H$ was removed and the crude mixture was quenched by aq. NaHCO$_3$ until alkaline. The mixture was extracted with $CH_2Cl_2$ (2×30 mL). The organic layers were combined and dried with MgSO$_4$, and filtered and the solvent was removed under reduced pressure. Intermediate 2 was isolated.

$^1$HNMR (CD$_3$OD): δ 3.10 (d, J=16.2 Hz, 2H), 3.51 (d, J=16.2 Hz, 2H), 7.19-7.25 (m, 4H).

Example 3

Intermediate 3

1-((4-Methoxybenzyl)oxy)-4-methylpentan-3-one

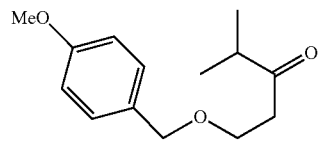 [SMILES: COc1ccc(COCCC(=O)C(C)C)cc1]

To a cold solution (0° C.) of 1-hydroxy-4-methylpentan-3-one CAS 132350-33-5 (580 mg, 5 mmol) in CH$_2$Cl$_2$ (8 mL) was added camphor sulfonic acid (58 mg) followed by a solution of 4-methoxybenzyl-2,2,2-trichloroacetimidate CAS 89238-99-3 (1.42 g, 5 mmol) in CH$_2$Cl$_2$ (8 mL) was added and stirred at RT for 16 h. The reaction was quenched by adding aq. NaHCO$_3$ (10 mL), extracted with CH$_2$Cl$_2$ (30 mL). The organic layer was dried (MgSO$_4$) and solvent removed under reduced pressure. The crude product was purified by silicagel chromatography using EtOAc in Hexane as eluent. Intermediate 3 was isolated as a colorless oil.

$^1$HNMR (CDCl$_3$): δ 1.10 (d, J=6.9 Hz, 6H), 2.50-2.67 (m, 1H), 2.74 (t, J=6.6 Hz, 2H), 3.71 (t, J=6.6 Hz, 2H), 3.80 (s, 3H), 4.44 (s, 2H), 6.84-6.89 (m, 2H), 7.21-7.27 (m, 2H

Example 4

Intermediate 4

1-((4-Methoxybenzyl)oxy)-3-methylbutan-2-one

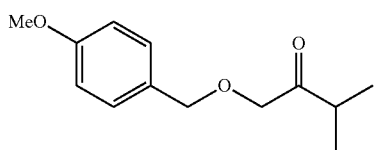 [SMILES: COc1ccc(COCC(=O)C(C)C)cc1]

To a cold (−78° C.) solution of N-methoxy-2-((4-methoxybenzyl)oxy)-N-methylacetamide CAS 191731-32-5 (856 mg, 3.6 mmol) in THF (10 mL) was added i-PrMgCl-THF solution. Then the reaction was warmed to RT, and stirred for 2 h, The reaction mixture was poured into cold 2N HCl and extracted with EtOAc, the organic layer was dried (MgSO$_4$) and solvent removed under reduced pressure. The crude mixture was purified by silicagel chromatography using EtOAc in hexane. Intermediate 4 was isolated as a colorless oil.

$^1$HNMR (CDCl$_3$): δ 1.08 (d, J=6.7 Hz, 6H), 2.70-2.91 (m, 1H), 3.80 (s, 3H), 4.10 (s, 2H), 4.52 (s, 2H), 6.88 (d, J=8.8 Hz, 2H), 7.28 (d, J=8.8 Hz, 2H).

Example 5

Intermediate 5

5-iso-Propyl-5-(2-((4-methoxybenzyl)oxy)ethyl)imidazolidine-2,4-dione

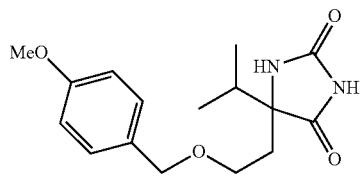 [SMILES: COc1ccc(COCCC2(C(C)C)NC(=O)NC2=O)cc1]

A mixture of Intermediate 3 1.82 g, 10 mmol), $(NH_4)_2CO_3$ (4.24 g, 40 mmol), KCN (2.5 g, 37.5 mmol) and EtOH (20 mL) was heated to 60° C. for 15 h. The crude mixture was filtered through a short celite column. Then the solvent was removed under reduced pressure and Intermediate 5 was isolated as a solid.

$^1$HNMR (CDCl$_3$): δ 0.94 (d, J=4.2 Hz, 3H), 0.96 (d, J=4.2 Hz, 3H), 1.90-2.21 (m, 3H), 3.41-3.60 (m, 2H), 3.78 (s, 3H), 4.34 (d, J=8.4 Hz, 1H), 4.38 (d, J=8.4 Hz, 1H), 6.80-6.90 (m, 2H), 7.20-7.27 (m, 2H).

Intermediates 6 through 10 were prepared in a similar manner to the procedure described in Example 5 for Intermediate 5. The starting materials used and the results are tabulated below in Table 1.

TABLE 1

| Interm. No. | IUPAC name Structure | Starting material | $^1$H NMR δ (ppm) |
|---|---|---|---|
| 6 | 5-(4-Bromophenethyl)-5-methylimidazolidine-2,4-dione | 4-(4-bromophenyl)butan-2-one CAS 89201-84-3 | $^1$HNMR (CD$_3$OD): δ 1.36 (s, 3H), 1.78-1.87 (m, 1H), 1.90-2.02 (m, 1H), 2.38-2.45 (m, 1H), 2.58-2.65 (m, 1H), 7.10 (d, J = 7.8 Hz, 2H), 7.38 (d, J = 7.8 Hz, 2H). |
| 7 | 5-(2-Bromophenethyl)-5-methylimidazolidine-2,4-dione | 4-(2-bromophenyl)butan-2-one CAS 3506-68-1 | $^1$HNMR (CD$_3$OD): δ 1.42 (s, 3H), 1.84-1.92 (m, 1H), 1.99-2.07 (m, 1H), 2.58-2.66 (m, 1H), 2.80-2.88 (m, 1H), 7.02-7.10 (m, 1H), 7.22-7.28 (m, 2H), 7.52 (dd, J = 7.8, 1.2 Hz, 1H). |
| 8 | Ethyl-2-(4-isopropyl-2,5-dioxoimidazolidin-4-yl)acetate | ethyl 4-methyl-3-oxopentanoate CAS 7152-15-0 | $^1$HNMR (DMSO-d$_6$): δ 0.80 (d, J = 7.5 Hz, 3H), 0.88 (d, J = 7.5 Hz, 3H), 1.18 (t, J = 7.4 Hz, 3H), 1.82 (sept, J = 7.5 Hz, 1H), 2.70 (m, 2H), 4.03 (m, 2H). |
| 9 | Ethyl-3-(4-isopropyl-2,5-dioxoimidazolidine-4-yl)propanoate | 5-Methyl-4-oxo-, ethyl ester hexanoic acid CAS 54857-48-6 | $^1$H NMR (300 MHz, CD$_3$OD): δ 0.91 (d, J = 7.5 Hz, 3H), 0.98 (d, J = 7.5 Hz, 3H), 1.24 (t, J = 7.2 Hz, 3H), 1.90-2.38 (m, 5H), 4.11 (q, J = 7.2 Hz, 2H). |

TABLE 1-continued

| Interm. No. | IUPAC name Structure | Starting material | $^1$H NMR δ (ppm) |
|---|---|---|---|
| 10 | 5-(5-Ethyl-1-H-indol-2-yl)-5-methylimidazolidine-2,4-dione | 1-(5-ethyl-1-H-indol-2-yl)ethanone CAS 16244-23-8 | $^1$H NMR (600 MHz, CD$_3$OD): δ 1.25 (t, J = 7.2 Hz, 3H), 1.84 (s, 3H), 2.69 (q, J = 7.2 Hz, 2H), 6.39 (s, 1H), 6.95 (d, J = 8.2 Hz, 1H), 7.12 (d, J = 8.2 Hz, 1H), 7.18 (s, 1H). |
| 11 | 5-iso-Propyl-5-(2-((4-methoxybenzyl)oxy)methyl)imidazolidine-2,4-dione | Intermediate 4 | $^1$HNMR (CD$_3$OD): δ 0.88 (d, J = 7.3 Hz, 3H), 0.91 (d, J = 7.3 Hz, 3H), 1.94-2.07 (m, 1H), 3.62 (d, J = 4.7 Hz, 2H), 3.80 (s, 3H), 4.44 (s, 2H), 6.86 (d, J = 8.5 Hz, 2H), 7.20 (d, J = 8.5 Hz, 2H). |

Example 6

Intermediate 12

3-Amino-5-ethyl-5-isopropylimidazolidine-2,4-dione

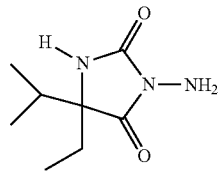

A mixture of 5-ethyl-5-(1-methylethyl)-2,4-imidazolidinedione CAS 98492-91-2 (2.47 g, 14.53 mmol) and hydrazine hydrate (10 mL) was heated at 150° C. in a sealed tube for 5 days. The crude mixture was purified by silica gel flash chromatography using MeOH:CH$_2$Cl$_2$, (1:19). Intermediate 12 was isolated as a white solid.

$^1$HNMR (CD$_3$OD): δ 0.78-0.92 (m, 6H), 0.95 (d, J=6.00 Hz, 3H), 1.78 (q, J=7.33 Hz, 2H), 1.96-2.06 (m, 1H).

Intermediates 13 through 19 were prepared in a similar manner to the procedure described in Example 6 for Intermediate 12. The starting material used and the results are tabulated below in Table 2.

TABLE 2

| Interm. No. | IUPAC name Structure | Starting material | $^1$H NMR δ (ppm) |
|---|---|---|---|
| 13 | 3-Amino-5-(4-hydroxyphenethyl)-5-methylimidazolidine-2,4-dione | 5-(4-hydroxyphenethyl)-5-methylimidazolidine-2,4-dione CAS 91567-45-2 | $^1$HNMR (CD$_3$OD): δ 1.39 (s, 3H), 1.80-1.92 (m, 1H), 1.98-2.42 (m, 1H), 2.30-2.40 (m, 1H), 2.50-2.60 (m, 1H), 6.66-6.70 (m, 2H), 6.90-7.05 (m, 2H). |
| 14 | 5-((1H-indol-3-yl)methyl)-3-amino-5-methylimidazolidine-2,4-dione | 2,4-Imidazolidinedione, 5-(1H-indol-3-ylmethyl)-5-methyl- CAS 54585-06-7 | $^1$H NMR (600 MHz, CD$_3$OD): δ 1.49 (s, 3H), 3.05 (d, J = 15.0 Hz, 1H), 3.25 (d, J = 15.0 Hz, 1H), 6.99 (t, J = 8.4 Hz, 1H), 7.05 (d, J = 8.4 Hz, 1H), 7.06 (s, 1H), 7.28 (d, J = 8.4 Hz, 1H), 7.55 (d, J = 8.4 Hz, 1H). |

TABLE 2-continued

| Interm. No. | IUPAC name Structure | Starting material | $^1$H NMR δ (ppm) |
|---|---|---|---|
| 15 | 3-Amino-5-methyl-5-(phenoxymethyl)imidazolidine-2,4-dione | 5-methyl-5-(phenoxymethyl)-imidazolidine-2,4-dione CAS 554445-55-5 | $^1$HNMR (CD$_3$OD): δ 1.44 (s, 3H), 4.00 (d, J = 8.4 Hz, 1H), 4.17 (d, J = 8.4 Hz, 1H), 6.88-6.98 (m, 3H), 7.20-7.25 (m, 2H). |
| 16 | 1-Amino-3',4'-dihydro-1'H-spiro[imidazolidine-4,2'-naphthalene]-2,5-dione | 3',4'-dihydro-1'H-spiro[imidazolidine-4,2'-naphthalene]-2,5-dione CAS 52094-70-9 | $^1$HNMR (CD$_3$OD): δ 1.80-1.95 (m, 1H), 2.05-2.20 (m, 1H), 2.76-2.90 (m, 1H). 2.99 (dt, J = 8.1, 4.0 Hz, 2H), 3.22-3.27 (m, 1H), 7.05-7.20 (m, 4H). |
| 17 | 3-Amino-5-ethyl-5-phenethylimidazolidine-2,4-dione | 5-ethyl-5-phenethylimidazolidine-2,4-dione CAS 857817-27-7 | $^1$HNMR (CD$_3$OD): δ 0.85-0.95 (m, 3H), 1.65-2.15 (m, 4H), 2.44 (dt, J = 12.6, 5.6 Hz, 1H), 2.62 (dt, J = 12.4, 4.8 Hz, 1H), 7.12-7.19 (m, 3H), 7.21-7.29 (m, 2H). |
| 18 | 3-Amino-5-isobutyl-5-phenethylimidazolidine-2,4-dione | 5-isobutyl-5-phenethylimidazolidine-2,4-dione CAS 858206-01-6 | $^1$HNMR (CD$_3$OD): δ 0.80-1.00 (m, 6H), 1.55-1.90 (m, 5H), 2.25-2.45 (m, 1H), 2.55-2.70 (m, 1H). 7.10-7.20 (m, 3H), 7.25-7.29 (m, 2H). |
| 19 | 3-Amino-5-(5-ethyl-1-H-indol-2-yl)-5-methylimidazolidine-2,4-dione | Intermediate 10 | $^1$H NMR (300 MHz, CD$_3$OD): δ 1.23 (t, J = 7.2 Hz, 3H), 1.82 (s, 3H), 2.66 (q, J = 7.2 Hz, 2H), 6.40 (s, 1H), 6.90-7.0 (m, 1H), 7.15-7.31 (m, 2H). |

Example 7

Intermediate 20

3-Amino-5-(4-chlorophenethyl)-5-methylimidazolidine-2,4-dione

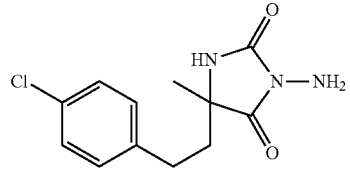 [SMILES: CC1(CCc2ccc(Cl)cc2)NC(=O)N(N)C1=O]

A mixture of 4-(4-chlorophenyl)butan-2-one CAS 3506-75-0 (1.82 g, 10 mmol), $(NH_4)_2CO_3$ (4.24 g, 40 mmol), KCN (2.5 g, 37.5 mmol) and EtOH (20 mL) was heated to 60° C. for 15 h. The crude mixture was filtered through a short celite column. Then the solvent was removed under reduced pressure.

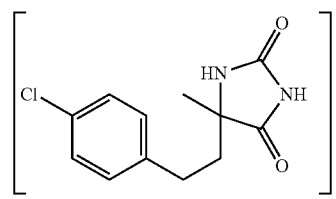

Intermediate 5-(4-chlorophenethyl)-5-methylimidazolidine-2,4-dione was isolated as a brown solid. A mixture of 5-(4-chlropheneyhtl)-5-methylimidazolidine-2,4-dione (400 mg, 1.9 mmol) and hydrazine hydrate (4 mL) was heated to 100° C. for 5 h in a sealed tube. This mixture was purified by silicagel chromatography using MeOH in $CH_2Cl_2$ as eluent, and Intermediate 20 was isolated as a white solid.

$^1$HNMR ($CD_3OD$): δ 1.40 (s, 3H), 1.82-1.95 (m, 1H), 2.01-2.10 (m, 1H), 2.40-2.46 (m, 1H), 2.58-2.66 (m, 1H), 7.14 (d, J=8.4 Hz, 2H), 7.25 (d, J=8.4 Hz, 2H).

Intermediates 21 through 31 were prepared in a similar manner to the procedure described in Example 7 for Intermediate 20. The starting materials used and the results are tabulated below in Table 3.

TABLE 3

| Interm. No. | IUPAC name Structure | Starting material | $^1$H NMR δ (ppm) for Compound |
|---|---|---|---|
| 21 | 3-Amino-5-(2-furan-2-yl)ethyl)-5-methylimidazolidine-2,4-dione | 4-(furan-2-yl)butan-2-one CAS 699-17-2 | $^1$HNMR ($CD_3OD$): δ 1.32 (s, 3H), 1.82-1.90 (m, 1H), 2.01-2.10 (m, 1H), 2.48-2.49 (m, 2H), 5.99-6.03 (m, 1H), 6.27 (dd, J = 3.1, 1.9 Hz, 1H), 7.31-7.35 (m, 1H). |
| 22 | 3-Amino-5-(2-fluorophenethyl)-5-methylimidazolidine-2,4-dione | 4-(2-fluorophenyl)butan-2-one CAS 63416-65-9 | $^1$HNMR ($CD_3OD$): δ 1.41 (s, 3H), 1.83-1.93 (m, 1H), 2.05-2.08 (m, 1H), 2.42-2.51 (m, 1H), 2.62-2.71 (m, 1H), 7.01 (t, J = 9.6 Hz, 1H), 7.07 (t, J = 8.4 Hz, 1H), 7.18-7.22 (m, 2H). |
| 23 | 3-Amino-5-(4-fluorophenethyl)-5-methylimidazolidine-2,4-dione | 4-(4-fluorophenyl)butan-2-one CAS 63416-61-5 | $^1$HNMR ($CD_3OD$): δ 1.40 (s, 3H), 1.80-2.10 (m, 2H), 2.35-2.45 (m, 1H), 2.55-2.70 (m, 1H), 6.97 (t, J = 9.0 Hz, 2H), 7.15 (dd, J = 9.0, 5.4, 2H). |
| 24 | 3-Amino-5-(3-fluorophenethyl)-5-methylimidazolidine-2,4-dione | 4-(3-fluorophenyl)butan-2-one CAS 3508-77-2 | $^1$HNMR ($CD_3OD$): δ 1.41 (s, 3H), 1.85-1.95 (m, 1H), 2.05-2.10 (m, 1H), 2.40- |

TABLE 3-continued

| Interm. No. | IUPAC name Structure | Starting material | $^1$H NMR δ (ppm) for Compound |
|---|---|---|---|
|  | (structure: 5-methyl-5-[2-(3-fluorophenyl)ethyl]-3-amino-imidazolidine-2,4-dione) |  | 2.50 (m, 1H), 2.60-2.70 (m, 1H), 6.82-6.94 (m, 2H), 6.96 (d, J = 7.9 Hz, 1H), 7.27 (q, J = 7.2 Hz, 1H). |
| 25 | 3-Amino-5-methyl-5-(2-(thiophen-2-yl)ethyl)imidazolidine-2,4-dione | 4-(thiophen-2-yl)butan-2-one CAS 59594-93-3 | $^1$HNMR (CD$_3$OD): δ 1.40 (s, 3H), 1.96-2.10 (m, 1H), 2.10-2.16 (m, 1H), 2.66-2.72 (m, 1H), 2.68-2.88 (m, 1H), 6.77-6.80 (m, 1H), 6.86-6.91 (m, 1H), 7.15-7.18 (m, 1H). |
| 26 | 3-Amino-5-methyl-5-(2-(5-methylfuran-2-yl)ethyl)imidazolidine-2,4-dione | 4-(5-methylfuran-2-yl)butan-2-one CAS 13679-56-6 | $^1$HNMR (CD$_3$OD): δ 1.38 (s, 3H), 1.89-1.98 (m, 1H), 2.12-2.20 (m, 1H), 2.20 (s, 3H), 2.39-2.50 (m, 1H), 2.55-2.65 (m, 1H), 5.82-5.90 (m, 2H). |
| 27 | 3-Amino-5-(3-fluoro-4-hydroxyphenethyl)-5-methylimidazolidine-2,4-dione | 4-(3-fluoro-4-hydroxyphenethyl)-butan-2-one CAS 173851-92-8 | $^1$HNMR (CD$_3$OD): δ 1.40 (s, 3H), 1.83-1.92 (m, 1H), 1.94-2.10 (m, 1H), 2.25-2.45 (m, 1H), 2.50-2.70 (m, 1H), 6.72-6.89 (m, 3H). |
| 28 | 3-Amino-5-(2-hydroxyphenethyl)-5-methylimidazolidine-2,4-dione | 4-(2-hydroxyphenethyl)butane-2-one CAS 61844-32-4 | $^1$HNMR (CD$_3$OD): δ 1.40 (s, 3H), 1.76-2.15 (m, 2H), 2.35-2.47 (m, 1H), 2.60-2.74 (m, 1H), 6.68-6.75 (m, 2H), 6.97-7.05 (m, 2H). |
| 29 | 3-Amino-5-(3-hydroxyphenethyl)-5-methylimidazolidine-2,4-dione | 4-(3-hydroxyphenethyl)butane-2-one CAS 56363-73-6 | $^1$HNMR (CD$_3$OD): δ 1.40 (s, 3H), 1.80-1.93 (m, 1H), 1.95-2.03 (m, 1H), 2.38 (dt, J = 12.8, 5.0 Hz, 1H), 2.59 (dt, J = 12.8, 5.0 Hz, 1H), 6.56-6.65 (m, 3H), 7.02-7.10 (m, 1H). |

TABLE 3-continued

| Interm. No. | IUPAC name Structure | Starting material | ¹H NMR δ (ppm) for Compound |
|---|---|---|---|
| 30 | 3-Amino-5-methyl-5-2-(pyridin-4-yl)ethyl)imidazolidine-2,4-dione | 4-(pyridin-4-yl)butan-2-one CAS 35250-71-6 | ¹HNMR (CD₃OD): δ 1.42 (s, 3H), 1.87-2.02 (m, 1H), 2.05-2.14 (m, 1H), 2.50-2.58 (m, 1H), 2.62-2.70 (m, 1H), 7.23-7.31 (m, 2H), 8.36-8.45 (m, 2H). |
| 31 | 3-Amino-5-(2-bromophenethyl)-5-ethyl)imidazolidine-2,4-dione | 1-(2-bromophenyl)pentan-3-one CAS 97640-57-8 | ¹HNMR (CD₃OD): δ 0.91 (t, J = 1.64-1.94 (m, 6H), 2.00 (td, J = 9.3, 5.1 Hz, 1H), 2.61 (td, J = 9.9, 5.1 Hz, 1H), 2.84 (td, J = 9.9, 5.1 Hz, 1H), 7.07-7.131 (m, 1H), 7.21-7.31 (m, 2H), 7.51 (d, J = 8.1 Hz, 1H). |

Example 8

Intermediate 32

3-Amino-5-isopropyl-5-(2-((4-methoxybenzyl)oxy)ethyl)imidazolidine-2,4-dione

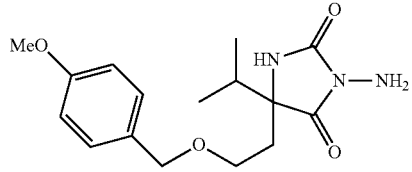 [SMILES: COc1ccc(COCCC2(C(C)C)NC(=O)N(N)C2=O)cc1]

A mixture of Intermediate 5 (320 mg, 1.05 mmol), K₂CO₃, DMF (3 mL), THF (3 mL) was heated to 70° C. and O-(2,4-dinitrophenyl)hydroxylamine CAS 17508-17-7 (224 mg, 1.55 mmol) was added in one portion. At 15 minute intervals O-(2,4-dinitrophenyl)hydroxylamine CAS 17508-17-7(112 mg each time) and K₂CO₃ (120 mg) were added four times. The mixture was cooled to RT, extracted with EtOAc (70 mL), washed with aq. K₂CO₃, dried (MgSO₄) and solvent removed. The crude intermediate was purified by silicagel chromatography using EtOAc in hexane as eluent and Intermediate 32 was isolated.

¹HNMR (CD₃OD): δ 0.86 (d, J=4.2 Hz, 3H), 0.95 (d, J=4.2 Hz, 3H), 1.94-2.00 (m, 2H), 2.18-2.22 (m, 1H), 3.45-3.50 (m, 2H), 3.77 (s, 3H), 4.26 (d, J=10.8 Hz, 1H), 4.34 (d, J=10.8 Hz, 1H), 6.82-6.90 (m, 2H), 7.20-7.24 (m, 2H).

Intermediates 33 through 39 were prepared in a similar manner to the procedure described in Example 8 for Intermediate 32. The starting materials used and the results are tabulated below in Table 4.

TABLE 4

| Interm. No. | IUPAC name Structure | Starting material | ¹H NMR δ (ppm) |
|---|---|---|---|
| 33 | 3-Amino-5-(4-bromophenethyl)-5-methylimidazolidine-2,4-dione | Intermediate 6 | ¹HNMR (CD₃OD): δ 1.40 (s, 3H), 1.83-1.92 (m, 1H), 2.00-2.09 (m, 1H), 2.38-2.47 (m, 1H), 2.58-2.67 (m, 1H), 7.08 (d, J = 7.8 Hz, 2H), 7.40 (d, J = 7.8 Hz, 2H). |

TABLE 4-continued

| Interm. No. | IUPAC name Structure | Starting material | ¹H NMR δ (ppm) |
|---|---|---|---|
| 34 | 3-Amino-5-(2-bromophenethyl)-5-methylimidazolidine-2,4-dione | Intermediate 7 | ¹HNMR (CD$_3$OD): δ 1.43 (s, 3H), 1.84-1.92 (m, 1H), 1.99-2.07 (m, 1H), 2.56-2.66 (m, 1H), 2.76-2.86 (m, 1H), 7.02-7.10 (m, 1H), 7.22-7.26 (m, 2H), 7.53 (d, J = 8.4 Hz, 1H). |
| 35 | Ethyl-2-(1-amino-4-isopropyl-2,5-dioxoimidazolidin-4-yl)acetate | Intermediate 8 | ¹HNMR (DMSO-d$_6$): δ 0.76 (d, J = 7.5 Hz, 3H), 0.84 (d, J = 7.5 Hz, 3H), 1.10 (t, J = 7.4 Hz, 3H), 1.85 (sept, J = 7.5 Hz, 1H), 2.76 (m, 2H), 4.01 (m, 2H). |
| 36 | Ethyl-3-(1-amino-4-isopropyl-2,5-dioxoimidazolidin-4-yl)propanoate | Intermediate 9 | ¹H NMR (300 MHz, CD$_3$OD): δ 0.87 (d, J = 7.5 Hz, 3H), 0.97 (d, J = 7.5 Hz, 3H), 1.23 (t, J = 7.2 Hz, 3H), 1.95-2.30 (m, 5H), 4.12 (q, J = 7.2 Hz, 2H). |
| 37 | 3-Amino-5,5-diisopropylimidazolidine-2,4-dione | 5,5-diisopropylimidazo-lidine-2,4-dione CAS 52532-01-1 | ¹H NMR (300 MHz, CDCl$_3$): δ 2.23 (sept, 2H), 1.00 (d, 6H), 0.95 (d, 6H). |
| 38 | 3-amino-5,5-dicyclopropylimidazolidine-2,4-dione | 5,5-dicyclopropyl2,4-Imidazolidinedione CAS 7250-75-1 | ¹H NMR (300 MHz, CDCl$_3$): δ 1.49 (m, 2H), 0.68-0.58 (m, 2H), 0.52-0.36 (m, 6H). |
| 39 | 3-Amino-5-isopropyl-5-(2-((4-methoxybenzyl)oxy)methyl)imidazolidine-2,4-dione | Intermediate 11 | ¹HNMR (CD$_3$OD): δ 0.86 (d, J = 4.2 Hz, 3H), 0.95 (d, J = 4.2 Hz, 3H), 1.94-2.00 |

TABLE 4-continued

| Interm. No. | IUPAC name Structure | Starting material | $^1$H NMR δ (ppm) |
|---|---|---|---|
| | 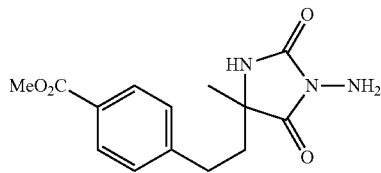 [SMILES: COC(=O)c1ccc(CCC2(C)NC(=O)N(N)C2=O)cc1] | | (m, 2H), 2.18-2.22 (m, 1H), 3.45-3.50 (m, 2H), 3.77 (s, 3H), 4.26 (d, J = 10.8 Hz, 1H), 4.34 (d, J = 10.8 Hz, 1H), 6.82-6.90 (m, 2H), 7.20-7.24 (m, 2H). |
| 40 | 3-Amino-5,5-dimethyl-1-phenylimidazolidine-2,4-dione | 5,5-dimethyl-1-phenylimidazo-lidine-2,4-dione CAS 138027-72-2 | $^1$H NMR (300 MHz, CDCl$_3$): δ 7.52-7.40 (m, 3H), 7.29-7.22 (m, 2H), 1.49 (s, 6H). |

Example 9

Intermediate 41

Methyl-4(2-(1-amino-4-methyl-2,5-dioxoimidazolidin-4-yl)ethyl)benzoate

Intermediate 33 (460 mg, 1.5 mmol), Phosphine, 1,1'-(1,3-propanediyl)bis[1,1-d]cyclohexyl-, tetrafluoroborate(1-) CAS 1002345-50-7 (40 mg, 0.08 mmol), Pd(OAc)$_2$ (9 mg), K$_2$CO$_3$ (600 mg, 4.5 mmol), molecular sieves (4 Å, 600 mg) DMSO (6 mL) were bubbled with carbon monoxide then MeOH (250 mg) was added to the reaction and the reaction was covered with a rubber septum and a carbon monoxide filled balloon was inserted into the septum. The reaction was heated to 75° C. for 16 h and was worked up by removing the solvent under reduced pressure, the crude was purified by silicagel chromatography using 5% 7N NH$_3$-MeOH and 95% CH$_2$Cl$_2$. Intermediate 41 was isolated as a white solid.

$^1$HNMR (CD$_3$OD): δ 1.41 (s, 3H), 1.90-1.97 (m, 1H), 2.07-2.14 (m, 1H), 2.52-2.54 (m, 1H), 2.66-2.71 (m, 1H), 3.88 (s, 3H), 7.27 (d, J=8.4 Hz, 2H), 7.91 (dd, J=8.4, 1.8 Hz, 2H).

Intermediates 42 and 43 were prepared in a similar manner to the procedure described in Example 9 for Intermediate 41. The starting materials used and the results are tabulated below in Table 5.

TABLE 5

| Interm. No. | IUPAC name Structure | Starting material | $^1$H NMR δ (ppm) |
|---|---|---|---|
| 42 | Methyl-2-(2-(1-amino-4-methyl-2,5-dioxoimidazolidin-4-yl)ethyl)benzoate | Intermediate 34 | $^1$HNMR (CD$_3$OD): δ 1.41 (s, 3H), 1.82-2.10 (m, 2H), 2.64-2.80 (m, 1H), 2.95-3.10 (m, 1H), 3,80 (s, 3H), 7.20-7.30 (m, 1H), 7.45 (t, J = 7.2 Hz, 2H), 7.83 (d, J = 7.2 Hz, 1H). |
| 43 | Methyl-2-(2-(1-amino-4-ethyl-2,5-dioxoimidazolidin-4-yl)ethyl)benzoate | Intermediate 31 | $^1$HNMR (CD$_3$OD): δ 0.89 (t, J = 7.5 Hz, 3H), 1.70-2.10 (m, |

TABLE 5-continued

| Interm. No. | IUPAC name Structure | Starting material | $^1$H NMR δ (ppm) |
|---|---|---|---|
| | 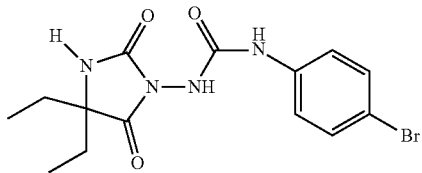 [SMILES: CCC1(CC)NC(=O)N(NC(=O)Nc2ccc(Br)cc2)C1=O] | | 4H), 2.45-2.65 (m, 2H), 3.88 (s, 3H), 7.24-7.35 (m, 2H), 7.46 (td, J = 7.5, 1.5 Hz, 1H), 7.84 (dd, J = 7.5, 1.5 Hz, 1H). |

Example 10

Compound 1

1-(4-Bromophenyl)-3-(4,4-diethyl-2,5-dioxoimidazolidin-1-yl)urea

A mixture of 3-amino-5,5-diethylimidazolidine-2,4-dione CAS 1007-61-0 (70 mg, 0.4 mmol), 4-bromophenylisocyanate CAS 2493-02-9 (80 mg, 0.4 mmol) in toluene (5 mL) was heated at 100° C. for 8 h. Upon cooling the reaction to ambient temperature, Compound 1 separated as a white solid, which was collected by filtration and dried under high vacuum.

$^1$HNMR (CD$_3$OD): δ 0.95 (br s, 6H), 1.65-1.75 (m, 2H), 1.81-1.91 (m, 2H), 7.36 (d, J=6.00 Hz, 2H), 7.40 (d, J=6.00 Hz, 2H).

Compounds 2 through 68 were prepared in a similar manner to the procedure described in Example 10 for Compound 1. The starting materials used and the results are tabulated below in Table 6.

TABLE 6

| Comp. No. | IUPAC name | Starting material | $^1$H NMR δ (ppm) for Compound |
|---|---|---|---|
| 2 | 1-(4-Chlorophenyl)-3-(4,4-diethyl-2,5-dioxoimidazolidin-1-yl)urea | 3-amino-5,5-diethylimidazolidine-2,4-dione CAS 1007-61-0 4-chlorophenyl isocyanate CAS 104-12-1 | $^1$HNMR (CD$_3$OD): δ 0.95 (br s, 6H), 1.65-1.75 (m, 2H), 1.81-1.95 (m, 2H), 7.36 (d, J = 6.00 Hz, 2H), 7.40 (d, J = 6.00 Hz, 2H). |
| 3 | 1-(4-Methoxyphenyl)-3-(4,4-diethyl-2,5-dioxoimidazolidin-1-yl)urea | 3-amino-5,5-diethylimidazolidine-2,4-dione CAS 1007-61-0 4-methoxyphenyl isocyanate CAS 5416-93-3 | $^1$HNMR (CD$_3$OD): δ 0.94 (br s, 6H), 1.68-1.78 (m, 2H), 1.80-1.95 (m, 2H), 3.75 (s, 3H), 6.85 (d, J = 9.00 Hz, 2H), 7.28 (d, J = 9.00 Hz, 2H). |
| 4 | 1-(4-Ethylphenyl)-3-(4,4-diethyl-2,5-dioxoimidazolidin-1-yl)urea | 3-amino-5,5-diethylimidazolidine-2,4-dione CAS 1007-61-0 4-ethylphenyl isocyanate CAS 23138-50-3 | $^1$HNMR (CD$_3$OD): δ 0.94 (t, J = 7.5 Hz, 6H), 1.19 (t, J = 7.8 Hz, 3H), 1.62-1.95 (m, 4H), 2.60 (q, J = 7.8 Hz, 2H), 7.11 (d, J = 8.4 Hz, 2H), 7.29 (d, J = 8.4 Hz, 2H). |

TABLE 6-continued

| Comp. No. | IUPAC name | Starting material | $^1$H NMR δ (ppm) for Compound |
|---|---|---|---|
| 5 | 1-(4-Cyanophenyl)-3-(4,4-diethyl-2,5-dioxoimidazolidin-1-yl)urea | 3-amino-5,5-diethylimidazolidine-2,4-dione CAS 1007-61-0 4-cyanophenyl isocyanate CAS 40465-45-0 | $^1$HNMR (CD$_3$OD): δ 0.95 (br s, 6H), 1.69-1.78 (m, 2H), 1.82-1.95 (m, 2H), 7.62 (s, 4H). |
| 6 | 1-(4-Bromo-2-fluorophenyl)-3-(4,4-diethyl-2,5-dioxoimidazolidin-1-yl)urea | 3-amino-5,5-diethylimidazolidine-2,4-dione CAS 1007-61-0 4-bromo-2-fluorophenyl isocyanate CAS 88112-75-8 | $^1$HNMR (CD$_3$OD): δ 0.94 (t, J = 7.2 Hz, 6H), 1.63-1.95 (m, 4H), 7.27 (dd, J = 1.2, 9.0 Hz, 1H), 7.36 (dd, J = 1.8, 9.0 Hz, 1H), 7.90 (t, J = 8.7 Hz, 1H). |
| 7 | 1-(4-Methylphenyl)-3-(4,4-diethyl-2,5-dioxoimidazolidin-1-yl)urea | 3-amino-5,5-diethylimidazolidine-2,4-dione CAS 1007-61-0 4-methylphenyl isocyanate CAS 622-58-2 | $^1$HNMR (CD$_3$OD): δ 0.94 (br s, 6H), 1.63-1.78 (m, 2H), 1.80-1.88 (m, 2H), 2.28 (s, 3H), 7.09 (d, J = 8.4 Hz, 2H), 7.26 (d, J = 8.4 Hz, 2H). |
| 8 | 1-(4-Methylthiophenyl)-3-(4,4-diethyl-2,5-dioxoimidazolidin-1-yl)urea | 3-amino-5,5-diethylimidazolidine-2,4-dione CAS 1007-61-0 4-thiomethylphenyl isocyanate CAS 1632-84-4 | $^1$HNMR (CD$_3$OD): δ 0.95 (br s, 6H), 1.68-1.78 (m, 2H), 1.82-1.90 (m, 2H), 2.43 (s, 3H), 7.22 (d, J = 6.6 Hz, 2H), 7.35 (d, J = 6.6 Hz, 2H). |
| 9 | 1-(4-Bromophenyl)-3-(4-methyl-2,5-dioxo-4-phenethylimidazolidin-1-yl)urea | Imidazolidinedione, 3-amino-5-methyl-5-(2-phenylethyl)-CAS 956437-87-9 4-bromophenylisocyanate CAS 2493-02-9 | $^1$HNMR (CD$_3$OD): δ 1.49 (s, 3H), 1.94-2.01 (m, 1H), 2.07-2.17 (m, 1H), 2.60 (br s, 1H), 2.66-2.75 (m, 1H), 7.14-7.19 (m, 3H), 7.22-7.31 (m, 2H), 7.37 (d, J = 5.86 Hz, 2H), 7.41 (d, J = 5.86 Hz, 2H). |
| 10 | 1-(4-Bromophenyl)-3-(2,4-dioxo-1,3-diazaspiro[4.4]nonan-3-yl)urea | 3-amino-1,3-diazaspiro[4.4]nonane-2,4-dione CAS 16252-62-3 4-bromophenylisocyanate CAS 2493-02-9 | $^1$HNMR (CD$_3$OD): δ 1.75-1.90 (m, 6H), 2.15-2.25 (br s, 2H), 7.36 (d, J = 6.6 Hz, 2H), 7.41 (d, J = 6.6 Hz, 2H). |

TABLE 6-continued

| Comp. No. | IUPAC name | Starting material | ¹H NMR δ (ppm) for Compound |
|---|---|---|---|
| 11 | 1-(4-Bromo-2-fluorophenyl)-3-(2,4-dioxo-1,3-diazaspiro[4.4]nonan-3-yl)urea | 3-amino-1,3-diazaspiro[4,4]nonane-2,4-dione CAS 16252-62-3 4-bromo-2-fluorophenyl isocyanate CAS 88112-75-8 | ¹HNMR (CD₃OD): δ 1.84-1.94 (m, 6H), 2.15-2.25 (m 2H), 7.28 (dt, J = 1.5, 9.0 Hz, 1H), 7.36 (dd, J = 1.2, 9.0 Hz, 1H), 7.89 (t, J = 9.0 Hz, 1H). |
| 12 | 1-(4-Bromophenyl)-3-(4,4-dimethyl-2,5-dioxoimidazolidin-1-yl)urea | 2,4-Imidazolidinedione, 3-amino-5,5-dimethyl- CAS 1123-44-0 4-bromo-phenylisocyanate CAS 2493-02-9 | ¹HNMR (CD₃OD): δ 1.52 (s, 6H), 7.27 (d, J = 8.4, Hz, 2H), 7.46 (d, J = 8.4 Hz, 2H). |
| 13 | 1-(4-Bromophenyl)-3-(2,5-dioxo-1',3'-dihydrospiro[imidazolidine-4,2'-inden]-1-yl)urea | Intermediate 2 4-bromophenyl isocyanate CAS 2493-02-9 | ¹HNMR (CD₃OD): δ 3.22 (d, J = 16.2 Hz, 2H), 3.58 (d, J = 16.2 Hz, 2H), 7.20-7.22 (m, 2H), 7.24-7.30 (m, 2H), 7.37 (d, J = 8.4 Hz, 2H), 7.41 (d, J = 8.4 Hz, 2H). |
| 14 | 1-(4-Bromophenyl)-3-(2,4-dioxo-1,3-diazaspiro[4.5]decan-3-yl)urea | 1,3-Diazaspiro[4.5]decane-2,4-dione, 3-amino CAS 16252-63-4 4-bromo-phenylisocyanate CAS 2493-02-9 | ¹HNMR (CD₃OD): δ 1.40-1.90 (m, 10H), 7.36 (d, J = 8.4 Hz, 2H), 7.41 (d, J = 8.4 Hz, 2H). |
| 15 | 1-(4-Bromo-2-fluorophenyl)-3-(2,4-dioxo-1,3-diazaspiro[4.5]decan-3-yl)urea | 1,3-Diazaspiro[4.5]decane-2,4-dione, 3-amino CAS 16252-63-4 4-bromo-2-fluorophenyl isocyanate CAS 88112-75-8 | ¹HNMR (CD₃OD): δ 1.40-1.90 (m, 10H), 7.28 (dd, J = 10.4, 2.2 Hz, 1H), 7.36 (dd, J = 10.4, 2.2 Hz, 1H), 7.86 (t, J = 8.6 Hz, 1H). |
| 16 | 1-(4-Chloro-2-fluorophenyl)-3-(4,4-diethyl-2,5-dioxoimidazolidin-1-yl)urea | 3-amino-5,5-diethylimidazolidine-2,4-dione CAS 1007-61-0 4-chloro-2-fluorophenyl isocyanate CAS 69922-26-5 | ¹HNMR (CD₃OD): δ 0.96 (t, H = 7.2 Hz, 6H), 1.65-1.91 (m, 4H), 7.12 (dd, J = 8.79, 2.34 Hz, 1H), 7.22 (dd, J = 10.84, 2.34 Hz, 1H), 7.93 (t, J = 8.79 Hz, 1H). |

TABLE 6-continued

| Comp. No. | IUPAC name | Starting material | $^1$H NMR δ (ppm) for Compound |
|---|---|---|---|
| 17 | 1-(4-Bromo-2-fluorophenyl)-3-(4-methyl-2,5-dioxo-4-phenethylimidazolidin-1-yl)urea | 2,4-Imidazolidinedione, 3-amino-5-methyl-5-(2-phenylethyl)- CAS 956437-87-9 4-bromo-2-fluorophenyl isocyanate CAS 88112-75-8 | $^1$HNMR (CD$_3$OD): δ 1.49 (s, 3H), 1.90-2.01 (m, 1H), 2.07-2.19 (m, 1H), 2.50 (br s, 1H), 2.66-2.78 (m, 1H), 7.12-7.20 (m, 3H), 7.22-7.29 (m, 3H), 7.37 (dd, J = 10.55, 2.05 Hz, 1H), 7.91 (t, J = 8.79 Hz, 2H). |
| 18 | 1-(4-Bromophenyl)-3-(4-ethyl-4-isopropyl-2,5-dioxoimidazolidin-1-yl)urea | Intermediate 12 4-bromophenyl isocyanate CAS 2493-02-9 | $^1$HNMR (CD$_3$OD): δ 0.90-1.05 (m, 9H), 1.83 (q, J = 7.33 Hz, 2H), 1.98-2.10 (m, 1H), 7.34 (d, J = 7.33 Hz, 2H), 7.40 (d, J = 7.33 Hz, 2H). |
| 19 | 1-(4-Chloro-3-fluorophenyl)-3-(4,4-diethyl-2,5-dioxoimidazolidin-1-yl)urea | 3-amino-5,5-diethylimidazolidine-2,4-dione CAS 1007-61-0 4-chloro-3-fluorophenylisocyanate CAS 51163-28-1 | $^1$HNMR (CD$_3$OD): δ 0.90-1.05 (m, 9H), 1.83 (q, J = 7.33 Hz, 2H), 1.98-2.10 (m, 1H), 7.34 (d, J = 7.33 Hz, 2H), 7.40 (d, J = 7.33 Hz, 2H). |
| 20 | 1-(4-Bromo-2-fluorophenyl)-3-(4-ethyl-4-isopropyl-2,5-dioxoimidazolidin-1-yl)urea | Intermediate 12 4-bromo-2-fluorophenyl isocyanate CAS 88112-75-8 | $^1$HNMR (CD$_3$OD): δ 0.90-1.05 (m, 9H), 1.83 (q, J = 7.23 Hz, 2H), 1.98-2.12 (m, 1H), 7.27 (d, J = 10.55, 2.05 Hz, 1H), 7.36 (dd, J = 10.55, 2.05, 1H), 7.89 (t, J = 8.79 Hz, 1H). |
| 21 | 1-(2,4-Dioxo-1,3-diazaspiro[4,5]decan-3-yl)-3-(4-methoxypheynyl)urea | 3-amino-1,3-diazaspiro[4.5]decane-2,4-dione CAS 16252-63-4 1-isocyanato-4-methoxybenzene CAS 5416-93-3 | $^1$HNMR (CD$_3$OD): δ 1.35-1.90 (m, 10H), 3.76 (s, 3H), 6.85 (d, J = 9.1 Hz, 2H), 7.29 (d, J = 9.1 Hz, 2H). |

TABLE 6-continued

| Comp. No. | IUPAC name | Starting material | $^1$H NMR δ (ppm) for Compound |
|---|---|---|---|
| 22 | (S)-1-(4-Bromophenyl)-3-(1,3-dioxo-10,10a-dihydroimidazo[1,5-b]isoquinolin-2(1H,3H,5H)-yl)urea | (S)-2-amino-10,10a-dihydroimidazo[1,5-b]isoquinoline-1,3(2H,5H)-dione CAS 128609-05-2 1-bromo-4-isocyanatobenzene CAS 2493-02-9 | $^1$HNMR (CD$_3$OD): δ 3.27 (dd, J = 15.6, 4.2 Hz, 2H), 4.34 (dd, J = 11.4, 4.2 Hz, 1H), 4.49 (d, J = 16.8 Hz, 1H), 4.97 (d, J = 16.8 Hz, 1H), 7.23-7.30 (m, 4H), 7.35-7.48 (m, 4H). |
| 23 | (S)-1-(4-Bromo-2-fluorophenyl)-3-(1,3-dioxo-10,10a-dihydroimidazo[1,5-b]isoquinolin-2(1H,3H,5H)-yl)urea | (S)-2-amino-10,10a-dihydroimidazo[1,5-b]isoquinoline-1,3(2H,5H)-dione CAS 128609-05-2 4-bromo-2-fluoro-1-isocyanatobenzene CAS 88112-75-8 | $^1$HNMR (CD$_3$OD): δ 3.02 (t, J = 13.8 Hz, 1H), 3.27 (dd, J = 15.0, 4.2 Hz, 1H), 4.35 (d, J = 11.4 Hz, 1H), 4.49 (d, J = 16.8 Hz, 1H), 4.98 (d, J = 16.8 Hz, 1H), 7.20-7.42 (m, 6H), 7.88 (t, J = 8.4 Hz, 1H). |
| 24 | 1-(4-Bromo-2-fluorophenyl)-3-(2,5-dioxo-1',3'-dihydrospiro[imidazolidine-4,2'-inden]-1-yl)urea | Intermediate 2 4-bromo-2-fluoro-1-isocyanatobenzene CAS 88112-75-8 | $^1$HNMR (CD$_3$OD): δ 3.23 (d, J = 16.2 Hz, 2H), 3.58 (d, J = 16.2 Hz, 2H), 7.20-7.27 (m, 4H), 7.27-7.30 (m, 1H), 7.37 (dd, J = 10.6, 2.1 Hz, 1H), 7.91 (t, J = 8.4 Hz, 1H). |
| 25 | 1-(4-Bromophenyl)-3-(4-methyl-2,5-dioxo-4-(phenoxymethyl)imidazolidin-1-yl)urea | Intermediate 15 1-bromo-4-isocyanatobenzene CAS 2493-02-9 | $^1$HNMR (CD$_3$OD): δ 1.55 (s, 3H), 4.07 (d, J = 9.0 Hz, 1H), 4.22 (d, J = 9.0 Hz, 1H), 6.95 (t, J = 6.6 Hz, 3H), 7.26 (t, J = 8.4 Hz, 2H), 7.38 (d, J = 9.0 Hz, 2H), 7.41 (d, J = 9.0 Hz, 2H). |

TABLE 6-continued

| Comp. No. | IUPAC name | Starting material | $^1$H NMR δ (ppm) for Compound |
|---|---|---|---|
| 26 | 1-(4-Bromo-2-fluorophenyl)-3-(2,5-dioxo-3',4'-dihydro-1'H-spiro[imidazolidine-4,2'-napthlalen-1-yl)urea | Intermediate 16 4-bromo-2-fluoro-1-isocyanatobenzene CAS 88112-75-8 | $^1$HNMR (CD$_3$OD): δ 1.95-2.10 (m, 1H), 2.15-2.30 (m, 1H), 2.76-3.05 (m, 3H). 3.30-3.34 (m, 1H), 7.05-7.20 (m, 4H), 7.25-7.35 (m, 1H), 7.38 (dd, J = 10.5, 2.3, 1H), 7.91 (t, J = 8.6 Hz, 1H). |
| 27 | 1-(4-Bromophenyl)-3-(2,5-dioxo-3',4'-dihydro-1'H-spiro[imidazolidine-4,2'-napthlalen-1-yl)urea | Intermediate 16 1-bromo-4-isocyanatobenzene CAS 2493-02-9 | $^1$HNMR (CD$_3$OD): δ 1.95-2.10 (m, 1H), 2.15-2.30 (m, 1H), 2.76-3.05 (m, 3H). 3.30-3.34 (m, 1H), 7.05-7.20 (m, 4H), 7.25-7.35 (m, 1H), 7.38 (dd, J = 10.5, 2.3, 1H), 7.91 (t, J = 8.6 Hz, 1H). |
| 28 | 1-(4-Bromo-2-fluorophenyl)-3-(4-methyl-2,5-dioxo-4-(phenoxymethyl)imidazolidin-1-yl)urea | Intermediate 15 4-bromo-2-fluoro-1-isocyanatobenzene CAS 88112-75-8 | $^1$HNMR (CD$_3$OD): δ 1.54 (s, 3H), 4.07 (d, J = 8.4 Hz, 1H), 4.22 (d, J = 8.4 Hz, 1H), 6.94-6.99 (m, 3H), 7.26-7.31 (m, 3H), 7.35-7.38 (m, 1H), 7.41 (t, J = 8.4 Hz, 1H). |
| 29 | 1-(4-Bromo-2-fluorophenyl)-3-(4-ethyl-2,5-dioxo-4-(phenethyl)imidazolidin-1-yl)urea | Intermediate 17 4-bromo-2-fluoro-1-isocyanatobenzene CAS 88112-75-8 | $^1$HNMR (CD$_3$OD): δ 0.93-1.00 (m, 3H), 1.70-2.20 (m, 4H), 2.60-2.75 (m, 2H), 7.12-7.19 (m, 3H), 7.25-7.23 (m, 3H), 7.36 (dd, J = 10.5, 2.1, 1H), 7.91 (t, J = 8.6 Hz, 1H). |

TABLE 6-continued

| Comp. No. | IUPAC name | Starting material | $^1$H NMR δ (ppm) for Compound |
|---|---|---|---|
| 30 | 1-(4-Bromophenyl)-3-(4-ethyl-2,5-dioxo-4-(phenethyl)imidazolidin-1-yl)urea | Intermediate 17 1-bromo-4-isocyanatobenzene CAS 2493-02-9 | $^1$HNMR (CD$_3$OD): δ 0.93-1.00 (m, 3H), 1.70-2.20 (m, 4H), 2.60-2.75 (m, 2H), 7.12-7.19 (m, 3H), 7.22-7.27 (m, 2H), 7.33-7.42 (m, 4H). |
| 31 | 1-(4-Bromophenyl)-3-(4-isobutyl-2,5-dioxo-4-phenethyl)imidazolidin-1-yl)urea | Intermediate 18 1-bromo-4-isocyanatobenzene CAS 2493-02-9 | $^1$HNMR (CD$_3$OD): δ 0.92 (d, J = 6.5 Hz, 6H), 1.60-2.20 (m, 6H), 2.55-2.75 (m, 1H), 7.10-7.20 (m, 3H), 7.22-7.26 (m, 2H), 7.30-7.42 (m, 4H) |
| 32 | 1-(4-Bromo-2-fluorophenyl)-3-(4-isobutyl-2,5-dioxo-4-phenethyl)imidazolidin-1-yl)urea | Intermediate 18 4-bromo-2-fluoro-1-isocyanatobenzene CAS 88112-75-8 | $^1$HNMR(CD$_3$OD): δ 0.91 (d, J = 6.5 Hz, 3H), 0.98 (d, J = 6.5 Hz, 3H), 1.60-2.15 (m, 6H), 2.55-2.70 (m, 1H), 7.12-7.19 (m, 3H), 7.21-7.30 (m, 3H), 7.32-7.40 (m, 1H), 7.92 (t, J = 8.6 Hz, 1H). |
| 33 | 1-(4-Bromophenyl)-3-(4-(4-chlorophenethyl)-4-methyl-2,5-dioxoimidazolidin-1-yl)urea | Intermediate 20 1-bromo-4-isocyanatobenzene CAS 2493-02-9 | $^1$HNMR (CD$_3$OD): δ 1.50 (s, 3H), 1.90-2.00 (m, 1H), 2.05-2.15 (m, 1H), 2.60-2.80 (m, 2H), 7.18 (d, J = 8.4 Hz, 2H), 7.26 (d, J = 8.4 Hz, 2H), 7.36 (d, J = 9.0 Hz, 2H), 7.40 (d, J = 9.0 Hz, 2H). |

TABLE 6-continued

| Comp. No. | IUPAC name | Starting material | $^1$H NMR δ (ppm) for Compound |
|---|---|---|---|
| 34 | 1-(4-Bromo-2-fluorophenyl)-3-(4-chlorophenethyl)-4-methyl-2,5-dioxo-imidazolidin-1-yl)urea | Intermediate 20 4-bromo-2-fluoro-1-isocyanatobenzene CAS 88112-75-8 | $^1$HNMR (DMSO-D$_6$): δ 1.37 (s, 3H), 1.82-1.90 (m, 1H), 1.92-2.00 (m, 1H), 2.55-2.65 (m, 2H), 7.20 (d, J = 7.2 Hz, 2H), 7.33 (d, J = 8.4 Hz, 3H), 7.58 (dd, J = 10.8, 1.8 Hz, 1H), 7.90 (brs, 1H). |
| 35 | 1-(4-Bromophenyl)-3-(4-(2-furan-2-yl)ethyl)-4-methyl-2,5-dioxoimidazolidin-1-yl)urea | Intermediate 21 1-bromo-4-isocyanatobenzene CAS 2493-02-9 | $^1$HNMR (CD$_3$OD): δ 1.48 (s, 3H), 1.95-2.06 (m, 1H), 2.12-2.25 (m, 1H), 2.55-2.80 (m, 2H), 6.05 (dd, J = 3.2, 0.6 Hz, 1H), 6.28 (dd, J = 3.1, 1.9 Hz, 1H), 7.22-7.50 (m, 5H). |
| 36 | 1-(4-Bromo-2-fluorophenyl)-3-(4-(2-furan-2-yl)ethyl)-4-methyl-2,5-dioxoimidazolidin-1-yl)urea | Intermediate 21 4-bromo-2-fluoro-1-isocyanatobenzene CAS 88112-75-8 | $^1$HNMR (DMSO-D$_6$): δ 1.38 (s, 3H), 1.91-2.00 (m, 1H), 2.02-2.12 (m, 1H), 2.50-2.70 (m, 2H), 5.98-6.01 (m, 1H), 6.24 (dd, J = 3.1, 1.9 Hz, 1H), 7.30 (dd, J = 1.9, 0.7 Hz, 1H). |
| 37 | 1-(4-Bromophenyl)-3-(4-(2-fluorophenethyl)-4-methyl-2,5-dioxoimidazolidin-1-yl)urea | Intermediate 22 1-bromo-4-isocyanatobenzene CAS 2493-02-9 | $^1$HNMR (CD$_3$OD): δ 1.50 (s, 3H), 1.90-2.00 (m, 1H), 2.09-2.20 (m, 1H), 2.60-2.85 (m, 2H), 7.02 (t, J = 9.6 Hz, 1H), 7.08 (t, J = 8.4 Hz, 1H), 7.20-7.30 (m, 2H), 7.35-7.45 (m, 4H). |

TABLE 6-continued

| Comp. No. | IUPAC name | Starting material | $^1$H NMR δ (ppm) for Compound |
|---|---|---|---|
| 38 | 1-(4-Bromo-2-fluorophenyl)-3-(4-(2-fluorophenethyl)-4-methyl-2,5-dioxoimidazolidin-1-yl)urea | Intermediate 22 4-bromo-2-fluoro-1-isocyanatobenzene CAS 88112-75-8 | $^1$HNMR (DMSO-D$_6$): δ 1.50 (s, 3H), 1.92-2.00 (m, 1H), 2.10-2.18 (m, 1H), 2.60-2.82 (m, 2H), 7.02 (t, J = 9.6 Hz, 1H), 7.08 (t, J = 8.4 Hz, 1H), 7.20-7.28 (m, 2H), 7.28 (d, J = 8.4 Hz, 1H), 7.37 (dd, J = 8.4, 2.2 Hz, 1H), 7.92 (t, J = 9.0 Hz, 1H). |
| 39 | 1-(4-Bromophenyl)-3-(4-(4-fluorophenethyl)-4-methyl-2,5-dioxoimidazolidin-1-yl)urea | Intermediate 23 1-bromo-4-isocyanatobenzene CAS 2493-02-9 | $^1$HNMR (CD$_3$OD): δ 1.49 (s, 3H), 1.88-2.01 (m, 1H), 2.05-2.17 (m, 1H), 2.50-2.77 (m, 2H), 6.92-7.03 (m, 2H), 7.18-7.25 (m, 2H), 7.31-7.44 (m, 4H) |
| 40 | 1-(4-Bromo-2-fluorophenyl)-3-(4-(4-fluorophenethyl)-4-methyl-2,5-dioxoimidazolidin-1-yl)urea | Intermediate 23 4-bromo-2-fluoro-1-isocyanatobenzene CAS 88112-75-8 | $^1$HNMR (CD$_3$OD): δ 1.49 (s, 3H), 1.88-2.18 (m, 2H), 2.55-2.78 (m, 2H), 6.94-7.02 (m, 2H), 7.15-7.21 (m, 2H), 7.23-7.28 (m, 1H), 7.40-7.45 (m, 1H), 7.91 (t, J = 9.0 Hz, 1H). |
| 41 | 1-(4-Bromophenyl)-3-(4-(3-fluorophenethyl)-4-methyl-2,5-dioxoimidazolidin-1-yl)urea | Intermediate 24 1-bromo-4-isocyanatobenzene CAS 2493-02-9 | $^1$HNMR (CD$_3$OD): δ 1.50 (s, 3H), 1.90-2.05 (m, 1H), 2.08-2.20 (m, 1H), 2.60-2.80 (m, 2H), 6.85-7.02 (m, 3H), 7.23-7.31 (m, 1H), 7.32-7.45 (m, 4H). |

TABLE 6-continued

| Comp. No. | IUPAC name | Starting material | $^1$H NMR δ (ppm) for Compound |
|---|---|---|---|
| 42 | 1-(4-Bromophenyl)-3-(4-(4-hydroxyphenethyl)-4-methyl-2,5-dioxoimidazolidin-1-yl)urea | Intermediate 13 1-bromo-4-isocyanatobenzene CAS 2493-02-9 | $^1$HNMR (CD$_3$OD): δ 1.48 (s, 3H), 1.80-2.75 (m, 2H), 2.45-2.65 (m, 2H), 6.74 (d, J = 8.7 Hz, 2H), 7.00 (d, J = 8.7 Hz, 2H), 7.35-7.43 (m, 4H). |
| 43 | 1-(4-Bromophenyl)-3-(4-methyl-2,5-dioxo-4-(2-thiophen-2-yl)ethyl)imidazolidin-1-yl)urea | Intermediate 25 1-bromo-4-isocyanatobenzene CAS 2493-02-9 | $^1$HNMR (CD$_3$OD): δ 1.49 (s, 3H), 1.89-2.09 (m, 1H), 2.12-2.28 (m, 1H), 2.75-3.00 (m, 2H), 6.83 (dd, J = 3.5, 1.2 Hz, 1H), 6.90 (dd, J = 5.1, 3.4 Hz, 1H), 7.18 (dd, 5.3, 1.2 Hz, 1H), 7.33-7.45 (m, 4H). |
| 44 | 1-(4-Bromo-2-fluorophenyl)-3-(4-methyl-2,5-dioxo-4-(2-thiophen-2-yl)ethyl)imidazolidin-1-yl)urea | Intermediate 25 4-bromo-2-fluoro-1-isocyanatobenzene CAS 88112-75-8 | $^1$HNMR (CD$_3$OD): δ 1.49 (S, 3H), 1.98-2.10 (m, 1H), 2.15-2.27 (m, 1H), 2.75-3.00 (m, 2H), 6.83 (d, J = 2.93, 1H), 6.90 (dd, J = 5.1, 3.4 Hz, 1H), 7.18 (dd, J = 5.1, 0.7 Hz, 1H), 7.28 (dt, J = 8.8, 1.5 Hz, 1H), 7.37 (dd, J = 10.6, 2.3 Hz, 1H), 7.91 (t, J = 8.6 Hz, 1H). |
| 45 | 1-(4-Bromo-2-fluorophenyl)-3-(4-(4-hydroxyphenethyl)-4-methyl-2,5-dioxoimidazolidin-1-yl)urea | Intermediate 13 4-bromo-2-fluoro-1-isocyanatobenzene CAS 88112-75-8 | $^1$HNMR (CD$_3$OD): δ 1.48 (s, 3H), 1.82-1.95 (m, 1H), 2.03-2.14 (m, 1H), 2.40-2.70 (m, 2H), 6.65-6.72 (m, 2H), 6.95-7.01 (m, 2H), 7.25-7.30 (m, 1H), 7.29-7.40 (m, 1H), 7.91 (t, J = 8.7 Hz, 1H). |

TABLE 6-continued

| Comp. No. | IUPAC name | Starting material | $^1$H NMR δ (ppm) for Compound |
|---|---|---|---|
| 46 | 1-(4-Bromophenyl)-3-(4-methyl-4-(2-(5-methylfuran-2-yl)ethyl)2,5-dioxoimidazolidin-1-yl)urea | Intermediate 26 1-bromo-4-isocyanatobenzene CAS 2493-02-9 | $^1$HNMR (CD$_3$OD): δ 1.48 (s, 3H), 1.89-2.02 (m, 1H), 2.12-2.20 (m, 1H), 2.20 (s, 3H), 2.50-2.80 (m, 2H), 5.83-5.90 (m, 2H), 7.31-7.42 (m, 4H) |
| 47 | 1-(4-Bromophenyl)-3-(4-(3-fluoro-4-hydroxyphenethyl)-4-methyl-2,5-dioxoimidazolidin-1-yl)urea | Intermediate 27 1-bromo-4-isocyanatobenzene CAS 2493-02-9 | $^1$HNMR (CD$_3$OD): δ 1.48 (s, 3H), 1.89-2.00 (m, 1H), 2.02-2.15 (m, 1H), 2.45-2.70 (m, 2H), 6.75-6.92 (m, 3H), 7.31-7.44 (m, 4H). |
| 48 | 1-(4-Bromo-2-fluorophenyl)-3-(4-(3-fluoro-4-hydroxyphenethyl)-4-methyl-2,5-dioxoimidazolidin-1-yl)urea | Intermediate 27 4-bromo-2-fluoro-1-isocyanatobenzene CAS 88112-75-8 | $^1$HNMR (CD$_3$OD): δ 1.48 (s, 3H), 1.89-2.00 (m, 1H), 2.02-2.15 (m, 1H), 2.45-2.70 (m, 2H), 6.75-6.92 (m, 2H), 7.25-7.31 (m, 1H), 7.33-7.40 (m, 1H), 7.36 (dd, J = 10.6, 2.1 Hz, 1H), 7.91 (t, J = 8.8 Hz, 1H). |
| 49 | 1-(4-Bromophenyl)-3-(4-isopropyl-4-(2-((4-methoxybenzyl)oxy)ethyl)-2,5-dioxoimidazolidin-1-yl)urea | Intermediate 32 1-bromo-4-isocyanatobenzene CAS 2493-02-9 | δ $^1$HNMR (CD$_3$OD): δ 0.98 (d, J = 7.2 Hz, 3H), 1.01 (d, J = 7.2 Hz, 3H), 2.00-2.10 (m, 2H), 2.20-2.31 (m, 1H), 3.50-3.70 (m, 2H), 3.75 (s, 3H), 4.33 (d, J = 11.4 Hz, 1H), 4.43 (d, J = 11.2 Hz, 1H), 6.81 (d, J = 8.7 Hz, 2H), 7.20 7.41 (m, 6H). |
| 50 | 1-(4-Bromophenyl)-3-(4-(2-hydroxyphenethyl)-4-methyl- | Intermediate 28 1-bromo-4- | $^1$HNMR (CD$_3$OD): δ 1.49 (s, 3H), 1.91- |

| Comp. No. | IUPAC name | Starting material | $^1$H NMR δ (ppm) for Compound |
|---|---|---|---|
| | 2,5-dioxoimidazolidin-1-yl)urea | isocyanatobenzene CAS 2493-02-9 | 2.14 (m, 2H), 2.45-2.55 (m, 1H), 2.68-2.80 (m, 1H), 6.70-6.76 (m, 2H), 6.95-7.10 (m, 2H), 7.31-7.42 (m, 4H) |
| 51 | 1-(4-Bromo-2-fluorophenyl)-3-(4-(2-hydroxyphenethyl)-4-methyl-2,5-dioxoimidazolidin-1-yl)urea | Intermediate 28 4-bromo-2-fluoro-1-isocyanatobenzene CAS 88112-75-8 | $^1$HNMR (CD$_3$OD): δ 1.48 (s, 3H), 1.90-2.15 (m, 2H), 2.40-2.60 (m, 1H), 2.65-2.82 (m, 1H), 6.70-6.76 (m, 2H), 6.95-7.10 (m, 2H), 7.24-7.31 (m, 1H), 7.36 (dd, J = 10.6, 2.3 Hz, 1H), 7.91 (t, J = 8.6 Hz, 1H). |
| 52 | 1-(4-Bromophenyl)-3-(4-(3-hydroxyphenethyl)-4-methyl-2,5-dioxoimidazolidin-1-yl)urea | Intermediate 29 1-bromo-4-isocyanatobenzene CAS 2493-02-9 | $^1$HNMR (CD$_3$OD): δ 1.49 (s, 3H), 1.90-2.00 (m, 1H), 2.04-2.16 (m, 1H), 2.40-2.70 (m, 2H), 6.57-6.67 (m, 3H), 7.07 (t, J = 7.9 Hz, 1H), 7.36-7.45 (m, 4H). |
| 53 | 1-(4-Bromo-2-fluorophenyl)-3-(4-(3-hydroxyphenethyl)-4-methyl-2,5-dioxoimidazolidin-1-yl)urea | Intermediate 29 4-bromo-2-fluoro-1-isocyanatobenzene CAS 88112-75-8 | $^1$HNMR (CD$_3$OD): δ 1.48 (s, 3H), 1.90-2.00 (m, 1H), 2.04-2.16 (m, 1H), 2.40-2.70 (m, 2H), 6.57-6.67 (m, 3H), 7.07 (t, J = 7.9 Hz, 1H), 7.27 (dd, J = 10.6, 2.1 Hz, 1H), 7.36 (dd, J = 10.6, 2.1 Hz, 1H), 7.91 (t, J = 8.6 Hz, 1H). |

TABLE 6-continued

| Comp. No. | IUPAC name | Starting material | $^1$H NMR δ (ppm) for Compound |
|---|---|---|---|
| 54 | 1-(4-Bromophenyl)-3-(4-methyl-2,5-dioxo-4-(2-(pyridin-4-yl)ethyl)imidazolidin-1-yl)urea | Intermediate 30 1-bromo-4-isocyanatobenzene CAS 2493-02-9 | $^1$HNMR (CD$_3$OD): δ 1.50 (s, 3H), 1.95-2.24 (m, 2H), 2.60-2.85 (m, 2H), 7.30 (d, J = 6.2 Hz, 2H), 7.30-7.43 (m, 4H), 8.41 (d, J = 6.2 Hz, 2H). |
| 55 | 1-(4-Bromo-2-fluorophenyl)-3-(4-methyl-2,5-dioxo-4-(pyridin-4-yl)ethyl)imidazolidin-1-yl)urea | Intermediate 30 4-bromo-2-fluoro-1-isocyanatobenzene CAS 88112-75-8 | $^1$HNMR (CD$_3$OD): δ 1.49 (s, 3H), 1.95-2.07 (m, 1H), 2.14-2.22 (m, 1H), 2.61-2.90 (m, 2H), 7.20-7.35 (m, 4H), 7.88 (t, J = 8.6 Hz, 1H), 8.39 (br s, 2H). |
| 56 | 1-(4-Bromophenyl)-3-(4-isopropyl-4-(((4-methoxybenzyl)oxy)methyl)-2,5-dioxoimidazolidin-1-yl)urea | Intermediate 39 1-bromo-4-isocyanatobenzene CAS 2493-02-9 | $^1$HNMR (CD$_3$OD): δ 0.84 (d, J = 7.3 Hz, 3H), 0.90 (d, J = 7.3 Hz, 3H), 1.99-2.14 (m, 1H), 3.57-3.70 (m, 2H), 3.77 (s, 3H), 4.41-4.47 (m, 2H), 6.86 (d, J = 8.5 Hz, 4H), 7.16-7.38 (m, 4H). |
| 57 | 1-(4-Bromo-2-fluorophenyl)-3-(4-isopropyl-4-(((4-methoxybenzyl)oxy)methyl)-2,5-dioxoimidazolidin-1-yl)urea | Intermediate 39 4-bromo-2-fluoro-1-isocyanatobenzene CAS 88112-75-8 | $^1$HNMR (CD$_3$OD): δ 0.96 (d, J = 7.3 Hz, 3H), 0.98 (d, J = 7.3 Hz, 3H), 1.99-2.18 (m, 1H), 3.57-3.70 |

TABLE 6-continued

| Comp. No. | IUPAC name | Starting material | ¹H NMR δ (ppm) for Compound |
|---|---|---|---|
| | [structure] | | (m, 2H), 3.75 (s, 3H), 4.45 (s, 2H), 6.84-6.88 (m, 3H), 7.15-7.33 (m, 4H) |
| 58 | Methyl 4-(2-(1-(3-(4-Bromophenyl)ureido)-4-methyl-2,5-dioxoimidazolidin-4-yl)ethyl)benzoate [structure] | Intermediate 41 1-bromo-4-isocyanatobenzene CAS 2493-02-9 | ¹HNMR (CD₃OD): δ 1.50 (s, 3H), 1.92-2.03 (m, 1H), 2.11-2.21 (m, 1H), 2.62-2.85 (m, 2H), 3.88 (s, 3H), 7.32 (d, J = 8.4 Hz, 2H), 7.35-7.43 (m, 4H), 7.93 (dd, J = 8.4, 1.8 Hz, 2H). |
| 59 | Methyl 2-(2-(1-(3-(4-bromophenyl)ureido)-4-methyl-2,5-dioxoimidazolidin-4-yl)ethyl)benzoate [structure] | Intermediate 42 1-bromo-4-isocyanatobenzene CAS 2493-02-9 | ¹HNMR (CD₃OD): δ 1.50 (s, 3H), 1.95-2.03 (m, 1H), 2.06-2.14 (m, 1H), 2.93 (br s, 1H), 3.08-3.16 (m, 1H), 3.89 (s, 3H), 7.27-7.31 (m, 2H), 7.35-7.42 (m, 4H), 7.47 (dt, J = 7.2, 1.2 Hz, 1H), 7.84 (d, J = 7.8 Hz, 1H). |
| 60 | Methyl 2-(2-(1-(3-(4-bromophenyl)ureido)-4-ethyl-2,5-dioxoimidazolidin-4-yl)ethyl)benzoate | Intermediate 43 1-bromo-4-isocyanatobenzene CAS 2493-02-9 | ¹HNMR (CD₃OD): δ 0.97 (t, J = 7.5 Hz, 3H), 1.65-2.15 (m, 4H), 2.90 (br s, 1H), |

TABLE 6-continued

| Comp. No. | IUPAC name | Starting material | $^1$H NMR δ (ppm) for Compound |
|---|---|---|---|
| | (structure: 4-ethyl-hydantoin with 2-(2-carbomethoxyphenyl)ethyl group and N-NH-C(O)-NH-(4-bromophenyl) urea) | | 3.01-3.15 (m, 1H), 3.89 (s, 3H), 7.23-7.50 (m, 7H), 7.83 (d, J = 7.7 Hz, 1H). |
| 61 | Methyl 2-(2-(1-(3-(4-bromo-2-fluorophenyl)ureido)-4-ethyl-2,5-dioxoimidazolidin-4-yl)ethyl)benzoate | Intermediate 43 4-bromo-2-fluoro-1-isocyanatobenzene CAS 88112-75-8 | $^1$HNMR (CD$_3$OD): δ 0.97 (t, J = 6.9 Hz, 3H), 1.70-2.16 (m, 4H), 2.94 (br s, 1H), 3.01-3.15 (m, 1H), 3.84 (s, 3H), 7.21-7.44 (m, 5H), 7.84 (dd, J = 8.4, 1.5 Hz, 1H), 7.91 (t, J = 8.4 Hz, 1H). |
| 62 | Ethyl 2-(1-(3-(4-bromo-2-fluorophenyl)ureido)-4-isopropyl-2,5-dioxoimidazolidin-4-yl)acetate | Intermediate 35 4-bromo-2-fluoro-1-isocyanatobenzene CAS 88112-75-8 | $^1$H NMR (CD$_3$OD): δ 0.89-1.01 (m, 6H), 1.19-1.27 (t, J = 7.5 Hz, 3H), 2.03-2.10 (m, 1H), 2.87-3.07 (m, 2H), 4.01-4.18 (m, 2H), 7.30 (d, J = 1.3 Hz, 1H), 7.36 (dd, J = 10.4, 2.2 Hz, 1H), 7.78-7.96 (m, 1H). |
| 63 | Ethyl 2-(1-(3-(4-bromophenyl)ureido)-4-isopropyl-2,5-dioxoimidazolidin-4-yl)acetate | Intermediate 35 1-bromo-4-isocyanatobenzene CAS 2493-02-9 | $^1$HNMR (CDCl$_3$): δ 0.96 (d, J = 7.5 Hz, 3H), 1.01 (d, J = 7.5 Hz, 3H), 1.29 (t, J = 7.4 Hz, 3H), 2.10 (sept, J = 7.5 Hz, 1H), 3.01 (m, 2H), 4.17 (m, 2H), 7.35 (d, J = 8.2 Hz, 2H), 7.42 (d, J = 8.2 Hz, 2H). |
| 64 | 1-(4-Bromophenyl)-3-[4-(1H-indol-3-ylmethyl)-4-methyl-2,5-dioxoimidazolidin-1-yl]urea | Intermediate 14 1-bromo-4-isocyanatobenzene CAS 2493-02-9 | $^1$H NMR (600 MHz, CD$_3$OD): δ 1.58 (s, 3H), 3.11 (d, J = 15.0 Hz, 1H), 3.31 (d, J = 15.0 |

TABLE 6-continued

| Comp. No. | IUPAC name | Starting material | $^1$H NMR δ (ppm) for Compound |
|---|---|---|---|
| | (structure) | | Hz, 1H), 7.01 (t, J = 8.4 Hz, 1H), 7.05 (t, J = 8.4 Hz, 1H), 7.28 (d, J = 8.4 Hz, 1H), 7.55 (d, J = 8.4 Hz, 1H). |
| 65 | 1-(4-Bromo-2-fluorophenyl)-3-[4-(5-ethyl-1H-indol-2-yl)-4-methyl-2,5-dioxoimidazolidin-1-yl]urea | Intermediate 19 4-bromo-2-fluoro-1-isocyanatobenzene CAS 88112-75-8 | $^1$H NMR (300 MHz, CD$_3$OD): δ 1.24 (t, J = 7.6 Hz, 3H), 1.94 (s, 3H), 2.68 (q, J = 7.6 Hz, 2H), 6.47 (s, 1H), 6.98 (dd, J = 8.2, 1.8 Hz, 1H), 7.31-7.34 (m, 4H), 7.91 (t, J = 8.6 Hz, 1H). |
| 66 | 1-(4-Bromophenyl)-3-(4,4-dicyclopropyl-2,5-dioxoimidazolidin-1-yl)urea | Intermediate 38 1-bromo-4-isocyanatobenzene CAS 2493-02-9 | $^1$H NMR (300 MHz, CD$_3$OD): δ 7.40 (dd, 4H), 4.88 (s, 3H), 1.25 (m, 2H), 0.63-0.41 (m, 8H) |
| 67 | 1-(4-Bromophenyl)-3-[2,5-dioxo-4,4-di(propan-2-yl)imidazolidin-1-yl]urea | Intermediate 37 1-bromo-4-isocyanatobenzene CAS 2493-02-9 | $^1$H NMR (300 MHz, CD$_3$OD): δ 7.40 (dd, 4H), 4.88 (s, 3H), 2.23 (sept, 2H), 1.05 (d, 6H), 1.00 (d, 6H). |
| 68 | Ethyl-3-[1-{[(4-bromophenyl)carbamoyl]-amino}-2,5-dioxo-4-(propan-2-yl)imidazolidin-4-yl]propanoate | Intermediate 36 1-bromo-4-isocyanatobenzene CAS 2493-02-9 | $^1$H NMR (300 MHz, CD$_3$OD): δ 0.98 (d, J = 7.5 Hz, 3H), 1.03 (d, J = 7.5 Hz, 3H), 1.24 (t, J = 7.2 Hz, 3H), 2.00-2.20 (m, 3H), 2.40 (br s, 2H), 4.12 (q, J = 7.2 Hz, 2H), 7.35 (d, J = 9.3 Hz, 2H), 7.40 (d, J = 9.3 Hz, 2H). |

TABLE 6-continued

| Comp. No. | IUPAC name | Starting material | ¹H NMR δ (ppm) for Compound |
|---|---|---|---|
| 69 | 1-(4-Bromophenyl)-3-(4,4-dimethyl-2,5-dioxo-3-phenylimidazolidin-1-yl)urea | Intermediate 40 1-bromo-4-isocyanatobenzene CAS 2493-02-9 | ¹H NMR (300 MHz, CDCl₃): δ 8.02 (s, 1H), 8.00 (s, 1H), 7.53-7.40 (m, 3H), 7.33-7.24 (m, 2H), 7.16 (d, 2H), 6.94 (d, 2H), 1.5 (s, 6H). |

Example 11

Compound 70

(−)-1-(4-Bromophenyl)-3-(4-methyl-2,5-dioxo-4-phenethylimidazolidin-1-yl)urea

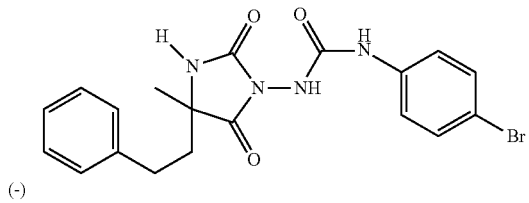

(−)

Compound 71

(+)-1-(4-Bromophenyl)-3-(4-methyl-2,5-dioxo-4-phenethylimidazolidin-1-yl)urea

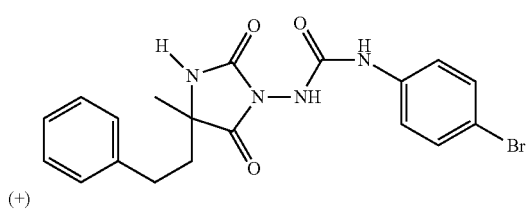 [SMILES: CC1(CCc2ccccc2)NC(=O)N(NC(=O)Nc2ccc(Br)cc2)C1=O]

(+)

Racemic Compound 9 was separated into the individual enantiomers Compound 70 and Compound 71, by chiral stationary phase high pressure liquid chromatography: preparative column (IC, 2×15 cm) and mobile phase (super critical fluid) 20% methanol (0.1% DEA)/CO₂, 100 bar; 70 mL/min, UV 220 nm.

(−) Enantiomer, peak 1, RT 0.86 min—Compound 70

$[\alpha]_D$=−16.52°, MeOH, c=0.0115 g/mL (+) Enantiomer, peak 2, RT 1.09 min—Compound 71

$[\alpha]_D$=+16.69°, MeOH, c=0.0115 g/Ml

Example 12

Compound 72

(+)-1-(4-Bromophenyl)-3-(4-ethyl-4-isopropyl-2,5-dioxoimidazolidin-1-yl)urea

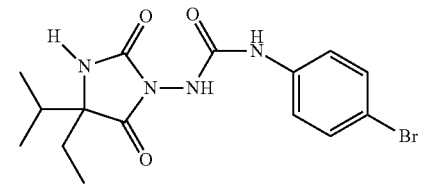

(+)

Compound 73

(+)-(4-Bromophenyl)-3-(4-ethyl-4-isopropyl-2,5-dioxoimidazolidin-1-yl)urea

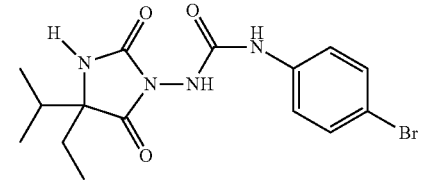

(−)

Racemic Compound 18 was separated into the individual enantiomers, Compound 72 and Compound 73, by chiral stationary phase high pressure liquid chromatography: preparative column (IA, 2×15 cm) and mobile phase (super critical fluid) 50% methanol (0.1% DEA)/CO₂, 100 bar; 70 mL/min, UV 254 nm.

(+) Enantiomer, peak 1, RT 2.22 min—Compound 72

$[\alpha]_D$=+15.9°, MeOH, c=0.9364 g/mL (−) Enantiomer, peak 2, RT 4.82 min—Compound 73

$[\alpha]_D$=−15.4°, MeOH, c=0.9182 g/mL

Example 13

Compound 74

1-(4-Bromophenyl)-3-(4-(hydroxymethyl)-4-isopropyl-2,5-dioxoimidazolidin-1-yl)urea

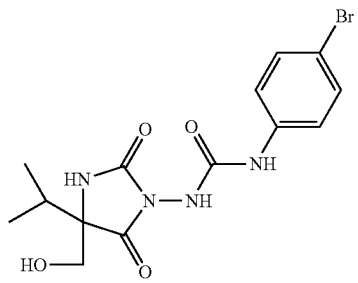 [SMILES: CC(C)C1(CO)NC(=O)N(NC(=O)Nc2ccc(Br)cc2)C1=O]

To a cold (0° C.) solution of Compound 56 (100 mg, 0.2 mmol) in $CH_2Cl_2$ (5 mL) was added DDQ, CAS 84-58-2 (100 mg, 0.4 mmol) and stirred for 90 min. To the reaction saturated sodium thiosulfate (2 mL) was added and stirred for 30 min. The solvent removed under reduced pressure and purified by silicagel chromatography using MeOH in $CH_2Cl_2$. The product was obtained as a white solid.

$^1$HNMR (CD$_3$OD): δ 0.98 (d, J=7.0 Hz, 6H), 2.06-2.20 (m, 1H), 3.75-3.90 (m, 2H), 7.31-7.41 (m, 4H).

Compounds 75 and 76 were prepared in a similar manner to the procedure described in Example 13 for Compound 74. The starting materials used and the results are tabulated below in Table 7.

TABLE 7

| Comp. No. | IUPAC name | Starting material | $^1$H NMR δ (ppm) for Compound |
|---|---|---|---|
| 75 | 1-(4-Bromophenyl)-3-(4-(2-hydroxyethyl)-4-isopropyl-2,5-dioxoimidazolidin-1-yl)urea | Compound 49 | $^1$H NMR (CD$_3$OD): δ 0.96 (brs, 3H), 1.01 (d, J = 7.2 Hz, 3H), 1.95-2.10 (m, 2H), 2.18 (br s, 1H), 3.72 (br s, 2H), 7.34-7.40 (m, 4H).. |
| 76 | 1-(4-Bromo-2-fluorophenyl)-3-(4-(2-hydroxymethyl)-4-isopropyl-2,5-dioxoimidazolidin-1-yl)urea | Compound 57 | $^1$H NMR (CD$_3$OD): δ 0.98 (d, J = 6.7 Hz, 3H), 1.00 (d, J = 6.7 Hz, 3H), 2.08-2.19 (m, 1H), 3.73-3.87 (m, 2H), 7.26 (dt, J = 8.8, 1.6 Hz, 1H), 7.34 (dd, J = 10.6, 2.1 Hz, 1H), 7.87 (t, J = 8.6 Hz, 1H). |

Example 14

Compound 77

4-(2-(1-(3-(4-Bromophenyl)ureido)-4-methyl-2,5-dioxoimidazolidin-4-yl)ethyl)benzoic acid

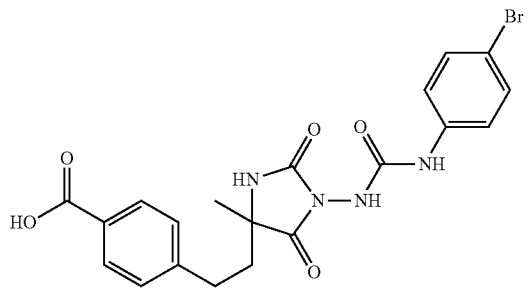 [SMILES: CC1(CCc2ccc(C(=O)O)cc2)NC(=O)N(NC(=O)Nc2ccc(Br)cc2)C1=O]

To a solution of Compound 58 (30 mg, 0.06 mmol) in dioxane (2 mL) was added KOH—H$_2$O (0.5M solution, 1 mL) was added and stirred at RT for 90 min. Solvent was removed under reduced pressure, then the reaction was cooled (0° C.) and acidified to pH 2 with 10% HCl. The crude product was purified by silicagel chromatography using MeOH in CH$_2$Cl$_2$. Compound 77 was isolated as a white solid.

$^1$HNMR (CD$_3$OD): δ 1.50 (s, 3H), 1.92-2.03 (m, 1H), 2.11-2.21 (m, 1H), 2.62-2.85 (m, 2H), 7.32 (d, J=7.8 Hz, 2H), 7.35-7.45 (m, 4H), 7.92-7.97 (m, 2H).

Compounds 78 through 83 were prepared in a similar manner to the procedure described in Example 14 for Compound 77. The starting materials used and the results are tabulated below in Table 8.

TABLE 8

| Comp. No. | IUPAC name | | Starting material | $^1$H NMR δ (ppm) for Compound |
|---|---|---|---|---|
| 78 | 2-(2-(1-(3-(4-Bromophenyl)ureido)-4-methyl-2,5-dioxoimidazolidin-4-yl)ethyl)benzoic acid | | Compound 59 | $^1$H NMR (CD$_3$OD): δ 1.50 (s, 3H), 1.95-2.10 (m, 2H), 2.90 (br s, 1H), 3.15 (br s, 1H), 7.25-7.35 (m, 2H), 7.37-7.49 (m, 5H), 7.84 (d, J = 7.8 Hz, 1H). |
| 79 | 2-(2-(1-(3-(4-Bromophenyl)ureido)-4-ethyl-2,5-dioxoimidazolidin-4-yl)ethyl)benzoic acid | | Compound 60 | $^1$H NMR (CD$_3$OD): δ 0.96 (t, J = 7.5 Hz, 3H), 1.75-2.20 (m, 4H), 2.90 (br s, 1H), 2.20 (br s, 1H), 7.20-7.50 (m, 7H), 7.88 (d, J = 7.7 Hz, 1H). |

TABLE 8-continued

| Comp. No. | IUPAC name | Starting material | $^1$H NMR δ (ppm) for Compound |
|---|---|---|---|
| 80 | Methyl 2-(2-(1-(3-(4-bromo-2-fluorophenyl)ureido)-4-ethyl-2,5-dioxoimidazolidin-4-yl)ethyl)benzoate | Compound 61 | $^1$H NMR (CD$_3$OD): δ 0.97 (t, J = 7.5 Hz, 3H), 1.70-2.15 (m, 4H), 2.90 (br s, 1H), 3.10-3.25 (m, 1H), 7.22-7.48 (m, 5H), 7.83-7.96 (m, 2H). |
| 81 | 2-(1-(3-(4-Bromophenyl)ureido)-4-isopropyl-2,5-dioxoimidazolidin-4-yl)acetic acid | Compound 63 | $^1$H NMR (CD$_3$OD): δ 0.98 (d, J = 7.5 Hz, 3H), 1.03 (d, J = 7.5 Hz, 3H), 2.07 (sept, J = 7.5 Hz, 1H), 3.02 (m, 2H), 7.41 (d, J = 8.2 Hz, 2H), 7.50 (d, J = 8.2 Hz, 2H). |
| 82 | 2-(1-(3-(4-Bromo-2-fluorophenyl)ureido)-4-isopropyl-2,5-dioxoimidazolidin-4-yl)acetic acid | Compound 62 | $^1$H NMR (CD$_3$OD): δ 0.97-1.08 (m, 6H), 2.00-2.14 (m, 1H), 2.94 (d, J = 9.9 Hz, 2H), 7.29 (d, J = 1.3 Hz, 1H), 7.34 (10.3, 2.2 Hz, 1H), 7.67-7.89 (m, 1H). |
| 83 | 3-[1-{[(4-bromophenyl)carbamoyl]amino}-2,5-dioxo-4-(propan-2-yl)imidazolidin-4-yl]propanoic acid | Compound 68 LiOH | $^1$H NMR (300 MHz, CD$_3$OD): δ 0.98 (d, J = 6.6 Hz, 3H), 1.03 (d, J = 6.6 Hz, 3H), 2.00-2.20 (m, 3H), 2.40 (br s, 2H), 7.35 (d, J = 9.3 Hz, 2H), 7.40 (d, J = 9.3 Hz, 2H) |

Example 15

Compound 84

2-(1-(3-(4-Bromophenyl)ureido)-4-isopropyl-2,5-dioxoimidazolidin-4-yl)-N-(2-hydroxyethyl)acetamide

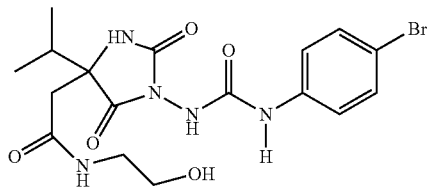 [SMILES: CC(C)C1(CC(=O)NCCO)NC(=O)N(NC(=O)Nc2ccc(Br)cc2)C1=O]

To a solution of Compound 81 (50 mg, 0.12 mmol) in $CH_2Cl_2$ (5 mL) was added ethanolamine (15 mg, 0.24 mmol), propyl propionic anhydride (0.1 mL, 50% wt/wt in EtOAc), $Et_3N$ (61 mg, 0.6 mmol), DMAP (4 mg) and stirred at RT for 18 h. The solvent was removed on rotavapor and the crude reaction was purified by Preparative Thin layer chromatography. Compound 84 was isolated as white solid.

$^1$H NMR ($CD_3OD$) δ 0.90-1.08 (m, 6H), 1.97-2.09 (m, 1H), 2.92 (d, J=9.4 Hz, 2H), 3.52-3.66 (m, 4H), 7.31-7.47 (m, 2H), 7.56 (br. s, 2H).

Compounds 85 through 91 were prepared in a similar manner to the procedure described in Example 15 for Compound 84. The starting materials used and the results are tabulated below in Table 9.

TABLE 9

| Comp. No. | IUPAC name | Starting material | $^1$H NMR δ (ppm) for Compound |
|---|---|---|---|
| 85 | tert-Butyl 2-(2-(1-(3-(4-bromophenyl)ureido)-4-isopropyl-2,5-dioxoimidazolidin-4-yl)acetamido)acetate | Compound 81 1-Ethyl-3-(3-dimethylamino-propyl)carbodiimide CAS 52399-93-6 | $^1$H NMR ($CD_3OD$) δ 0.94 (d, J = 6.6 Hz, 3H), 1.03 (d, J = 6.8 Hz, 3H), 1.37 (s, 9H), 1.96-2.09 (m, 1H), 2.88-3.07 (m, 2H), 3.84-3.95 (m, 2H), 7.38 (d, J = 8.9 Hz, 2H), 7.45-7.65 (m, 2H). |
| 86 | Diethyl ((2-(1-(3-(4-bromophenyl)ureido)-4-isopropyl-2,5-dioxoimidazolidin-4-yl)acetamido)methyl)phosphonate | Compound 81 | $^1$H NMR ($CD_3OD$) δ 0.88-1.08 (m, 6H), 1.25 (q, J = 6.9 Hz, 6H), 1.94-2.11 (m, 1H), 2.96 (br.s, 2H), 3.57-3.84 (m 2H), 4.06 (quin., J = 7.3 Hz, 4H), 7.40 (d, J = 8.9 Hz, 2H), 7.56 (br. s, 2H). |
| 87 | 2-(1-(3-(4-Bromophenyl)ureido)-4-isopropyl-2,5-dioxoimidazolidin-4-yl)-N,N-bis(2-hydroxyethyl)acetamide | Compound 81 | $^1$H NMR ($CD_3OD$) δ 0.88-0.98 (m, 3H), 0.98-1.10 (m, 3H), 1.93-2.10 (m, 1H), 2.86-3.05 (m, 2H), 3.54-3.70 (m, 4H), 3.85-4.00 (m, 4H), 7.31-7.45 (m, 2H), 7.48-7.6 (m, 2H). |

TABLE 9-continued

| Comp. No. | IUPAC name | Starting material | $^1$H NMR δ (ppm) for Compound |
|---|---|---|---|
| 88 | Diisopropyl ((2-(1-(3-(4-bromophenyl)ureido)-4-isopropyl-2,5-dioxoimidazolidin-4-yl)acetamido)methyl)phosphonate | Compound 81 | $^1$H NMR (CD$_3$OD) δ 0.88-1.07 (m, 6H), 1.21-1.33 (m, 12H), 1.95-2.10 (m, 1H), 2.97 (br. s, 2H), 3.55-3.77 (m, 2H), 4.54-4.72 (m, 2H), 7.40 (d, J = 8.9 Hz, 2H), 7.55-7.63 (m, 2H). |
| 89 | Ethyl hydrogen((2-(1-(3-(4-bromophenyl)ureido)-4-isopropyl-2,5-dioxoimidazolidin-4-yl)acetamido)methyl)phosphonate | Compound 86 LiOH | $^1$H NMR (CD$_3$OD) δ 0.89-0.96 (m, 3H), 1.03 (d, J = 6.8 Hz, 3H), 1.10-1.18 (m 3H), 1.94-2.06 (m, 1H), 2.89-2.99 (m, 2H), 3.25-3.31 (m, 2H), 3.74-3.88 (m, 2H), 7.41 (d, J = 8.9 Hz, 4H). |
| 90 | tert-Butyl 2-(2-(1-(3-(4-bromophenyl)ureido)-4-isopropyl-2,5-dioxoimidazolidin-4-yl)acetamido)2-methylpropanoate | Compound 81 | $^1$H NMR (CD$_3$OD) δ 0.94 (d, J = 6.7 Hz, 3H), 1.02 (d, J = 6.7 Hz, 3H), 1.33 (9H), 1.45 (s, 3H), 1.47 (s, 3H), 1.93-2.09 (m, 1H), 2.91 (s, 2H), 7.37 (d, J = 8.9 Hz, 2H), 7.50-7.61 (m, 2H). |

TABLE 9-continued

| Comp. No. | IUPAC name | Starting material | $^1$H NMR δ (ppm) for Compound |
|---|---|---|---|
| 91 | tert-Butyl 3-(2-(1-(3-(4-bromophenyl)ureido)-4-isopropyl-2,5-dioxoimidazolidin-4-yl)acetamido)propanoate | Compound 81 | $^1$H NMR (CD$_3$OD) δ 0.93 (d, J = 6.6 Hz, 3H), 1.01 (d, J = 6.8 Hz, 3H), 1.41 (s, 9H), 1.94-2.08 (m, 1H), 2.41-2.44 (m, 2H), 2.78-2.96 (m, 2H), 2.34-3.49 (m, 2H), 7.39 (d, J = 8.9 Hz, 2H), 7.54-7.66 (m, 2H). |

Example 16

Compound 92

2-(2-(1-(3-(4-Bromophenyl)ureido)-4-isopropyl-2,5-dioxoimidazolidin-4-yl)acetamido)acetic acid

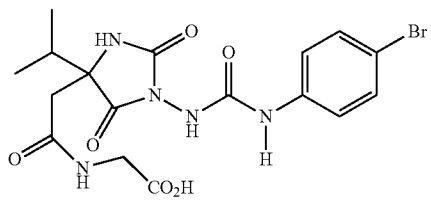

To Compound 85 (131 mg, 0.23 mmol) was added formic acid (3 mL) and stirred at RT for 1 h. The solvent was removed at RT under vacuum. Compound 92 was isolated as white solid.

$^1$H NMR (CD$_3$OD) δ 0.94 (d, J=6.5 Hz, 3H), 1.03 (d, J=6.9 Hz, 3H), 2.03 (m, 1H), 3.00 (d, J=6.2 Hz, 2H), 3.90 (d, J=4.4 Hz, 2H), 7.37 (d, J=8.9 Hz, 2H), 7.47-7.60 (m, 2H).

Compounds 93 through 96 were prepared in a similar manner to the procedure described in Example 16 for Compound 92. The starting materials used and the results are tabulated below in Table 10.

TABLE 10

| Comp. No. | IUPAC name | Starting material | $^1$H NMR δ (ppm) for Compound |
|---|---|---|---|
| 93 | 3-(2-(1-(3-(4-Bromophenyl)ureido)-4-isopropyl-2,5-dioxoimidazolidin-4-yl)acetamido)propanoic acid | Compound 91 | $^1$H NMR (CD$_3$OD) δ: 0.93 (d, J = 6.6 Hz, 3H), 1.01 (d, J = 6.8 Hz, 3H), 1.94-2.08 (m, 1H), 2.43 (m, 2H), 2.78-2.96 (m, 2H), 3.34-3.49 (m, 2H), 7.39 (d, J = 8.9 Hz, 2H), 7.54-7.66 (m, 2H). |
| 94 | 3-(2-(1-(3-(4-bromo-2-fluorophenyl)ureido)-4-isopropyl-2,5-dioxoimidazolidin-4-yl)acetamido)propanoic acid | Compound 82 (in 2 steps) | $^1$H NMR (CD$_3$OD) δ: 0.97-1.08 (m, 6H), 1.97-2.09 (m, 1H), 2.80-2.92 (m, 2H), 3.20-3.30 (m, 2H), 3.51-3.59 (m, 2H), 7.27-7.37 (m, 2H), 7.66 (br. s, 1H). |

TABLE 10-continued

| Comp. No. | IUPAC name | Starting material | $^1$H NMR δ (ppm) for Compound |
|---|---|---|---|
| 95 | 2-(2-(1-(3-(4-Bromophenyl)ureido)-4-isopropyl-2,5-dioxoimidazolidin-4-yl)acetamido)2-methylpropanoic acid 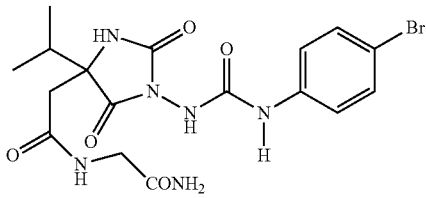 [SMILES: CC(C)C1(CC(=O)NCC(N)=O)NC(=O)N(NC(=O)Nc2ccc(Br)cc2)C1=O] | Compound 90 | $^1$H NMR (CD$_3$OD) δ: 0.88-1.06 (m, 6H), 1.45 (s, 3H), 1.47 (s, 3H), 1.90-2.08 (m, 1H), 2.92 (s, 2H), 7.31-7.44 (m, 2H), 7.56 (d, J = 7.8 Hz, 2H). |

Example 17

Compound 96

N-(2-Amino-2-oxoethyl)-2-(1-(3-(4-bromophenyl)ureido)-4-isopropyl-2,5-dioxoimidazolidin-4-yl)acetamide To a cold (−31° C.) turbid mixture of Compound 92 (180 mg, 0.38 mmol) in THF (5 mL) was added Et$_3$N (118 mg, 1.18 mmol). After 5 min ClCO$_2$Et (66 mg, 0.61 mmol) was added and stirred for 20 min. NH$_3$ gas was bubbled through the reaction mixture. Then the reaction was gradually warmed to RT. The crude reaction was purified by silicagel chromatography eluting with 10% MeOH in CH$_2$Cl$_2$. The product was then washed with 10% HCl to remove basic impurities in the product. The Compound 96 was isolated as a white solid.

$^1$H NMR (METHANOL-d$_4$) δ 0.95 (d, J=6.6 Hz, 3H), 1.03 (d, J=6.9 Hz, 3H), 1.94-2.12 (m, 1H), 2.88-3.14 (m, 2H), 3.84 (d, J=11.0 Hz, 2H), 7.33-7.47 (m, 2H), 7.49-7.63 (m, 2H).

Biological Data

Biological activity of compounds according to Formula I is set forth in Table 11 below. HEK-Gα16 and CHO-Gα16 cells stably expressing FPRL1 were cultured in (F12, 10% FBS, 1% PSA, 400 μg/ml geneticin and 50 μg/ml hygromycin) and HEK-Gqi5 cells stable expressing FPR1 were cultured in (DMEM high glucose, 10% FBS, 1% PSA, 400 μg/ml geneticin and 50 μg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 11

| Compound IUPAC name | FPRL-1 Ga16-CHO EC$_{50}$ (% eff) |
|---|---|
| 1-(4-Chlorophenyl)-3-(4,4-diethyl-2,5-dioxoimidazolidin-1-yl)urea | 27 nM (1.0) |
| 1-(4-Bromophenyl)-3-(4,4-diethyl-2,5-dioxoimidazolidin-1-yl)urea | 9.1 nM (1.0) |
| 1-(4-Methoxyphenyl)-3-(4,4-diethyl-2,5-dioxoimidazolidin-1-yl)urea | 194 nM (1.0) |
| 1-(4-Ethylphenyl)-3-(4,4-diethyl-2,5-dioxoimidazolidin-1-yl)urea | 125 nM (1.0) |
| 1-(4-Cyanophenyl)-3-(4,4-diethyl-2,5-dioxoimidazolidin-1-yl)urea | 1229 nM (1.0) |
| 1-(4-Bromo-2-fluorophenyl)-3-(4,4-diethyl-2,5-dioxoimidazolidin-1-yl)urea | 15.6 nM (1.0) |
| 1-(4-Methylphenyl)-3-(4,4-diethyl-2,5-dioxoimidazolidin-1-yl)urea | 96.0 nM (1.0) |
| 1-(4-Methylthiophenyl)-3-(4,4-diethyl-2,5-dioxoimidazolidin-1-yl)urea | 37.1 nM (1.0) |
| 1-(4-Bromo-2-fluorophenyl)-3-(2,4-dioxo-1,3-diazaspiro[4.5]decan-3-yl)urea | 233 nM (1.0) |
| 1-(4-Bromophenyl)-3-(2,4-dioxo-1,3-diazaspiro[4.5]decan-3-yl)urea | 13.6 nM (1.0) |
| 1-(4-Chloro-2-fluorophenyl)-3-(4,4-diethyl-2,5-dioxoimidazolidin-1-yl)urea | 39 nM (0.98) |
| 1-(4-Bromo-2-fluorophenyl)-3-(2,4-dioxo-1,3-diazaspiro[4.4]nonan-3-yl)urea | 23.9 nM (0.89) |
| 1-(4-Bromophenyl)-3-(4,4-dimethyl-2,5-dioxoimidazolidin-1-yl)urea | 74.9 nM (1.0) |
| 1-(4-Bromophenyl)-3-(4-methyl-2,5-dioxo-4-phenethylimidazolidin-1-yl)urea | 5.1 nM (0.87) |
| 1-(4-Bromo-2-fluorophenyl)-3-(4-methyl-2,5-dioxo-4-phenethylimidazolidin-1-yl)urea | 61.0 nM (0.88) |
| (−)-1-(4-Bromophenyl)-3-(4-methyl-2,5-dioxo-4-phenethylimidazolidin-1-yl)urea | 22 nM (0.92) |
| (+)-1-(4-Bromophenyl)-3-(4-methyl-2,5-dioxo-4-phenethylimidazolidin-1-yl)urea | 2.4 nM (0.83) |
| 1-(4-Bromophenyl)-3-(4-ethyl-4-isopropyl-2,5-dioxoimidazolidin-1-yl)urea | 6.3 nM (0.91) |
| 1-(4-Bromophenyl)-3-(2,5-dioxo-1',3'-dihydrospiro[imidazolidine-4,2'-inden]-1-yl)urea | 47 nM (0.89) |
| 1-(4-Chloro-3-fluorophenyl)-3-(4,4-diethyl-2,5-dioxoimidazolidin-1-yl)urea | 149 nM (0.97) |
| 1-(4-Bromo-2-fluorophenyl)-3-(4-ethyl-4-isopropyl-2,5-dioxoimidazolidin-1-yl)urea | 6.3 nM (1.0) |
| (+)-1-(4-Bromophenyl)-3-(4-ethyl-4-isopropyl-2,5-dioxoimidazolidin-1-yl)urea | 4.3 nM (0.96) |

TABLE 11-continued

| Compound IUPAC name | FPRL-1 Gal6-CHO EC$_{50}$ (% eff) |
|---|---|
| (−)-1-(4-Bromophenyl)-3-(4-ethyl-4-isopropyl-2,5-dioxoimidazolidin-1-yl)urea | 3.3 nM (1.0) |
| 1-(4-Bromophenyl)-3[4-methyl-2,5-dioxo-4-(phenoxymethyl)imidazolidin-1-yl]urea | 22.1 (0.99) |
| 1-(4-Bromophenyl)-3[2,5-dioxo-4,4-di(propan-2-yl)imidazolidin-1-yl]urea | <2 (0.98) |
| 1-(4-Bromophenyl)-3-(4,4-dicyclopropyl-2,5-dioxoimidazolidin-1-yl)urea | 14.3 (1.00) |
| 1-(4-Bromo-2-fluorophenyl)-3-(2,5-dioxo-3',4'-dihydro-1H,1'H-spiro[imidazolidine-4,2'-naphthalen]-1-yl)urea | 191.1 (0.92) |
| 1-(4-Bromo-2-fluorophenyl)-3[4-methyl-2,5-dioxo-4-(phenoxymethyl)imidazolidin-1-yl]urea | 52.1 (0.96) |
| 1-(4-Bromophenyl)-3-(2,5-dioxo-3',4'-dihydro-1H,1'H-spiro[imidazolidine-4,2'-naphthalen]-1-yl)urea | 53.5 (1.00) |
| 1-(4-Bromo-2-fluorophenyl)-3[4-ethyl-2,5-dioxo-4-(2-phenylethyl)imidazolidin-1-yl]urea | <2 (0.91) |
| 1-(4-Bromophenyl)-3[4-ethyl-2,5-dioxo-4-(2-phenylethyl)imidazolidin-1-yl]urea | 0.5 (1.00) |
| 1-(4-Bromophenyl)-3[4-(2-methylpropyl)-2,5-dioxo-4-(2-phenylethyl)imidazolidin-1-yl]urea | 86.4 (0.90) |
| 1-(4-Bromo-2-fluorophenyl)-3[4-(2-methylpropyl)-2,5-dioxo-4-(2-phenylethyl)imidazolidin-1-yl]urea | 105.3 (1.00) |
| 1-(4-Bromophenyl)-3-{4-[2-(4-chlorophenyl)ethyl]-4-methyl-2,5-dioxoimidazolidin-1-yl}urea | 333.4 (0.86) |
| 1-(4-Bromo-2-fluorophenyl)-3-{4-[2-(4-chlorophenyl)ethyl]-4-methyl-2,5-dioxoimidazolidin-1-yl}urea | 1381 (0.77) |
| 1-(4-Bromophenyl)-3-{4-[2-(furan-2-yl)ethyl]-4-methyl-2,5-dioxoimidazolidin-1-yl}urea | 6.9 (1.00) |
| 1-(4-Bromo-2-fluorophenyl)-3-{4-[2-(furan-2-yl)ethyl]-4-methyl-2,5-dioxoimidazolidin-1-yl}urea | 39.8 (0.99) |
| 1-(4-Bromophenyl)-3-{4-[2-(2-fluorophenyl)ethyl]-4-methyl-2,5-dioxoimidazolidin-1-yl}urea | 14 (0.99) |
| 1-(4-Bromophenyl)-3-{4-[2-(4-fluorophenyl)ethyl]-4-methyl-2,5-dioxoimidazolidin-1-yl}urea | 17 (1.00) |
| 1-(4-Bromophenyl)-3-[4-(1H-indol-3-ylmethyl)-4-methyl-2,5-dioxoimidazolidin-1-yl]urea | 113.7 (1.00) |
| 1-(4-Bromo-2-fluorophenyl)-3-{4-[2-(2-fluorophenyl)ethyl]-4-methyl-2,5-dioxoimidazolidin-1-yl}urea | 56.2 (0.86) |
| 1-(4-Bromo-2-fluorophenyl)-3-{4-[2-(4-fluorophenyl)ethyl]-4-methyl-2,5-dioxoimidazolidin-1-yl}urea | 117.9 (0.87) |
| 1-(4-Bromophenyl)-3-{4-[2-(3-fluorophenyl)ethyl]-4-methyl-2,5-dioxoimidazolidin-1-yl}urea | 11.1 (1.00) |
| 1-(4-Bromophenyl)-3-{4-[2-(4-hydroxyphenyl)ethyl]-4-methyl-2,5-dioxoimidazolidin-1-yl}urea | 13.3 (1.00) |
| 1-(4-Bromo-2-fluorophenyl)-3-{4-methyl-2,5-dioxo-4[2-(thiophen-2-yl)ethyl]imidazolidin-1-yl}urea | 86 (1.00) |
| 1-(4-Bromophenyl)-3-{4-methyl-2,5-dioxo-4-[2-(thiophen-2-yl)ethyl]imidazolidin-1-yl}urea | 7.9 (0.94) |
| 1-(4-Bromo-2-fluorophenyl)-3-{4-[2-(4-hydroxyphenyl)ethyl]-4-methyl-2,5-dioxoimidazolidin-1-yl}urea | 8.7 (0.85) |
| 1-(4-Bromo-2-fluorophenyl)-3[4-(5-ethyl-1H-indol-2-yl)-4-methyl-2,5-dioxoimidazolidin-1-yl]urea | 169.4 (0.88) |
| 1-(4-Bromophenyl)-3-{4-methyl-4-[2-(5-methylfuran-2-yl)ethyl]-2,5-dioxoimidazolidin-1-yl}urea | 3.5 (0.95) |
| 1-(4-Bromo-2-fluorophenyl)-3-{4-[2-(3-fluoro-4-hydroxyphenyl)ethyl]-4-methyl-2,5-dioxoimidazolidin-1-yl}urea | 7.4 (0.91) |
| 1-(4-Bromophenyl)-3-{4-[2-(3-fluoro-4-hydroxyphenyl)ethyl]-4-methyl-2,5-dioxoimidazolidin-1-yl}urea | 7.9 (1.00) |
| 1-(4-Bromo-2-fluorophenyl)-3-{4-[2-(2-hydroxyphenyl)ethyl]-4-methyl-2,5-dioxoimidazolidin-1-yl}urea | 5.8 (0.85) |
| 1-(4-Bromo-2-fluorophenyl)-3-{4-[2-(3-hydroxyphenyl)ethyl]-4-methyl-2,5-dioxoimidazolidin-1-yl}urea | 2.9 (0.79) |
| 1-(4-Bromophenyl)-3-{4-[2-(3-hydroxyphenyl)ethyl]-4-methyl-2,5-dioxoimidazolidin-1-yl}urea | 1.5 (0.98) |
| 1-(4-Bromophenyl)-3-[4-{2-[(4-methoxybenzyl)oxy]ethyl}-2,5-dioxo-4-(propan-2-yl)imidazolidin-1-yl]urea | 232.1 (0.93) |
| 1-(4-Bromophenyl)-3-{4-[2-(2-hydroxyphenyl)ethyl]-4-methyl-2,5-dioxoimidazolidin-1-yl}urea | 0.97 (0.93) |
| Methyl-4-[2-(1-{[(4-bromophenyl)carbamoyl]amino}-4-methyl-2,5-dioxoimidazolidin-4-yl)ethyl]benzoate | 204.4 (0.96) |
| 4-[2-(1-{[(4-Bromophenyl)carbamoyl]amino}-4-methyl-2,5-dioxoimidazolidin-4-yl)ethyl]benzoic acid | 210.1 (0.99) |
| 1-(4-Bromophenyl)-3-{4-methyl-2,5-dioxo-4-[2-(pyridin-4-yl)ethyl]imidazolidin-1-yl}urea | 30.2 (1.00) |
| 1-(4-Bromo-2-fluorophenyl)-3-{4-methyl-2,5-dioxo-4-[2-(pyridin-4-yl)ethyl]imidazolidin-1-yl}urea | 28.6 (0.98) |
| Methyl-2-[2-(1-{[(4-bromophenyl)carbamoyl]amino}-4-methyl-2,5-dioxoimidazolidin-4-yl)ethyl]benzoate | 28.9 (1.00) |
| 2-[2-(1-{[(4-Bromophenyl)carbamoyl]amino}-4-methyl-2,5-dioxoimidazolidin-4-yl)ethyl]benzoic acid | 17.19 (1.02) |
| 3-(2-(1-(3-(4-Bromophenyl)ureido)-4-isopropyl-2,5-dioxoimidazolidin-4-yl)acetamido)propanoic acid | 5.16 (0.97) |
| tert-Butyl 3-({[1-{[(4-bromophenyl)carbamoyl]amino}-2,5-dioxo-4-(propan-2-yl)imidazolidin-4-yl]acetyl}amino)propanoate | 79.06 (0.86) |
| 2-[2-(1-{[(4-Bromo-2-fluorophenyl)carbamoyl]amino}-4-ethyl-2,5-dioxoimidazolidin-4-yl)ethyl]benzoic acid | 11.06 (1.03) |
| 2-({[1-{[(4-Bromophenyl)carbamoyl]amino}-2,5-dioxo-4-(propan-2-yl)imidazolidin-4-yl]acetyl}amino)-2-methylpropanoic acid | 109.12 (1.00) |
| Methyl-2-[2-(1-{[(4-bromo-2-fluorophenyl)carbamoyl]amino}-4-ethyl-2,5-dioxoimidazolidin-4-yl)ethyl]benzoate | 14.93 (0.92) |
| [1-{[(4-Bromo-2-fluorophenyl)carbamoyl]amino}-2,5-dioxo-4-(propan-2-yl)imidazolidin-4-yl]acetic acid | 712.91 (0.93) |
| 2-[1-{[(4-Bromophenyl)carbamoyl]amino}-2,5-dioxo-4-(propan-2-yl)imidazolidin-4-yl]-N-(1,3-dihydroxypropan-2-yl)acetamide | 16.16 (0.94) |
| Methyl-2-[2-(1-{[(4-bromophenyl)carbamoyl]amino}-4-ethyl-2,5-dioxoimidazolidin-4-yl)ethyl]benzoate | 10.28 (0.92) |
| Ethyl hydrogen [({[1-{[(4-bromophenyl)carbamoyl]amino}-2,5-dioxo-4-(propan-2-yl)imidazolidin-4-yl]acetyl}amino)methyl]phosphonate | 313.28 (1.07) |
| N-(2-Amino-2-oxoethyl)-2-[1-{[(4-bromophenyl)carbamoyl]amino}-2,5-dioxo-4-(propan-2-yl)imidazolidin-4-yl]acetamide | 51.28 (1.05) |
| ({[1-{[(4-Bromophenyl)carbamoyl]amino}-2,5-dioxo-4-(propan-2-yl)imidazolidin-4-yl]acetyl}amino)acetic acid | 132.65 (0.9) |
| di-Propan-2-yl [({[1-{[(4-bromophenyl)carbamoyl]amino}-2,5-dioxo-4-(propan-2-yl)imidazolidin-4-yl]acetyl}amino)methyl]phosphonate | 192.98 (0.87) |
| tert-Butyl ({[1-{[(4-bromophenyl)carbamoyl]amino}-2,5-dioxo-4-(propan-2-yl)imidazolidin-4-yl]acetyl}amino)acetate | 301.77 (1.01) |
| di-Ethyl [({[1-{[(4-bromophenyl)carbamoyl]amino}-2,5-dioxo-4-(propan-2-yl)imidazolidin-4-yl]acetyl}amino)methyl]phosphonate | 271.74 (0.83) |
| 2-[1-{[(4-Bromophenyl)carbamoyl]amino}-2,5-dioxo-4-(propan-2-yl)imidazolidin-4-yl]-N-(2-hydroxyethyl)acetamide | 16.2 (0.86) |
| 1-(4-Bromophenyl)-3[4-(hydroxymethyl)-2,5-dioxo-4-(propan-2-yl)imidazolidin-1-yl]urea | 2.65 (1.01) |

TABLE 11-continued

| Compound IUPAC name | FPRL-1 Ga16-CHO EC$_{50}$ (% eff) |
|---|---|
| 1-(4-Bromo-2-fluorophenyl)-3[4-(hydroxymethyl)-2,5-dioxo-4-(propan-2-yl)imidazolidin-1-yl]urea | 50 (1.03) |
| 1-(4-Bromophenyl)-3-{4-[2-(3-hydroxyphenyl)ethyl]-4-methyl-2,5-dioxoimidazolidin-1-yl}urea | 2.07 (1.01) |
| [1-{[(4-Bromophenyl)carbamoyl]amino}-2,5-dioxo-4-(propan-2-yl)imidazolidin-4-yl]acetic acid | 459.42 (0.8) |
| 1-(4-Bromophenyl)-3-[4-(2-hydroxyethyl)-2,5-dioxo-4-(propan-2-yl)imidazolidin-1-yl]urea | 21.21 (0.95) |
| 3-(4-Bromophenyl)-5-(5-ethyl-1H-indol-2-yl)-5-methylimidazolidine-2,4-dione | 2588.94 (0.77) |

What is claimed is:

1. A compound represented by Formula I, its enantiomers, diastereoisomers, hydrates, solvates or a pharmaceutically acceptable salt thereof:

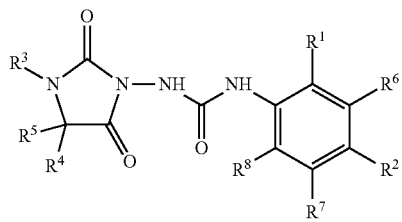

Formula I wherein $R^1$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;

$R^2$ is halogen, optionally substituted $C_{1-8}$ alkyl, $CF_3$, $OR^9$, $C(O)R^{10}$, $NO_2$, $NR^{13}R^{14}$, CN, $SR^{15}$ or $SO_2R^{16}$;

$R^3$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a 5- or 6-membered ring which is optionally substituted;

$R^4$ is hydrogen, optionally substituted $C_{1-8}$ alkyl,

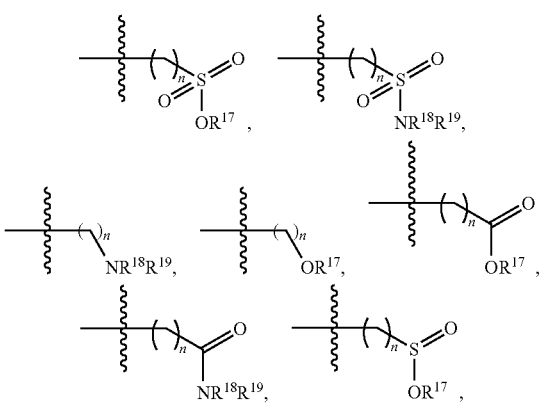

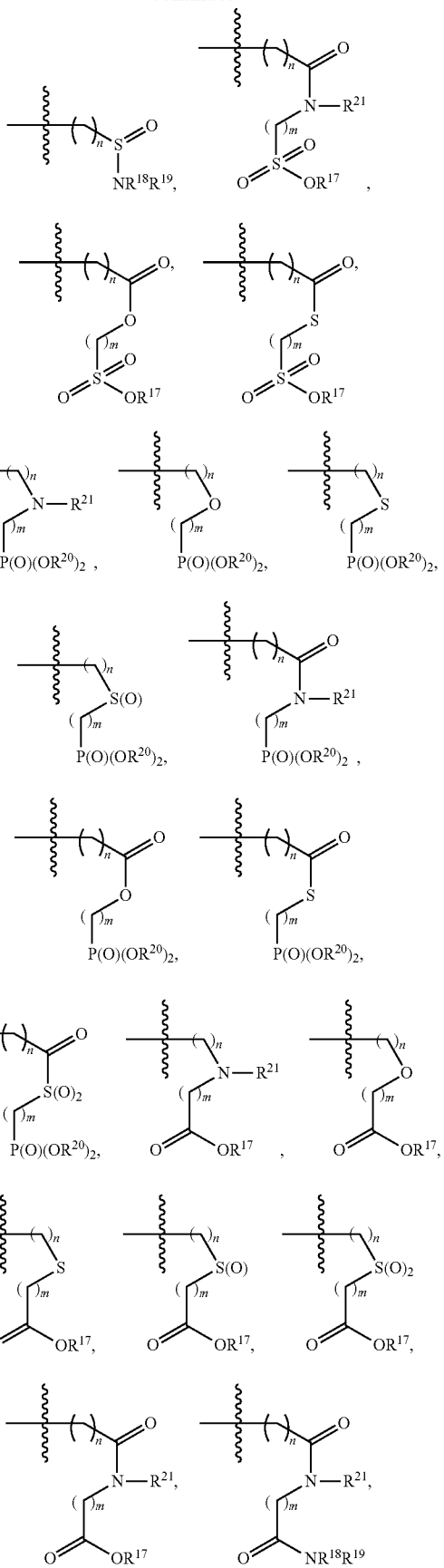

-continued

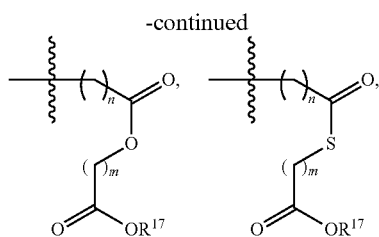

optionally substituted $C_{3-8}$ cycloalkyl, optionally substituted $C_{3-8}$ cycloalkenyl, optionally substituted $C_{6-10}$ aryl, optionally substituted heterocycle, or together with $R^5$ forms a spiro monocyclic or polycyclic, carbocyclic or heterocyclic, saturated or unsaturated 5- to 10-membered ring which is optionally substituted;

$R^5$ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, optionally substituted heterocycle, or together with $R^4$ forms a spiro monocyclic or polycyclic carbocyclic or heterocyclic, saturated or unsaturated 5- to 10-membered ring which is optionally substituted or together with $R^3$ forms a 5- or 6-membered ring which is optionally substituted;

$R^6$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;

$R^7$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{16}$;

$R^8$ is halogen, hydrogen, optionally substituted $C_{1-8}$ alkyl, $OR^9$, $C(O)R^{10}$, $NO_2$, $NR^{13}R^{14}$, CN, $SR^{15}$ or $SO_2R^{18}$;

$R^9$ is hydrogen, $C(O)(C_{1-8}$ alkyl) or optionally substituted $C_{1-8}$ alkyl;

$R^{10}$ is hydrogen, optionally substituted $C_{1-8}$ alkyl, $O(C_{1-8}$ alkyl), $NR^{11}R^{12}$ or OH;

$R^{11}$ is hydrogen, optionally substituted $C_{6-10}$ aryl or optionally substituted $C_{1-8}$ alkyl;

$R^{12}$ is hydrogen, optionally substituted $C_{6-10}$ aryl or optionally substituted $C_{1-8}$ alkyl;

$R^{13}$ is hydrogen, optionally substituted $C_{6-10}$ aryl or optionally substituted $C_{1-8}$ alkyl;

$R^{14}$ is hydrogen, optionally substituted $C_{6-10}$ aryl, optionally substituted $C_{1-8}$ alkyl, $C(O)(C_{1-8}$ alkyl) or $SO_2(C_{1-8}$ alkyl);

$R^{15}$ is hydrogen, optionally substituted $C_{1-8}$ alkyl or $O(C_{1-8}$ alkyl);

$R^{16}$ is OH, $O(C_{1-8}$ alkyl), $(C_{1-8}$ alkyl) or $NR^{11}R^{12}$;

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl, or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5;

m is 1, 2, 3, 4, or 5; and with the proviso that the compound of Formula I is not of structures:

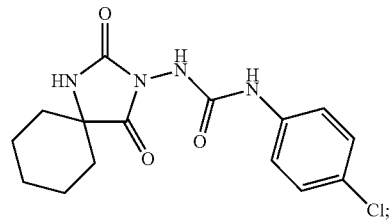

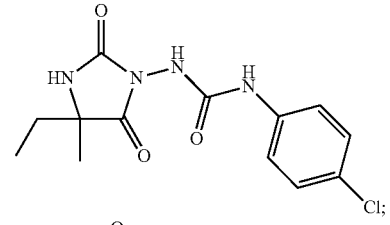

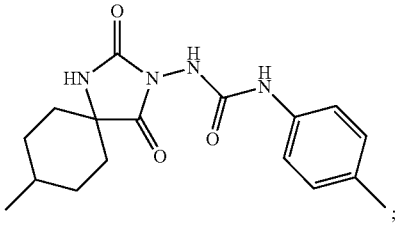

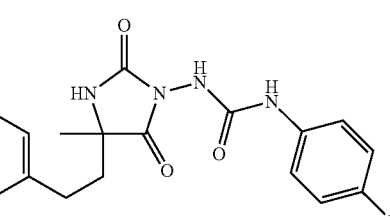

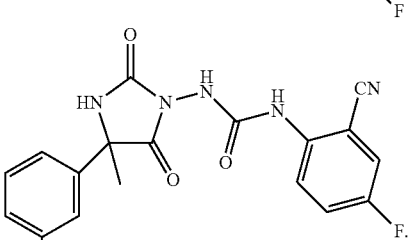

2. A compound according to claim 1, wherein:

$R^1$ is halogen, hydrogen or optionally substituted $C_{1-8}$ alkyl;

$R^2$ is halogen, optionally substituted $C_{1-8}$ alkyl, $CF_3$, $SR^{15}$, $OR^9$ or CN;

$R^3$ is hydrogen, optionally substituted $C_{1-8}$ alkyl, optionally substituted $C_{3-8}$ cycloalkyl or optionally substituted $C_{3-8}$ cycloalkenyl;

$R^4$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^5$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;

$R^6$ is halogen, hydrogen or optionally substituted $C_{1-8}$ alkyl;

$R^7$ is halogen, hydrogen or optionally substituted $C_{1-8}$ alkyl;

$R^8$ is halogen, hydrogen or optionally substituted $C_{1-8}$ alkyl;

$R^9$ is hydrogen, $C(O)(C_{1-8}$ alkyl) or optionally substituted $C_{1-8}$ alkyl; and
$R^{15}$ is hydrogen, optionally substituted $C_{1-8}$ alkyl or $O(C_{1-8}$ alkyl).

3. A compound according to claim 1, wherein:
$R^1$ is halogen, hydrogen or optionally substituted $C_{1-8}$ alkyl;
$R^2$ is halogen, optionally substituted $C_{1-8}$ alkyl, $CF_3$, $SR^{15}$, $OR^9$ or CN;
$R^3$ is hydrogen, optionally substituted $C_{1-8}$ alkyl, optionally substituted $C_{3-8}$ cycloalkyl
or optionally substituted $C_{3-8}$ cycloalkenyl;
$R^4$ is optionally substituted $C_{1-8}$ alkyl, optionally substituted $C_{6-10}$ aryl

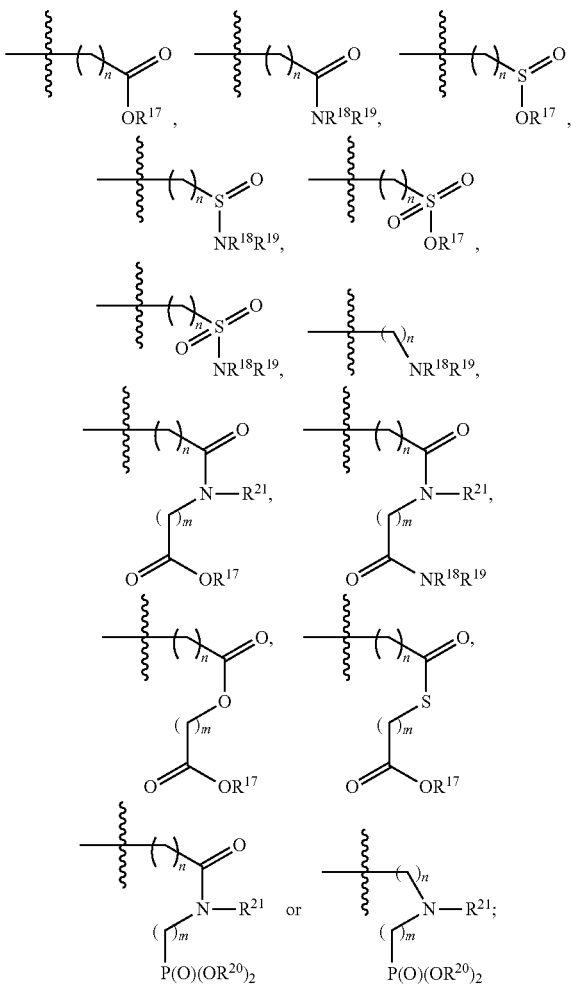

$R^5$ is optionally substituted $C_{1-8}$ alkyl or optionally substituted $C_{3-8}$ cycloalkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl);
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl), optionally substituted $C_{6-10}$ aryl or optionally substituted $C_{1-8}$ alkyl;
$R^{19}$ is hydrogen, $C(O)(C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5; and
m is 1, 2, 3, 4, or 5.

4. A compound according to claim 1, wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen;
$R^4$ is optionally substituted $C_{1-8}$ alkyl, optionally substituted $C_{6-10}$ aryl,

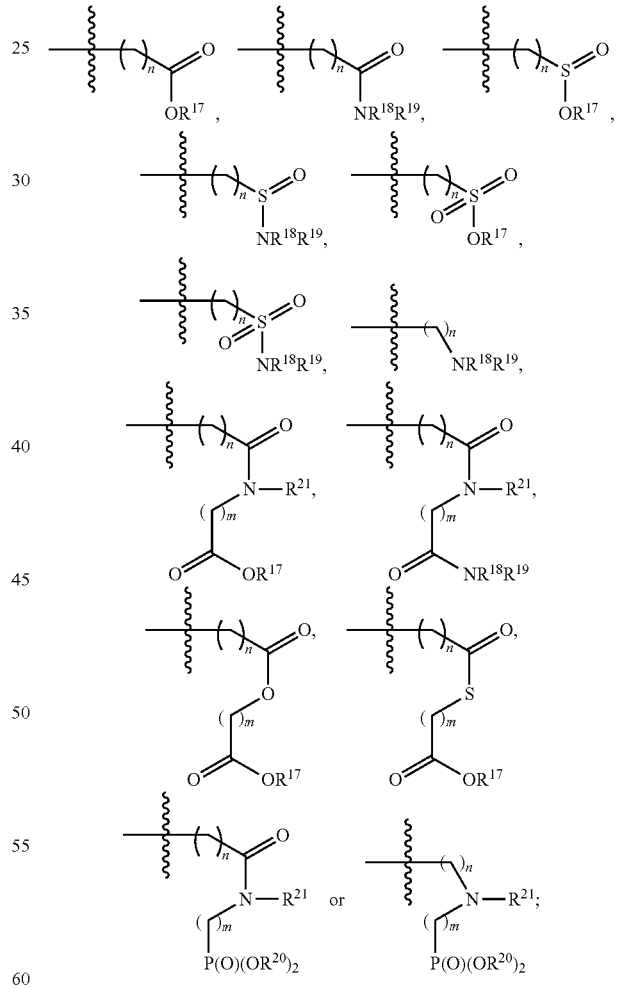

$R^5$ is optionally substituted $C_{1-8}$ alkyl or optionally substituted $C_{3-8}$ cycloalkyl;
$R^6$ is halogen, hydrogen or optionally substituted $C_{1-8}$ alkyl;
$R^7$ is halogen, hydrogen or optionally substituted $C_{1-8}$ alkyl;

$R^8$ is halogen, hydrogen or optionally substituted $C_{1-8}$ alkyl;

$R^9$ is hydrogen, $C(O)(C_{1-8}$ alkyl) or optionally substituted $C_{1-8}$ alkyl;

$R^{15}$ is hydrogen, optionally substituted $C_{1-8}$ alkyl or $O(C_{1-8}$ alkyl);

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5; and m is 1, 2, 3, 4, or 5.

5. A compound according to claim 1, wherein:

$R^1$ is halogen, hydrogen or optionally substituted $C_{1-8}$ alkyl;

$R^2$ is halogen, optionally substituted $C_{1-8}$ alkyl, $CF_3$, $SR^{15}$, $OR^9$ or CN;

$R^3$ is hydrogen, optionally substituted $C_{1-8}$ alkyl, optionally substituted $C_{3-8}$ cycloalkyl or optionally substituted $C_{3-8}$ cycloalkenyl;

$R^4$ is optionally substituted $C_{1-8}$ alkyl,

[structures with $OR^{17}$, $NR^{18}R^{19}$, $OR^{17}$, $NR^{18}R^{19}$, $OR^{17}$, $NR^{18}R^{19}$, $NR^{18}R^{19}$, groups containing $N-R^{21}$, $OR^{17}$, $NR^{18}R^{19}$, and cyclic $O$ and $S$ containing structures with $OR^{17}$]

-continued

[structures with $N-R^{21}$, $P(O)(OR^{20})_2$]

$R^5$ is optionally substituted $C_{1-8}$ alkyl;

$R^6$ is halogen, hydrogen or optionally substituted $C_{1-8}$ alkyl;

$R^7$ is halogen, hydrogen or optionally substituted $C_{1-8}$ alkyl;

$R^8$ is halogen, hydrogen or optionally substituted $C_{1-8}$ alkyl;

$R^9$ is hydrogen, $C(O)(C_{1-8}$ alkyl) or optionally substituted $C_{1-8}$ alkyl;

$R^{15}$ is hydrogen, optionally substituted $C_{1-8}$ alkyl or $O(C_{1-8}$ alkyl);

$R^{17}$ is hydrogen, optionally substituted $C_{6-10}$ aryl or optionally substituted $C_{1-8}$ alkyl;

$R^{18}$ is hydrogen, $C(O)(C_{1-8}$ alkyl), optionally substituted $C_{6-10}$ aryl or optionally substituted $C_{1-8}$ alkyl;

$R^{19}$ is hydrogen, $C(O)(C_{1-8}$ alkyl), optionally substituted $C_{6-10}$ aryl or optionally substituted $C_{1-8}$ alkyl;

$R^{20}$ is hydrogen, optionally substituted $C_{6-10}$ aryl or optionally substituted $C_{1-8}$ alkyl;

$R^{21}$ is hydrogen, optionally substituted $C_{6-10}$ aryl or optionally substituted $C_{1-8}$ alkyl;

n is 1, 2, 3, 4, or 5; and m is 1, 2, 3, 4, or 5.

6. A compound according to claim 1, wherein:

$R^1$ is halogen, hydrogen or optionally substituted $C_{1-8}$ alkyl;

$R^2$ is halogen, optionally substituted $C_{1-8}$ alkyl, $CF_3$, $SR^{15}$, $OR^9$ or CN;

$R^3$ is hydrogen;

$R^4$ is

[structures with $OR^{17}$, $NR^{18}R^{19}$, $OR^{17}$, $NR^{18}R^{19}$, $OR^{17}$, $NR^{18}R^{19}$, $NR^{18}R^{19}$, and groups with $N-R^{21}$ containing $OR^{17}$ and $NR^{18}R^{19}$]

-continued

[chemical structures with substituents including $OR^{17}$, $NR^{18}R^{19}$, $P(O)(OR^{20})_2$, $R^{21}$]

$R^5$ is optionally substituted $C_{1-8}$ alkyl;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl;
$R^{15}$ is hydrogen, optionally substituted $C_{1-8}$ alkyl or $O(C_{1-8}$ alkyl);
$R^{17}$ is hydrogen, optionally substituted $C_{6-10}$ aryl or optionally substituted $C_{1-8}$ alkyl;
$R^{18}$ is hydrogen, $C(O)(C_{1-8}$ alkyl), optionally substituted $C_{6-10}$ aryl or optionally substituted $C_{1-8}$ alkyl;
$R^{19}$ is hydrogen, $C(O)(C_{1-8}$ alkyl), optionally substituted $C_{6-10}$ aryl or optionally substituted $C_{1-8}$ alkyl;
$R^{20}$ is hydrogen, optionally substituted $C_{6-10}$ aryl or optionally substituted $C_{1-8}$ alkyl;
$R^{21}$ is hydrogen, optionally substituted $C_{6-10}$ aryl or optionally substituted $C_{1-8}$ alkyl;
n is 1, 2, 3, 4, or 5; and
m is 1, 2, 3, 4, or 5.

7. A compound according to claim 1, wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen, optionally substituted $C_{1-8}$ alkyl, optionally substituted $C_{3-8}$ cycloalkyl or optionally substituted $C_{3-8}$ cycloalkenyl;
$R^4$ is optionally substituted $C_{1-8}$ alkyl;
$R^5$ is optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
$R^6$ is halogen, hydrogen or optionally substituted $C_{1-8}$ alkyl;
$R^7$ is halogen, hydrogen or optionally substituted $C_{1-8}$ alkyl;
$R^8$ is halogen, hydrogen or optionally substituted $C_{1-8}$ alkyl;
$R^9$ is hydrogen, $C(O)(C_{1-8}$ alkyl) or optionally substituted $C_{1-8}$ alkyl; and
$R^{15}$ is hydrogen, optionally substituted $C_{1-8}$ alkyl or $O(C_{1-8}$ alkyl).

8. A compound according to claim 1, wherein:
$R^1$ is halogen, hydrogen or optionally substituted $C_{1-8}$ alkyl;
$R^2$ is halogen, optionally substituted $C_{1-8}$ alkyl, $SR^{15}$, $CF_3$, $OR^9$ or CN;
$R^3$ is hydrogen;

$R^4$ is [chemical structures with substituents including $NR^{18}R^{19}$, $OR^{17}$, $R^{21}$, $P(O)(OR^{20})_2$]

-continued

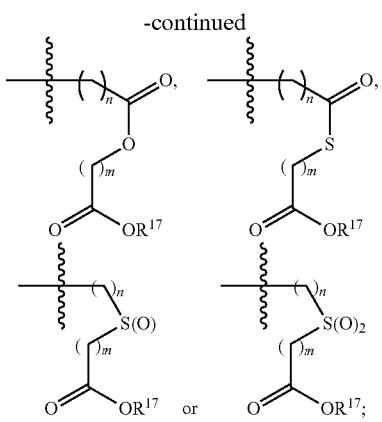

R⁵ is optionally substituted $C_{1-8}$ alkyl;
R⁶ is halogen, hydrogen or optionally substituted $C_{1-8}$ alkyl;
R⁷ is halogen, hydrogen or optionally substituted $C_{1-8}$ alkyl;
R⁸ is halogen, hydrogen or optionally substituted $C_{1-8}$ alkyl;
R⁹ is hydrogen, C(O)($C_{1-8}$ alkyl) or optionally substituted $C_{1-8}$ alkyl;
R¹⁵ is hydrogen, optionally substituted $C_{1-8}$ alkyl or O($C_{1-8}$ alkyl);
R¹⁷ is hydrogen, optionally substituted $C_{6-10}$ aryl or optionally substituted $C_{1-8}$ alkyl;
R¹⁸ is hydrogen, C(O)($C_{1-8}$ alkyl), optionally substituted $C_{6-10}$ aryl or optionally substituted $C_{1-8}$ alkyl;
R¹⁹ is hydrogen, C(O)($C_{1-8}$ alkyl), optionally substituted $C_{6-10}$ aryl or optionally substituted $C_{1-8}$ alkyl;
R²⁰ is hydrogen, optionally substituted $C_{6-10}$ aryl or optionally substituted $C_{1-8}$ alkyl;
R²¹ is hydrogen, optionally substituted $C_{6-10}$ aryl or optionally substituted $C_{1-8}$ alkyl;
n is 1 or 2; and
m is 1 or 2.

9. A compound according to claim 1, wherein:
R¹ is halogen, hydrogen or optionally substituted $C_{1-8}$ alkyl;
R² is halogen, optionally substituted $C_{1-8}$ alkyl, SR¹⁵, CF₃, OR⁹ or CN;
R³ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl or optionally substituted heterocycle;
R⁴ together with R⁵ forms a spiro monocyclic or polycyclic, carbocyclic or heterocyclic, saturated or unsaturated 5- to 10 membered ring which is optionally substituted;
R⁵ together with R⁴ forms a spiro monocyclic or polycyclic carbocyclic or heterocyclic, saturated or unsaturated 5- to 10 membered ring which is optionally substituted;
R⁶ is halogen, hydrogen, or optionally substituted $C_{1-8}$ alkyl;
R⁷ is halogen, hydrogen, or optionally substituted $C_{1-8}$ alkyl;
R⁸ is halogen, hydrogen, or optionally substituted $C_{1-8}$ alkyl;
R⁹ is hydrogen or optionally substituted $C_{1-8}$ alkyl; and
R¹⁵ is hydrogen, optionally substituted $C_{1-8}$ alkyl or O($C_{1-8}$ alkyl).

10. A compound according to claim 1, wherein:
R¹ is halogen, hydrogen, or optionally substituted $C_{1-8}$ alkyl;
R² is halogen, optionally substituted $C_{1-8}$ alkyl, SR¹⁵, CF₃, OR⁹ or CN;
R³ together with R⁵ forms a 5- or 6 membered ring which is optionally substituted;
R⁴ is hydrogen, optionally substituted $C_{1-8}$ alkyl, optionally substituted $C_{3-8}$ cycloalkyl, optionally substituted $C_{3-8}$ cycloalkenyl, optionally substituted $C_{6-10}$ aryl, or optionally substituted heterocycle,
R⁵ together with R³ forms a 5- or 6 membered ring which is optionally substituted;
R⁶ is halogen, hydrogen, or optionally substituted $C_{1-8}$ alkyl;
R⁷ is halogen, hydrogen, or optionally substituted $C_{1-8}$ alkyl;
R⁸ is halogen, hydrogen, or optionally substituted $C_{1-8}$ alkyl;
R⁹ is hydrogen or optionally substituted $C_{1-8}$ alkyl; and
R¹⁵ is hydrogen, optionally substituted $C_{1-8}$ alkyl or O($C_{1-8}$ alkyl).

11. A compound according to claim 1, wherein:
R¹ is halogen or hydrogen;
R² is halogen, optionally substituted $C_{1-8}$ alkyl, SR¹⁵, CF₃, OR⁹ or CN;
R³ is hydrogen;
R⁴ is optionally substituted $C_{1-8}$ alkyl;
R⁵ is optionally substituted $C_{1-8}$ alkyl;
R⁶ is halogen or hydrogen;
R⁷ is hydrogen;
R⁸ is hydrogen;
R⁹ is optionally substituted $C_{1-8}$ alkyl; and
R¹⁵ is hydrogen, optionally substituted $C_{1-8}$ alkyl or O($C_{1-8}$ alkyl).

12. A compound according to claim 1 selected from:
1-(4-Bromophenyl)-3-(4,4-diethyl-2,5-dioxoimidazolidin-1-yl)urea;
1-(4-Chlorophenyl)-3-(4,4-diethyl-2,5-dioxoimidazolidin-1-yl)urea;
1-(4-Methoxyphenyl)-3-(4,4-diethyl-2,5-dioxoimidazolidin-1-yl)urea;
1-(4-Ethylphenyl)-3-(4,4-diethyl-2,5-dioxoimidazolidin-1-yl)urea;
1-(4-Cyanophenyl)-3-(4,4-diethyl-2,5-dioxoimidazolidin-1-yl)urea;
1-(4-Bromo-2-fluorophenyl)-3-(4,4-diethyl-2,5-dioxoimidazolidin-1-yl)urea;
1-(4-Methylphenyl)-3-(4,4-diethyl-2,5-dioxoimidazolidin-1-yl)urea;
1-(4-Methylthiophenyl)-3-(4,4-diethyl-2,5-dioxoimidazolidin-1-yl)urea;
1-(4-Bromophenyl)-3-(4-methyl-2,5-dioxo-4-phenethylimidazolidin-1-yl)urea;
1-(4-Bromophenyl)-3-(2,4-dioxo-1,3-diazaspiro[4.4]nonan-3-yl)urea;
1-(4-Bromo-2-fluorophenyl)-3-(2,4-dioxo-1,3-diazaspiro[4.4]nonan-3-yl)urea;
1-(4-Bromophenyl)-3-(4,4-dimethyl-2,5-dioxoimidazolidin-1-yl)urea;
1-(4-Bromophenyl)-3-(2,5-dioxo-1',3'-dihydrospiro[imidazolidine-4,2'-inden]-1-yl)urea
1-(4-Bromophenyl)-3-(2,4-dioxo-1,3-diazaspiro[4.5]decan-3-yl)urea;
1-(4-Bromo-2-fluorophenyl)-3-(2,4-dioxo-1,3-diazaspiro[4.5]decan-3-yl)urea;

1-(4-Chloro-2-fluorophenyl)-3-(4,4-diethyl-2,5-dioxoimidazolidin-1-yl)urea;
1-(4-Bromo-2-fluorophenyl)-3-(4-methyl-2,5-dioxo-4-phenethylimidazolidin-1-yl)urea;
1-(4-Bromophenyl)-3-(4-ethyl-4-isopropyl-2,5-dioxoimidazolidin-1-yl)urea;
1-(4-Chloro-3-fluorophenyl)-3-(4,4-diethyl-2,5-dioxoimidazolidin-1-yl)urea;
1-(4-Bromo-2-fluorophenyl)-3-(4-ethyl-4-isopropyl-2,5-dioxoimidazolidin-1-yl)urea;
1-(2,4-Dioxo-1,3-diazaspiro[4,5]decan-3-yl)-3-(4-methoxypheynyl)urea;
1-(4-Bromo-2-fluorophenyl)-3-(2,5-dioxo-1',3'-dihydrospiro[imidazolidine-4,2'-inden]-1-yl)urea;
1-(4-Bromophenyl)-3-(4-methyl-2,5-dioxo-4-(phenoxymethyl)imidazolidin-1-yl)urea;
1-(4-Bromo-2-fluorophenyl)-3-(2,5-dioxo-3',4'-dihydro-1'H-spiro[imidazolidine-4,2'-napthlalen-1-yl)urea
1-(4-Bromophenyl)-3-(2,5-dioxo-3',4'-dihydro-1'H-spiro[imidazolidine-4,2'-napthlalen-1-yl)urea
1-(4-Bromo-2-fluorophenyl)-3-(4-methyl-2,5-dioxo-4-(phenoxymethyl)imidazolidin-1-yl)urea;
1-(4-Bromo-2-fluorophenyl)-3-(4-ethyl-2,5-dioxo-4-(phenethyl)imidazolidin-1-yl)urea;
1-(4-Bromophenyl)-3-(4-ethyl-2,5-dioxo-4-(phenethyl)imidazolidin-1-yl)urea;
1-(4-Bromophenyl)-3-(4-isobutyl-2,5-dioxo-4-phenethyl)imidazolidin-1-yl)urea;
1-(4-Bromo-2-fluorophenyl)-3-(4-isobutyl-2,5-dioxo-4-phenethyl)imidazolidin-1-yl)urea;
1-(4-Bromophenyl)-3-(4-(4-chlorophenethyl)-4-methyl-2,5-dioxoimidazolidin-1-yl)urea;
1-(4-Bromo-2-fluorophenyl)-3-(4-chlorophenethyl)-4-methyl-2,5-dioxo-imidazolidin-1-yl)urea;
1-(4-Bromophenyl)-3-(4-(2-furan-2-yl)ethyl)-4-methyl-2,5-dioxoimidazolidin-1-yl)urea;
1-(4-Bromo-2-fluorophenyl)-3-(4-(2-furan-2-yl)ethyl)-4-methyl-2,5-dioxoimidazolidin-1-yl)urea;
1-(4-Bromophenyl)-3-(4-(2-fluorophenethyl)-4-methyl-2,5-dioxoimidazolidin-1-yl)urea;
1-(4-Bromo-2-fluorophenyl)-3-(4-(2-fluorophenethyl)-4-methyl-2,5-dioxoimidazolidin-1-yl)urea;
1-(4-Bromophenyl)-3-(4-(4-fluorophenethyl)-4-methyl-2,5-dioxoimidazolidin-1-yl)urea;
1-(4-Bromo-2-fluorophenyl)-3-(4-(4-fluorophenethyl)-4-methyl-2,5-dioxoimidazolidin-1-yl)urea;
1-(4-Bromophenyl)-3-(4-(3-fluorophenethyl)-4-methyl-2,5-dioxoimidazolidin-1-yl)urea;
1-(4-Bromophenyl)-3-(4-(4-hydroxyphenethyl)-4-methyl-2,5-dioxoimidazolidin-1-yl)urea;
1-(4-Bromophenyl)-3-(4-methyl-2,5-dioxo-4-(2-thiophen-2-yl)ethyl)imidazolidin-1-yl)urea;
1-(4-Bromo-2-fluorophenyl)-3-(4-methyl-2,5-dioxo-4-(2-thiophen-2-yl)ethyl)imidazolidin-1-yl)urea;
1-(4-Bromo-2-fluorophenyl)-3-(4-(4-hydroxyphenethyl)-4-methyl-2,5-dioxoimidazolidin-1-yl)urea;
1-(4-Bromophenyl)-3-(4-methyl-4-(2-(5-methylfuran-2-yl)ethyl)2,5-dioxoimidazolidin-1-yl)urea;
1-(4-Bromophenyl)-3-(4-(3-fluoro-4-hydroxyphenethyl)-4-methyl-2,5-dioxoimidazolidin-1-yl)urea;
1-(4-Bromo-2-fluorophenyl)-3-(4-(3-fluoro-4-hydroxyphenethyl)-4-methyl-2,5-dioxoimidazolidin-1-yl)urea
1-(4-Bromophenyl)-3-(4-isopropyl-4-(2-((4-methoxybenzyl)oxy)ethyl)-2,5-dioxoimidazolidin-1-yl)urea;
1-(4-Bromophenyl)-3-(4-(2-hydroxyphenethyl)-4-methyl-2,5-dioxoimidazolidin-1-yl)urea;
1-(4-Bromo-2-fluorophenyl)-3-(4-(2-hydroxyphenethyl)-4-methyl-2,5-dioxoimidazolidin-1-yl)urea;
1-(4-Bromophenyl)-3-(4-(3-hydroxyphenethyl)-4-methyl-2,5-dioxoimidazolidin-1-yl)urea;
1-(4-Bromo-2-fluorophenyl)-3-(4-(3-hydroxyphenethyl)-4-methyl-2,5-dioxoimidazolidin-1-yl)urea;
1-(4-Bromophenyl)-3-(4-methyl-2,5-dioxo-4-(2-(pyridin-4-yl)ethyl)imidazolidin-1-yl)urea;
1-(4-Bromo-2-fluorophenyl)-3-(4-methyl-2,5-dioxo-4-(pyridin-4-yl)ethyl)imidazolidin-1-yl)urea;
1-(4-Bromophenyl)-3-(4-isopropyl-4-(((4-methoxybenzyl)oxy)methyl)-2,5-dioxoimidazolidin-1-yl)urea;
1-(4-Bromo-2-fluorophenyl)-3-(4-isopropyl-4-(((4-methoxybenzyl)oxy)methyl)-2,5-dioxoimidazolidin-1-yl)urea;
Methyl 4-(2-(1-(3-(4-Bromophenyl)ureido)-4-methyl-2,5-dioxoimidazolidin-4-yl)ethyl)benzoate;
Methyl 2-(2-(1-(3-(4-bromophenyl)ureido)-4-methyl-2,5-dioxoimidazolidin-4-yl)ethyl)benzoate;
Methyl 2-(2-(1-(3-(4-bromophenyl)ureido)-4-ethyl-2,5-dioxoimidazolidin-4-yl)ethyl)benzoate;
Methyl 2-(2-(1-(3-(4-bromo-2-fluorophenyl)ureido)-4-ethyl-2,5-dioxoimidazolidin-4-yl)ethyl)benzoate;
Ethyl 2-(1-(3-(4-bromo-2-fluorophenyl)ureido)-4-isopropyl-2,5-dioxoimidazolidin-4-yl)acetate;
Ethyl 2-(1-(3-(4-bromophenyl)ureido)-4-isopropyl-2,5-dioxoimidazolidin-4-yl)acetate;
1-(4-Bromophenyl)-3-[4-(1H-indol-3-ylmethyl)-4-methyl-2,5-dioxoimidazolidin-1-yl]urea;
1-(4-Bromo-2-fluorophenyl)-3-[4-(5-ethyl-1H-indol-2-yl)-4-methyl-2,5-dioxoimidazolidin-1-yl]urea;
1-(4-Bromophenyl)-3-(4,4-dicyclopropyl-2,5-dioxoimidazolidin-1-yl)urea;
1-(4-Bromophenyl)-3-[2,5-dioxo-4,4-di(propan-2-yl)imidazolidin-1-yl]urea;
Ethyl-3-[1-{[(4-bromophenyl)carbamoyl]amino}-2,5-dioxo-4-(propan-2-yl)imidazolidin-4-yl]propanoate;
1-(4-Bromophenyl)-3-(4,4-dimethyl-2,5-dioxo-3-phenylimidazolidin-1-yl)urea;
(−)-1-(4-Bromophenyl)-3-(4-methyl-2,5-dioxo-4-phenethylimidazolidin-1-yl)urea;
(+)-1-(4-Bromophenyl)-3-(4-methyl-2,5-dioxo-4-phenethylimidazolidin-1-yl)urea;
(+)-1-(4-Bromophenyl)-3-(4-ethyl-4-isopropyl-2,5-dioxoimidazolidin-1-yl)urea;
(−)-1-(4-Bromophenyl)-3-(4-ethyl-4-isopropyl-2,5-dioxoimidazolidin-1-yl)urea;
1-(4-Bromophenyl)-3-(4-(hydroxymethyl)-4-isopropyl-2,5-dioxoimidazolidin-1-yl)urea;
1-(4-Bromophenyl)-3-(4-(2-hydroxyethyl)-4-isopropyl-2,5-dioxoimidazolidin-1-yl)urea;
1-(4-Bromo-2-fluorophenyl)-3-(4-(2-hydroxymethyl)-4-isopropyl-2,5-dioxoimidazolidin-1-yl)urea;
4-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-ethyl-2,5-dioxoimidazolidin-4-yl)ethyl)benzoic acid;
Methyl 2-(2-(1-(3-(4-bromo-2-fluorophenyl)ureido)-4-ethyl-2,5-dioxoimidazolidin-4-yl)ethyl)benzoate;
2-(1-(3-(4-Bromophenyl)ureido)-4-isopropyl-2,5-dioxoimidazolidin-4-yl)acetic acid;
2-(1-(3-(4-Bromo-2-fluorophenyl)ureido)-4-isopropyl-2,5-dioxoimidazolidin-4-yl)acetic acid;
3-[1-{[(4-bromophenyl)carbamoyl]amino}-2,5-dioxo-4-(propan-2-yl)imidazolidin-4-yl]propanoic acid;

2-(1-(3-(4-Bromophenyl)ureido)-4-isopropyl-2,5-dioxoimidazolidin-4-yl)-N-(2-hydroxyethyl)acetamide;
tert-Butyl 2-(2-(1-(3-(4-bromophenyl)ureido)-4-isopropyl-2,5-dioxoimidazolidin-4-yl)acetamido)acetate;
Diethyl((2-(1-(3-(4-bromophenyl)ureido)-4-isopropyl-2,5-dioxoimidazolidin-4-yl)acetamido)methyl)phosphonate;
2-(1-(3-(4-Bromophenyl)ureido)-4-isopropyl-2,5-dioxoimidazolidin-4-yl)-N,N-bis(2-hydroxyethyl)acetamide;
Diisopropyl((2-(1-(3-(4-bromophenyl)ureido)-4-isopropyl-2,5-dioxoimidazolidin-4-yl)acetamido)methyl) phosphonate;
Ethyl hydrogen((2-(1-(3-(4-bromophenyl)ureido)-4-isopropyl-2,5-dioxoimidazolidin-4-yl)acetamido)methyl) phosphonate;
tert-Butyl 2-(2-(1-(3-(4-bromophenyl)ureido)-4-isopropyl-2,5-dioxoimidazolidin-4-yl)acetamido)-2-methylpropanoate;
tert-Butyl 3-(2-(1-(3-(4-bromophenyl)ureido)-4-isopropyl-2,5-dioxoimidazolidin-4-yl)acetamido)propanoate;
2-(2-(1-(3-(4-Bromophenyl)ureido)-4-isopropyl-2,5-dioxoimidazolidin-4-yl)acetamido)acetic acid;
3-(2-(1-(3-(4-Bromophenyl)ureido)-4-isopropyl-2,5-dioxoimidazolidin-4-yl)acetamido)propanoic acid;
2-(1-(3-(4-Bromo-2-fluorophenyl)ureido)-4-isopropyl-2,5-dioxoimidazolidin-4-yl)-N-(2-hydroxyethyl)acetamide;
2-(2-(1-(3-(4-Bromophenyl)ureido)-4-isopropyl-2,5-dioxoimidazolidin-4-yl)acetamido)-2-methylpropanoic acid; and
N-(2-Amino-2-oxoethyl)-2-(1-(3-(4-bromophenyl)ureido)-4-isopropyl-2,5-dioxoimidazolidin-4-yl)acetamide.

13. A pharmaceutical composition comprising as active ingredient a therapeutically effective amount of a compound according to claim 1 and a pharmaceutically acceptable adjuvant, diluent or carrier.

14. A pharmaceutical composition according to claim 13 wherein the compound is selected from:
1-(4-Bromophenyl)-3-(4,4-diethyl-2,5-dioxoimidazolidin-1-yl)urea;
1-(4-Chlorophenyl)-3-(4,4-diethyl-2,5-dioxoimidazolidin-1-yl)urea;
1-(4-Methoxyphenyl)-3-(4,4-diethyl-2,5-dioxoimidazolidin-1-yl)urea;
1-(4-Ethylphenyl)-3-(4,4-diethyl-2,5-dioxoimidazolidin-1-yl)urea;
1-(4-Cyanophenyl)-3-(4,4-diethyl-2,5-dioxoimidazolidin-1-yl)urea;
1-(4-Bromo-2-fluorophenyl)-3-(4,4-diethyl-2,5-dioxoimidazolidin-1-yl)urea;
1-(4-Methylphenyl)-3-(4,4-diethyl-2,5-dioxoimidazolidin-1-yl)urea;
1-(4-Methylthiophenyl)-3-(4,4-diethyl-2,5-dioxoimidazolidin-1-yl)urea;
1-(4-Bromophenyl)-3-(4-methyl-2,5-dioxo-4-phenethylimidazolidin-1-yl)urea;
1-(4-Bromophenyl)-3-(2,4-dioxo-1,3-diazaspiro[4.4]nonan-3-yl)urea;
1-(4-Bromo-2-fluorophenyl)-3-(2,4-dioxo-1,3-diazaspiro[4.4]nonan-3-yl)urea;
1-(4-Bromophenyl)-3-(4,4-dimethyl-2,5-dioxoimidazolidin-1-yl)urea;
1-(4-Bromophenyl)-3-(2,5-dioxo-1',3'-dihydrospiro[imidazolidine-4,2'-inden]-1-yl)urea;
1-(4-Bromophenyl)-3-(2,4-dioxo-1,3-diazaspiro[4.5]decan-3-yl)urea;
1-(4-Bromo-2-fluorophenyl)-3-(2,4-dioxo-1,3-diazaspiro[4.5]decan-3-yl)urea;
1-(4-Chloro-2-fluorophenyl)-3-(4,4-diethyl-2,5-dioxoimidazolidin-1-yl)urea;
1-(4-Bromo-2-fluorophenyl)-3-(4-methyl-2,5-dioxo-4-phenethylimidazolidin-1-yl)urea;
1-(4-Bromophenyl)-3-(4-ethyl-4-isopropyl-2,5-dioxoimidazolidin-1-yl)urea;
1-(4-Chloro-3-fluorophenyl)-3-(4,4-diethyl-2,5-dioxoimidazolidin-1-yl)urea;
1-(4-Bromo-2-fluorophenyl)-3-(4-ethyl-4-isopropyl-2,5-dioxoimidazolidin-1-yl)urea;
1-(2,4-Dioxo-1,3-diazaspiro[4,5]decan-3-yl)-3-(4-methoxypheynyl)urea;
1-(4-Bromo-2-fluorophenyl)-3-(2,5-dioxo-1',3'-dihydrospiro[imidazolidine-4,2'-inden]-1-yl)urea;
1-(4-Bromophenyl)-3-(4-methyl-2,5-dioxo-4-(phenoxymethyl)imidazolidin-1-yl)urea;
1-(4-Bromo-2-fluorophenyl)-3-(2,5-dioxo-3',4'-dihydro-1'H-spiro[imidazolidine-4,2'-napthlalen-1-yl)urea;
1-(4-Bromophenyl)-3-(2,5-dioxo-3',4'-dihydro-1'H-spiro[imidazolidine-4,2'-napthlalen-1-yl)urea
1-(4-Bromo-2-fluorophenyl)-3-(4-methyl-2,5-dioxo-4-(phenoxymethyl)imidazolidin-1-yl)urea;
1-(4-Bromo-2-fluorophenyl)-3-(4-ethyl-2,5-dioxo-4-(phenethyl)imidazolidin-1-yl)urea;
1-(4-Bromophenyl)-3-(4-ethyl-2,5-dioxo-4-(phenethyl)imidazolidin-1-yl)urea;
1-(4-Bromophenyl)-3-(4-isobutyl-2,5-dioxo-4-phenethyl)imidazolidin-1-yl)urea;
1-(4-Bromo-2-fluorophenyl)-3-(4-isobutyl-2,5-dioxo-4-phenethyl)imidazolidin-1-yl)urea;
1-(4-Bromophenyl)-3-(4-(4-chlorophenethyl)-4-methyl-2,5-dioxoimidazolidin-1-yl)urea;
1-(4-Bromo-2-fluorophenyl)-3-(4-chlorophenethyl)-4-methyl-2,5-dioxo-imidazolidin-1-yl)urea;
1-(4-Bromophenyl)-3-(4-(2-furan-2-yl)ethyl)-4-methyl-2,5-dioxoimidazolidin-1-yl)urea;
1-(4-Bromo-2-fluorophenyl)-3-(4-(2-furan-2-yl)ethyl)-4-methyl-2,5-dioxoimidazolidin-1-yl)urea;
1-(4-Bromophenyl)-3-(4-(2-fluorophenethyl)-4-methyl-2,5-dioxoimidazolidin-1-yl)urea;
1-(4-Bromo-2-fluorophenyl)-3-(4-(2-fluorophenethyl)-4-methyl-2,5-dioxoimidazolidin-1-yl)urea;
1-(4-Bromophenyl)-3-(4-(4-fluorophenethyl)-4-methyl-2,5-dioxoimidazolidin-1-yl)urea;
1-(4-Bromo-2-fluorophenyl)-3-(4-(4-fluorophenethyl)-4-methyl-2,5-dioxoimidazolidin-1-yl)urea;
1-(4-Bromophenyl)-3-(4-(3-fluorophenethyl)-4-methyl-2,5-dioxoimidazolidin-1-yl)urea;
1-(4-Bromophenyl)-3-(4-(4-hydroxyphenethyl)-4-methyl-2,5-dioxoimidazolidin-1-yl)urea;
1-(4-Bromophenyl)-3-(4-methyl-2,5-dioxo-4-(2-thiophen-2-yl)ethyl)imidazolidin-1-yl)urea;
1-(4-Bromo-2-fluorophenyl)-3-(4-methyl-2,5-dioxo-4-(2-thiophen-2-yl)ethyl)imidazolidin-1-yl)urea;
1-(4-Bromo-2-fluorophenyl)-3-(4-(4-hydroxyphenethyl)-4-methyl-2,5-dioxoimidazolidin-1-yl)urea;
1-(4-Bromophenyl)-3-(4-methyl-4-(2-(5-methylfuran-2-yl)ethyl)2,5-dioxoimidazolidin-1-yl)urea;
1-(4-Bromophenyl)-3-(4-(3-fluoro-4-hydroxyphenethyl)-4-methyl-2,5-dioxoimidazolidin-1-yl)urea;
1-(4-Bromophenyl)-3-(4-(3-fluoro-4-hydroxyphenethyl)-4-methyl-2,5-dioxoimidazolidin-1-yl)urea;

1-(4-Bromophenyl)-3-(4-isopropyl-4-(2-((4-methoxy-benzyl)oxy)ethyl)-2,5-dioxoimidazolidin-1-yl)urea;
1-(4-Bromophenyl)-3-(4-(2-hydroxyphenethyl)-4-methyl-2,5-dioxoimidazolidin-1-yl)urea;
1-(4-Bromo-2-fluorophenyl)-3-(4-(2-hydroxyphenethyl)-4-methyl-2,5-dioxoimidazolidin-1-yl)urea;
1-(4-Bromophenyl)-3-(4-(3-hydroxyphenethyl)-4-methyl-2,5-dioxoimidazolidin-1-yl)urea;
1-(4-Bromo-2-fluorophenyl)-3-(4-(3-hydroxyphenethyl)-4-methyl-2,5-dioxoimidazolidin-1-yl)urea;
1-(4-Bromophenyl)-3-(4-methyl-2,5-dioxo-4-(2-(pyridin-4-yl)ethyl)imidazolidin-1-yl)urea;
1-(4-Bromo-2-fluorophenyl)-3-(4-methyl-2,5-dioxo-4-(pyridin-4-yl)ethyl)imidazolidin-1-yl)urea;
1-(4-Bromophenyl)-3-(4-isopropyl-4-(((4-methoxybenzyl)oxy)methyl)-2,5-dioxoimidazolidin-1-yl)urea;
1-(4-Bromo-2-fluorophenyl)-3-(4-isopropyl-4-(((4-methoxybenzyl)oxy)methyl)-2,5-dioxoimidazolidin-1-yl)urea;
Methyl 4-(2-(1-(3-(4-Bromophenyl)ureido)-4-methyl-2,5-dioxoimidazolidin-4-yl)ethyl)benzoate;
Methyl 2-(2-(1-(3-(4-bromophenyl)ureido)-4-methyl-2,5-dioxoimidazolidin-4-yl)ethyl)benzoate;
Methyl 2-(2-(1-(3-(4-bromophenyl)ureido)-4-ethyl-2,5-dioxoimidazolidin-4-yl)ethyl)benzoate;
Methyl 2-(2-(1-(3-(4-bromo-2-fluorophenyl)ureido)-4-ethyl-2,5-dioxoimidazolidin-4-yl)ethyl)benzoate;
Ethyl 2-(1-(3-(4-bromo-2-fluorophenyl)ureido)-4-isopropyl-2,5-dioxoimidazolidin-4-yl)acetate;
Ethyl 2-(1-(3-(4-bromophenyl)ureido)-4-isopropyl-2,5-dioxoimidazolidin-4-yl)acetate;
1-(4-Bromophenyl)-3-[4-(1H-indol-3-ylmethyl)-4-methyl-2,5-dioxoimidazolidin-1-yl]urea;
1-(4-Bromo-2-fluorophenyl)-3-[4-(5-ethyl-1H-indol-2-yl)-4-methyl-2,5-dioxoimidazolidin-1-yl]urea;
1-(4-Bromophenyl)-3-(4,4-dicyclopropyl-2,5-dioxoimidazolidin-1-yl)urea;
1-(4-Bromophenyl)-3-[2,5-dioxo-4,4-di(propan-2-yl)imidazolidin-1-yl]urea;
Ethyl-3-[1-{[(4-bromophenyl)carbamoyl]amino}-2,5-dioxo-4-(propan-2-yl)imidazolidin-4-yl]propanoate;
1-(4-Bromophenyl)-3-(4,4-dimethyl-2,5-dioxo-3-phenylimidazolidin-1-yl)urea;
(−)-1-(4-Bromophenyl)-3-(4-methyl-2,5-dioxo-4-phenethylimidazolidin-1-yl)urea;
(+)-1-(4-Bromophenyl)-3-(4-methyl-2,5-dioxo-4-phenethylimidazolidin-1-yl)urea;
(+)-1-(4-Bromophenyl)-3-(4-ethyl-4-isopropyl-2,5-dioxoimidazolidin-1-yl)urea;
(−)-1-(4-Bromophenyl)-3-(4-ethyl-4-isopropyl-2,5-dioxoimidazolidin-1-yl)urea;
1-(4-Bromophenyl)-3-(4-(hydroxymethyl)-4-isopropyl-2,5-dioxoimidazolidin-1-yl)urea;
1-(4-Bromophenyl)-3-(4-(2-hydroxyethyl)-4-isopropyl-2,5-dioxoimidazolidin-1-yl)urea;
1-(4-Bromo-2-fluorophenyl)-3-(4-(2-hydroxymethyl)-4-isopropyl-2,5-dioxoimidazolidin-1-yl)urea;
4-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-methyl-2,5-dioxoimidazolidin-4-yl)ethyl)benzoic acid;
2-(2-(1-(3-(4-Bromophenyl)ureido)-4-ethyl-2,5-dioxoimidazolidin-4-yl)ethyl)benzoic acid;
Methyl 2-(2-(1-(3-(4-bromo-2-fluorophenyl)ureido)-4-ethyl-2,5-dioxoimidazolidin-4-yl)ethyl)benzoate;
2-(1-(3-(4-Bromophenyl)ureido)-4-isopropyl-2,5-dioxoimidazolidin-4-yl)acetic acid;
2-(1-(3-(4-Bromo-2-fluorophenyl)ureido)-4-isopropyl-2,5-dioxoimidazolidin-4-yl)acetic acid;
3-[1-{[(4-bromophenyl)carbamoyl]amino}-2,5-dioxo-4-(propan-2-yl)imidazolidin-4-yl]propanoic acid;
2-(1-(3-(4-Bromophenyl)ureido)-4-isopropyl-2,5-dioxoimidazolidin-4-yl)-N-(2-hydroxyethyl)acetamide;
tert-Butyl 2-(2-(1-(3-(4-bromophenyl)ureido)-4-isopropyl-2,5-dioxoimidazolidin-4-yl)acetamido)acetate;
Diethyl((2-(1-(3-(4-bromophenyl)ureido)-4-isopropyl-2,5-dioxoimidazolidin-4-yl)acetamido)methyl)phosphonate;
2-(1-(3-(4-Bromophenyl)ureido)-4-isopropyl-2,5-dioxoimidazolidin-4-yl)-N,N-bis(2-hydroxyethyl)acetamide;
Diisopropyl((2-(1-(3-(4-bromophenyl)ureido)-4-isopropyl-2,5-dioxoimidazolidin-4-yl)acetamido)methyl)phosphonate;
Ethyl hydrogen((2-(1-(3-(4-bromophenyl)ureido)-4-isopropyl-2,5-dioxoimidazolidin-4-yl)acetamido)methyl)phosphonate;
tert-Butyl 2-(2-(1-(3-(4-bromophenyl)ureido)-4-isopropyl-2,5-dioxoimidazolidin-4-yl)acetamido)-2-methylpropanoate;
tert-Butyl 3-(2-(1-(3-(4-bromophenyl)ureido)-4-isopropyl-2,5-dioxoimidazolidin-4-yl)acetamido)propanoate;
2-(2-(1-(3-(4-Bromophenyl)ureido)-4-isopropyl-2,5-dioxoimidazolidin-4-yl)acetamido)acetic acid;
3-(2-(1-(3-(4-Bromophenyl)ureido)-4-isopropyl-2,5-dioxoimidazolidin-4-yl)acetamido)propanoic acid;
2-(1-(3-(4-Bromo-2-fluorophenyl)ureido)-4-isopropyl-2,5-dioxoimidazolidin-4-yl)-N-(2-hydroxyethyl)acetamide;
2-(2-(1-(3-(4-Bromophenyl)ureido)-4-isopropyl-2,5-dioxoimidazolidin-4-yl)acetamido)-2-methylpropanoic acid; and
N-(2-Amino-2-oxoethyl)-2-(1-(3-(4-bromophenyl)ureido)-4-isopropyl-2,5-dioxoimidazolidin-4-yl)acetamide.

15. A compound selected from:
(S)-1-(4-Bromophenyl)-3-(1,3-dioxo-10,10a-dihydroimidazo[1,5-b]isoquinolin-2(1H,3H,5H)-yl)urea, and
(S)-1-(4-Bromo-2-fluorophenyl)-3-(1,3-dioxo-10,10a-dihydroimidazo[1,5-b]isoquinolin-2(1H,3H,5H)-yl)urea.

* * * * *

UNITED STATES PATENT AND TRADEMARK OFFICE
CERTIFICATE OF CORRECTION

PATENT NO.        : 8,492,556 B2
APPLICATION NO.   : 13/673800
DATED             : July 23, 2013
INVENTOR(S)       : Richard L. Beard et al.

It is certified that error appears in the above-identified patent and that said Letters Patent is hereby corrected as shown below:

In the Specifications

In column 4, line 12, delete "C(O)R$^{16}$," and insert -- C(O)R$^{10}$, --, therefor.

In column 6, line 33, delete "aryl" and insert -- aryl, --, therefor.

In column 8, line 22, delete "aryl" and insert -- aryl, --, therefor.

In column 14, line 1, delete "5" and insert -- 5; --, therefor.

In column 16, line 32, delete "5" and insert -- 5; --, therefor.

In column 24, line 35, delete "C(O)R$^{19}$," and insert -- C(O)R$^{10}$, --, therefor.

In column 29, line 32, delete "tetrahydronaphtalene." and insert -- tetrahydronaphthalene. --, therefor.

In column 29, lines 53-54, delete "tetrahydronaphtalene" and insert -- tetrahydronaphthalene --, therefor.

In column 30, line 24, delete "—(COON)," and insert -- —(COOH), --, therefor.

In column 30, line 29, delete "—(O(C$_{1-8}$" and insert -- —(C(C$_{1-8}$ --, therefor.

In column 30, line 30, delete "—(O(C$_{1-8}$" and insert -- —(C(C$_{1-8}$ --, therefor.

In column 30, line 52, delete "—(COON)," and insert -- —(COOH), --, therefor.

In column 30, line 56, delete "alkyl))," and insert -- alkyl))$_n$ --, therefor.

In column 30, line 56, delete "—(O(C$_{1-8}$" and insert -- —(C(C$_{1-8}$ --, therefor.

In column 30, line 57, delete "alkyl))," and insert -- alkyl))$_n$ --, therefor.

In column 30, line 61, delete "alkyl))," and insert -- alkyl))$_n$ --, therefor.

In column 30, line 63, delete "alkyl))," and insert -- alkyl))$_n$ --, therefor.

In column 30, line 63, delete "alkyl))," and insert -- alkyl))$_n$ --, therefor.

In column 31, lines 54-55, delete "methoxypheynyl)" and insert -- methoxyphenyl) --, therefor.

In column 34, line 36, delete "Chemica" and insert -- Chimica --, therefor.

In column 34, line 46, delete "Chemica" and insert -- Chimica --, therefor.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,492,556 B2

In column 35, line 28, delete "vasuclar" and insert -- vascular --, therefor.

In column 35, line 55, delete "accosiated" and insert -- associated --, therefor.

In column 36, line 6, delete "pigement" and insert -- pigment --, therefor.

In column 36, line 20, delete "degenartion," and insert -- degeneration, --, therefor.

In column 36, line 46, delete "vasuclar" and insert -- vascular --, therefor.

In column 37, line 6, delete "accosiated" and insert -- associated --, therefor.

In column 37, line 24, delete "pigement" and insert -- pigment --, therefor.

In column 37, line 38, delete "degenartion," and insert -- degeneration, --, therefor.

In column 38, line 3, delete "vasuclar" and insert -- vascular --, therefor.

In column 38, line 30, delete "accosiated" and insert -- associated --, therefor.

In column 38, line 48, delete "pigement" and insert -- pigment --, therefor.

In column 38, line 62, delete "degenartion," and insert -- degeneration, --, therefor.

In column 42, line 11, delete "diasteroisomeric" and insert -- diastereoisomeric --, therefor.

In column 42, line 56, delete "dicyanobenzoqu none" and insert -- dicyanobenzoquinone --, therefor.

In column 44, line 36, delete "2H" and insert -- 2H). --, therefor.

In columns 49-50, line 13, delete "1H)." and insert -- 1H), --, therefor.

In columns 49-50, line 31, delete "1H)." and insert -- 1H), --, therefor.

In column 52, line 12, delete "chloropheneyhtl)" and insert -- chlorophenethyl) --, therefor.

In column 59, line 42, delete "djcyclohexyl-," and insert -- dicyclohexyl-, --, therefor.

In column 60, line 51, delete "3, 80" and insert -- 3.80 --, therefor.

In columns 65-66, line 6, delete "(m 2H)," and insert -- (m, 2H), --, therefor.

In columns 67-68, line 40, delete "methoxypheynyl)" and insert -- methoxyphenyl) --, therefor.

In column 94, line 41, delete "(+)" and insert -- (-) --, therefor.

In column 96, line 25, delete "4H).." and insert -- 4H). --, therefor.

In column 107, line 67, delete "MuItiPROBE" and insert -- MultiPROBE --, therefor.

In the Claims

In column 113, line 32, in claim 1, delete "$SO_2R^{18};$" and insert -- $SO_2R^{16};$ --, therefor.

In column 115, line 15, in claim 1, delete "aryl" and insert -- aryl, --, therefor.

In column 122, line 12, in claim 12, delete "heterocycle," and insert -- heterocycle; --, therefor.

In column 122, line 63, in claim 12, delete "urea" and insert -- urea; --, therefor.

In column 123, lines 12-13, in claim 12, delete "methoxypheynyl)" and insert -- methoxyphenyl) --, therefor.

In column 123, line 19, in claim 12, delete "urea" and insert -- urea; --, therefor.

In column 123, line 21, in claim 12, delete "urea" and insert -- urea; --, therefor.

CERTIFICATE OF CORRECTION (continued)
U.S. Pat. No. 8,492,556 B2

In column 123, line 63, in claim 12, delete "urea" and insert -- urea; --, therefor.

In column 126, lines 16-17, in claim 14, delete "methoxypheynyl)" and insert -- methoxyphenyl) --, therefor.